(12) United States Patent
Kremenak

(10) Patent No.: US 12,037,496 B2
(45) Date of Patent: Jul. 16, 2024

(54) METHODS OF PRODUCING FUNCTIONALIZED POWDER PARTICLES

(71) Applicant: KREMENAK NANOTECH, INC., Columbia, MO (US)

(72) Inventor: Jesse Kremenak, Columbia, MO (US)

(73) Assignee: KREMENAK NANOTECH, INC., Columbia, MO (US)

( * ) Notice: Subject to any disclaimer, the term of this patent is extended or adjusted under 35 U.S.C. 154(b) by 182 days.

(21) Appl. No.: 17/194,148

(22) Filed: Mar. 5, 2021

(65) Prior Publication Data

US 2022/0169863 A1  Jun. 2, 2022

Related U.S. Application Data

(63) Continuation of application No. PCT/US2019/050071, filed on Sep. 6, 2019.

(60) Provisional application No. 62/728,570, filed on Sep. 7, 2018.

(51) Int. Cl.
| | | |
|---|---|---|
| *C09C 1/28* | (2006.01) | |
| *C01B 33/02* | (2006.01) | |
| *C09C 3/04* | (2006.01) | |
| *C09C 3/06* | (2006.01) | |

(52) U.S. Cl.
CPC .............. *C09C 1/28* (2013.01); *C01B 33/02* (2013.01); *C09C 3/04* (2013.01); *C09C 3/063* (2013.01); *C09C 3/066* (2013.01); *C01P 2002/72* (2013.01); *C01P 2002/82* (2013.01); *C01P 2002/84* (2013.01); *C01P 2004/02* (2013.01); *C01P 2004/03* (2013.01); *C01P 2004/16* (2013.01); *C01P 2004/42* (2013.01); *C01P 2004/61* (2013.01); *C01P 2004/62* (2013.01)

(58) Field of Classification Search
None
See application file for complete search history.

(56) References Cited

U.S. PATENT DOCUMENTS

| | | |
|---|---|---|
| 2011/0053251 A1 | 3/2011 | Birkner et al. |
| 2011/0268779 A1 | 11/2011 | Canham |
| 2012/0099185 A1 | 4/2012 | Yokoyama et al. |
| 2017/0174848 A1 | 6/2017 | Gifford et al. |

FOREIGN PATENT DOCUMENTS

| | | |
|---|---|---|
| JP | H11290626 A | 10/1999 |
| JP | 2004159636 A | 6/2004 |
| WO | WO-2004099384 A2 | 11/2004 |
| WO | WO-2015031956 A1 | 3/2015 |
| WO | WO-2017129814 A1 | 8/2017 |
| WO | WO-2020051536 A1 | 3/2020 |

OTHER PUBLICATIONS

Pandurangi, Raghoottama S., et al. "Surface and bulk infrared modes of crystalline and amorphous silica particles: a study of the relation of surface structure to cytotoxicity of respirable silica." Environmental Health Perspectives 86 (1990): 327-336. (Year: 1990).*
Zegzulka, Jiř, et al. "Flow characterization methods of glidants." Proceedings of the 8th International Conference on Nanomaterials—Research & Application, Brno, Czech Republic. 2016. (Year: 2016).*
Ottery, J., and I. P. Gormley. "Some factors affecting the haemolytic activity of silicate minerals." The Annals of Occupational Hygiene 21.2 (1978): 131-139. (Year: 1978).*
Isquith, A. J., and C. J. McCollum. "Surface kinetic test method for determining rate of kill by an antimicrobial solid." Applied and Environmental Microbiology 36.5 (1978): 700-704. (Year: 1978).*
Saseendran Nair, Shilpa, et al. "The antibacterial potency and antibacterial mechanism of a commercially available surface-anchoring quaternary ammonium salt (SAQAS)-based biocide in vitro." Journal of Applied Microbiology 133.4 (2022): 2583-2598. (Year: 2022).*
Bhadra, C., et al., "Subtle Variations in Surface Properties of Black Silicon Surfaces Influence the Degree of Bactericidal Efficiency", Nano-Micro Letters, 2018, vol. 10, No. 36, pp. 1-8.
Han et al., Metal-assisted chemical etching of silicon and nanotechnology applications. Nanotoday 9(3): 271-304 (2014).
Han, S., et al., "Superhydrophilic nanopillar-structured quartz surfaces for the prevention of biofilm formation in optical devices", Applied Surface Science, 2018, vol. 429, pp. 244-252.
Hu, H. et al., "Bio-inspired silicon nanospikes fabricated by metal-assisted chemical etching for antibacterial surfaces", Applied Physics Letters, 2017, vol. 111, No. 25, pp. 1-5.
Kamel et al., Preparation and evaluation of nanoporous-pyramids structured silicon powder as an effective photocatalyst for degradation of methyl red. International Journal of Environmental Science and Technology 16: 2101-2108 (2019). Abstract only.
PCT/US2019/050071 International Preliminary Report on Patentability dated Mar. 9, 2021.
PCT/US2019/050071 International Search Report and Written Opinion dated Dec. 30, 2019.
Sahin, F., "Using Sand Particles for the Disruption of Cell Walls of Gram-Positive Bacteria and Mycobacteria", Journal of Bacteriology and Parasitology, 2016, vol. 7, No. 5, pp. 1-2.
Vassallo, E., et al., "Bactericidal performance of nanostructured surfaces by fluorocarbon plasma", Materials Science and Engineering C, 2017, vol. 80, pp. 117-121.
Zhao et al., Hierarchical Micro/Nano Porous Silicon Li-ion Battery Anodes. Chem Commun (Camb) 48(42): 5079-5081 (2012).
European Patent Application No. 19857914.6 Extended European Search Report dated May 19, 2022.

(Continued)

*Primary Examiner* — Robert J Yamasaki
(74) *Attorney, Agent, or Firm* — WILSON SONSINI GOODRICH & ROSATI

(57) ABSTRACT

The present disclosure provides functionalized powder particles and methods of forming functionalized powder particles. The functionalization is acquired through the formation of primary and/or secondary structures on a powder particle. Functionalization can be controlled to bring about changes in a broad range of physical and/or chemical properties.

19 Claims, 38 Drawing Sheets

(56) References Cited

OTHER PUBLICATIONS

Kamel, L, et al. Preparation and Evaluation of Nanoporous-pyramids Structured Silicon Powder as an Effective Photocatalyst for Degradation of Methyl Red. International Journal of Environmental Science and Technology. vol. 16 (2019): p. 2101-2108.

* cited by examiner

Nanowire with pores

Multiple nanowires on larger nanowire

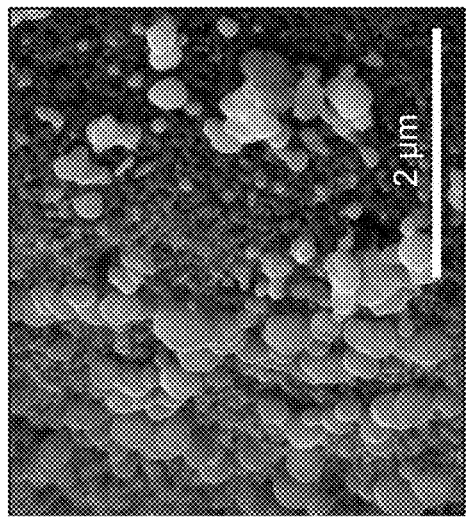
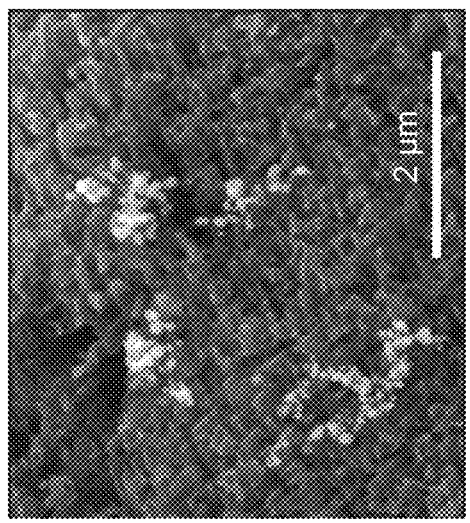
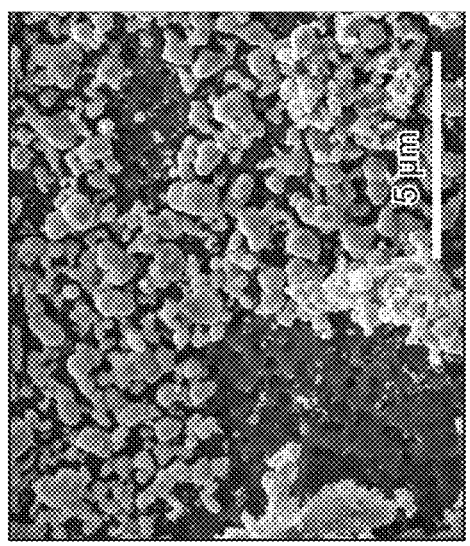
FIG. 13C
FIG. 13B
FIG. 13A

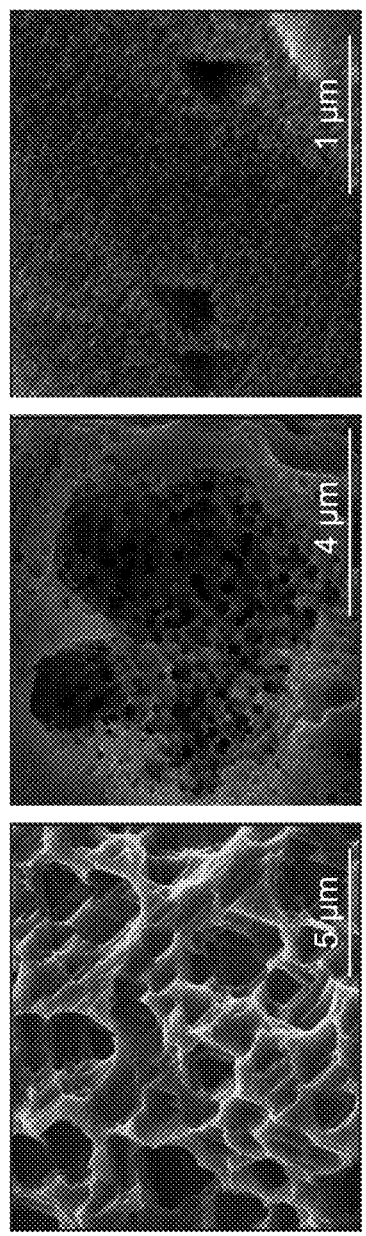

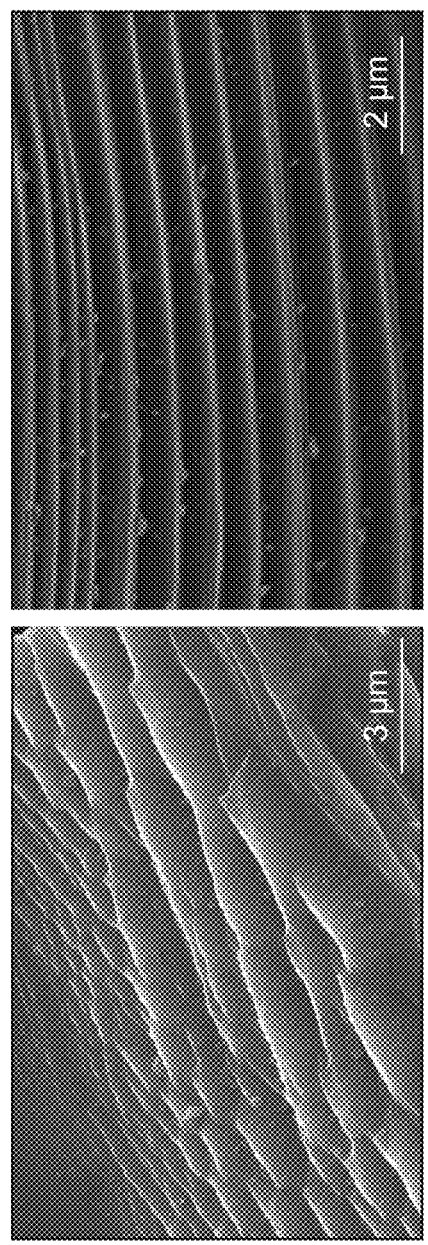

| Sample | 2θ Position (degrees) | 2θ Position σ | Intensity (cps) | Intensity σ | FWHM (degrees) | FWHM σ | h | k | l | d (Å) | Δd (Å) | % Change |
|---|---|---|---|---|---|---|---|---|---|---|---|---|
| Si Powder | 28.3683 | 0.00003 | 3237.0 | 0.9 | 0.2348 | 0.0001 | 1 | 1 | 1 | 3.14356 | N/A | N/A |
| Fn. Powder | 28.3122 | 0.00003 | 2054.5 | 0.6 | 0.1724 | 0.0001 | 1 | 1 | 1 | 3.14966 | 0.00610 | 0.194% |
| Si Powder | 47.2337 | 0.0004 | 331.3 | 0.7 | 0.4153 | 0.0011 | 2 | 2 | 0 | 1.92276 | N/A | N/A |
| Fn. Powder | 47.2296 | 0.0004 | 254.3 | 0.5 | 0.4132 | 0.0010 | 2 | 2 | 0 | 1.92292 | 0.00016 | 0.008% |
| Si Powder | 56.0139 | 0.0001 | 1011.4 | 0.8 | 0.3419 | 0.0003 | 3 | 1 | 1 | 1.64040 | N/A | N/A |
| Fn. Powder | 56.1014 | 0.0001 | 668.3 | 0.6 | 0.2482 | 0.0003 | 3 | 1 | 1 | 1.63804 | -0.00235 | -0.143% |
| Si Powder | 69.0628 | 0.0002 | 647.7 | 0.8 | 0.3382 | 0.0005 | 4 | 0 | 0 | 1.35889 | N/A | N/A |
| Fn. Powder | 69.0402 | 0.0015 | 62.0 | 0.5 | 0.3479 | 0.0037 | 4 | 0 | 0 | 1.35928 | 0.00039 | 0.029% |
| Si Powder | 76.2731 | 0.0002 | 561.8 | 0.8 | 0.3564 | 0.0006 | 3 | 3 | 1 | 1.24737 | N/A | N/A |
| Fn. Powder | 76.2978 | 0.0007 | 135.1 | 0.5 | 0.3511 | 0.0017 | 3 | 3 | 1 | 1.24702 | -0.00034 | -0.027% |

|           | Powder Mass (g) | Cells lysed |
|-----------|-----------------|-------------|
| Sample A  | 0.1             | 57.23%      |
| Sample B  | 0.05            | 38.99%      |
| Si powder | 0.1             | 8.81%       |
| Control   | n/a             | 0.00%       |

FIG. 31

| Etch Duration (min) | Stir Speed (rpm) | Etch Depth (μm) |
|---|---|---|
| 30 | 250 | 0.5 |
| 60 | 250 | 1.0 |
| 60 | 0 | 10 |
| 90 | 250 | 1.5 |

FIG. 32

METHODS OF PRODUCING FUNCTIONALIZED POWDER PARTICLES

CROSS REFERENCE

This application is continuation of PCT/US2019/050071, filed Sep. 6, 2019, which claims the benefit of U.S. Provisional Application No. 62/728,570, filed Sep. 7, 2018, both of which are incorporated herein in their entireties by references for all purposes.

BACKGROUND OF THE INVENTION

Silicon is the second most abundant element in the earth's crust and is used commercially in the construction, steel refining and electronics industries. Pure silicon is an intrinsic semiconductor, but has too low a conductivity to be used in electronics without doping with small concentrations of other elements to increase its conductivity. The monocrystalline allotrope of silicon in particular is used to produce silicon wafers used in the semiconductor industry. Recent studies have focused on the formation of nanowires on silicon wafers for applications in photovoltaics and batteries. Synthesis methods for silicon nanowires include laser beam ablation, ion beam etching, chemical vapor deposition and vapor liquid solid growth, with current research focused on the controlled formation of the nanowires in a particular orientation.

SUMMARY OF THE INVENTION

Previous nanowire fabrication methods often require expensive high temperature and high-vacuum environments, which limit the size of the treated substrate, scalability and production throughput. Additionally, previous nanowire fabrication methods typically require high purity, monocrystalline silicon wafers, which are expensive to produce with limited potential applications due to their flat, rigid shape. There remains a considerable need for methods for producing structures, including nanostructures such as nanowires, on (e.g., crystalline, polycrystalline, semi-crystalline or amorphous) semiconductor powders, particles or grains. The present disclosure addresses this need and provides related advantages as well.

In certain aspects, the present disclosure provides a method of forming structures on a (e.g., powder) particle (e.g., microparticle), the method comprising: (a) providing one or more (e.g., crystalline, polycrystalline, semi-crystalline or amorphous) semiconductor or insulator powder particle; (b) (e.g., optionally), removing surface contaminants from the one or more powder particle; (c) (e.g., optionally), removing oxides from the one or more powder particle; (d) forming a (e.g., first type of) structure on the one or more powder particle, thereby forming one or more homofunctionalized powder particle; and (e) (e.g., optionally), forming a (e.g., second type of) structure on the one or more homofunctionalized powder particle, thereby forming one or more heterofunctionalized powder particle. In some embodiments, the first and/or the second types of structures are (e.g., optionally) selected from the group consisting of pores, pits, craters, nanowires, cones, pinnacles, hoodoos, coral, cords, walls, trenches, fins, ridges, crags, pyramids and inverted pyramids. In some embodiments, the (e.g., crystalline, polycrystalline, semi-crystalline or amorphous) powder particle is an (e.g., elemental or compound crystalline, polycrystalline, semi-crystalline or amorphous) powder particle comprising group-IVA elements, groups-IV-VI compounds, groups II-IVB compounds, groups I-VII compounds, groups II-VI compounds, groups III-V compounds, groups IV-IV compounds, transition metal oxides, and compounds consisting of three or more elements. The powder particle may comprise one or more crystal grains, or the powder particle may consist of a single crystal grain.

In practicing any of the subject methods, the method may comprise (b) removing surface contaminants from the one or more powder particle. In some embodiments, the method comprises (c) removing oxides from the one or more powder particle. In some embodiments, the method comprises (e) forming a (e.g., second type of) structure on the one or more homofunctionalized powder particle, thereby forming one or more heterofunctionalized powder particle. The forming of (d) may comprise forming a (e.g., first type of) structure on a surface or within a pore of the powder particle. The forming of (e) may comprise forming a (e.g., second type of) structure on a surface or within a pore of the powder particle. At least one of the forming of (d) and (e) may comprise lithography. In some embodiments, each of the forming of (d) and (e) independently comprises a process selected from the group consisting of metal-assisted chemical etching and chemical etching. At least one of the forming of (d) and (e) may comprise metal-assisted chemical etching, wherein the metal-assisted chemical etching comprises depositing metal ions on a surface of the powder particle and etching the powder particle by exposing the metal ions to an etchant. The metal ions may be selected from metals to include, but not limited to, (e.g., noble metals and precious metals). In some embodiments, the etchant is a plasma, gas or solution. The etchant may be a solution comprising an etchant and an oxidizing agent. The first type of structure may be a sub-millistructure, such as a microstructure or a nanostructure. In some embodiments, the second type of structure is a sub-millistructure, such as a microstructure or a nanostructure. A method described herein may further comprise subjecting the one or more functionalized powder particle to a process selected from the group consisting of film coating, plating, chemical functionalization, doping, nanoparticle decoration, lithography, and combinations thereof. The first and the second types of structures may be selected from the group consisting of pores, pits, craters, nanowires, cones, pinnacles, hoodoos, coral, cords, walls, trenches, fins, ridges, crags, pyramids and inverted pyramids.

In certain aspects, the present disclosure provides a surface comprising one or more functionalized (e.g., crystalline, polycrystalline, semi-crystalline or amorphous) (e.g., semiconductor or insulator) powder particle, wherein the powder particle (e.g., optionally) comprises one or more structures selected from the group consisting of pores, pits, craters, nanowires, cones, pinnacles, hoodoos, coral, cords, walls, trenches, fins, ridges, crags, pyramids and inverted pyramids, and wherein the diameter of the powder particle is between 0.01 μm and 10,000 μm. The (e.g., crystalline, polycrystalline, semi-crystalline or amorphous) powder particle may be an (e.g., elemental or compound crystalline, polycrystalline, semi-crystalline or amorphous) powder particle selected from the group consisting of group-IVA elements, groups-IV-VI compounds, groups II-IVB compounds, groups I-VII compounds, groups II-VI compounds, groups III-V compounds, groups IV-IV compounds, transition metal oxides, and compounds consisting of three or more elements. In some embodiments, the powder particle comprises one or more crystal grains, such as a single crystal grain. The diameter of the powder particle may be between 0.1 μm and 1,000 In some embodiments, the powder particle comprises two or more structures selected from the group consisting of pores, pits, craters, nanowires, cones, pinnacles, hoodoos, coral, cords, walls, trenches, fins, ridges, crags, pyramids and inverted pyramids. The one or more structures may be submillistructures, such as microstructures or nanostructures. In some embodiments, the mean diameter of the smallest 30% of powder particles is 200% smaller than the mean diameter of the largest 10% of powder particles. A surface described herein may further comprise a film separating the powder particle from the atmosphere. The surface may be anti-reflective, reflective, absorbing, adsorbing, adhesive, refractive, abrasive, conductive, insulating, chemically reactive, chemically inert, luminescent, antimicrobial, cell lysing, omniphobic, hydrophobic, hydrophilic, antifouling, non-stick, non-slip, anti-static, or a combination thereof. In some embodiments, the powder particle comprises one or more structures selected from the group consisting of pores, pits, craters, nanowires, cones, pinnacles, hoodoos, coral, cords, walls, trenches, fins, ridges, crags, pyramids and inverted pyramids. In some aspects, the present disclosure provides a method of transferring or replicating the surface structure of an article, the method comprising using a surface comprising one or more functionalized (e.g., crystalline, polycrystalline, semi-crystalline or amorphous semiconductor or insulator) powder particle described herein as a template or mold.

In some aspects, the present disclosure provides a heterofunctionalized (e.g., crystalline, polycrystalline or semi-crystalline semiconductor or insulator) powder particle, wherein the powder particle comprises two or more types of submillistructures. In some aspects, the present disclosure provides a functionalized (e.g., crystalline, polycrystalline, semi-crystalline or amorphous semiconductor or insulator) powder particle, wherein the powder particle comprises a submillistructure and further comprises a film coating, plating, chemical functionalization, a dopant, a nanoparticle decoration, or a surface termination. In some aspects, the present disclosure provides a homofunctionalized (e.g., crystalline, polycrystalline, semi-crystalline or amorphous semiconductor or insulator) powder particle, wherein the powder particle comprises a structure selected from the group consisting of pits, craters, cones, pinnacles, hoodoos, coral, cords, walls, trenches, fins, ridges, crags, pyramids and inverted pyramids. In some aspects, the present disclosure provides a homofunctionalized (e.g., crystalline, polycrystalline, semi-crystalline or amorphous semiconductor or insulator) powder particle, wherein the powder particle comprises a structure selected from the group consisting of pores, pits, craters, nanowires, cones, pinnacles, hoodoos, coral, cords, walls, trenches, fins, ridges, crags, pyramids and inverted pyramids, and wherein the powder particle is not an elemental silicon particle. The diameter of a powder particle described herein may be between 0.01 µm and 10,000 µm. In some embodiments, the diameter of the particle is between 0.1 µm and 1,000 µm. The particle may be an elemental or compound (e.g., crystalline, polycrystalline, semi-crystalline or amorphous) powder particle selected from the group consisting of group-IVA elements, groups-IV-VI compounds, groups II-IVB compounds, groups I-VII compounds, groups II-VI compounds, groups III-V compounds, groups IV-IV compounds, transition metal oxides, and compounds consisting of three or more elements. In some embodiments, the particle comprises one or more crystal grains. The particle may consist of a single crystal grain. The two or more types of submillistructures may be selected from the group consisting of pores, pits, craters, nanowires, cones, pinnacles, hoodoos, coral, cords, walls, trenches, fins, ridges, crags, pyramids and inverted pyramids. In some embodiments, the two or more types of structures are selected from microstructures and nanostructures.

A particle described herein may reflect at most 10% of all electromagnetic radiation (e.g., specular and/or diffuse) between the wavelengths of 10 nm and 1 mm. In some embodiments, the particle reflects at most 10% of all electromagnetic radiation (e.g., specular and/or diffuse) between the wavelengths of 10 nm and 400 nm. In some embodiments, the particle reflects at most 10% of all electromagnetic radiation (e.g., specular and/or diffuse) between the wavelengths of 300 nm and 1,000 nm. In some embodiments, the particle reflects at most 10% of all electromagnetic radiation (e.g., specular and/or diffuse) between the wavelengths of 700 nm and 1 mm. The particle may comprise two or more overlapping structures. The particle may be regular or irregular in shape. A particle described herein may further comprise a film coating, plating, chemical functionalization, a dopant, a nanoparticle decoration, or a surface termination. In some embodiments, the particle exhibits antimicrobial properties.

In some aspects, the present disclosure provides a method of rupturing a cell membrane, the method comprising contacting a cell with a (e.g., crystalline, polycrystalline, semi-crystalline, or amorphous semiconductor or insulator) powder particle described herein, wherein the powder particle physically or chemically interacts with the cell membrane, thereby rupturing the cell membrane.

In some aspects, the present disclosure provides a method of altering a characteristic of an article, the method comprising incorporating one or more functionalized (e.g., crystalline, polycrystalline, semi-crystalline or amorphous) (e.g., semiconductor or insulator) powder particle into the article, wherein the powder particle comprises one or more submillistructures, and wherein the diameter of the powder particle is between 0.01 µm and 10,000 µm. The (e.g., crystalline, polycrystalline, semi-crystalline or amorphous) powder particle may be an elemental or compound (e.g., crystalline, polycrystalline, semi-crystalline or amorphous) powder particle selected from the group consisting of group-IVA elements, groups-IV-VI compounds, groups II-IVB compounds, groups I-VII compounds, groups II-VI compounds, groups III-V compounds, groups IV-IV compounds, transition metal oxides, and compounds consisting of three or more elements. The powder particle may comprise one or more crystal grains. For example, the powder particle may consist of a single crystal grain. The diameter of the powder particle may be between 0.1 and 1,000 µm. The powder particle may comprise two or more structures selected from the group consisting of pores, pits, craters, nanowires, cones, pinnacles, hoodoos, coral, cords, walls, trenches, fins, ridges, crags, pyramids and inverted pyramids. In some embodiments, the one or more submillistructures are selected from the group consisting of pores, pits, craters, nanowires, cones, pinnacles, hoodoos, coral, cords, walls, trenches, fins, ridges, crags, pyramids and inverted pyramids. The one or more structures may be selected from microstructures and nanostructures. In some examples, the article is selected from the group consisting of a medical device, cookware, an appliance, a countertop, a vehicle, a boat, and an aircraft. The article may be selected from the group consisting of office supplies, office equipment, electronics, containers, kitchenware, cookware, housewares, textiles, hardware, consumer products, vehicles and vessels, filters, pumps, aquatic equipment, surfaces, furniture, appliances, devices, building materials, military equipment, tools, solar cells, currency, medical supplies, medical devices, paper goods, manufacturing equipment, food processing equipment and optical equipment. In some embodiments, the article comprises rubber, plastic, metal, glass or ceramic. The altering may comprise one or more of reducing absorbance of visible light, increasing absorbance of visible light, reducing reflectivity of light, increasing antimicrobial activity, increasing antifouling activity, increasing hydrophobicity, increasing hydrophilicity, increasing electrical conductivity, increasing electrical resistivity, increasing photoluminescence, increasing the surface energy, reducing the surface energy, increasing the coefficient of friction, and reducing the coefficient of friction of the article. The incorporating may comprise coating the article with the powder particle or embedding the powder particle in the article. A method described herein may further comprise subjecting the article to a process selected from the group consisting of film coating, plating, chemical functionalization, doping, nanoparticle decoration, lithography, and combinations thereof.

Provided in specific embodiments herein, is a method of (e.g., physically and/or non-chemically) lysing a cell (or population thereof), the method comprising contacting the cell (or population thereof) with a functionalized (e.g., crystalline, polycrystalline, semi-crystalline, or amorphous) powder particle, wherein the powder particle comprises one or more submillistructures (e.g., as described in any suitable embodiment herein), and wherein the diameter of the powder particle is between 0.01 and 10,000 microns. In specific embodiments, the functionalized particle is configured in the surface of an article. In other specific embodiments, the functionalized particle is not embedded within another material or surface thereof, such as in loose powder form. In some embodiments, all or part of the cells are physically lysed, such as wherein at least 30% of the cells are lysed (e.g., wherein at least 50% of the cells are lysed). Any suitable particle provided herein is optionally utilized.

Provided in some specific embodiments herein is a low reflection surface (e.g., of an article) comprising one or more functionalized crystalline, polycrystalline, semi-crystalline, or amorphous (e.g., semiconductor or insulator) powder particle (e.g., the surface comprising one or more particle being configured on the surface thereof and/or one or more particle embedded in the surface thereof), wherein the powder particle (e.g., optionally) comprises one or more structures selected from pores, pits, craters, nanowires, cones, pinnacles, hoodoos, coral, cords, walls, fins, ridges, crags, pyramids, and inverted pyramids, and wherein the diameter of the powder particle is between 0.01 and 10,000 microns. In certain embodiments, the (e.g., specular and/or diffuse light) reflectance is about 25% or less (e.g., about 15% or less, about 10%, or less, or the like) than an otherwise identical surface, absent the one or more powder particle (e.g., at a particular wavelength, such as an IR, visible, and/or UV wavelength (such as any one or more wavelength light described in the examples and figures demonstrated herein)). In more specific embodiments, the (e.g., specular and/or diffuse light) reflectance of the surface is less than 5% (e.g., less than 4%, less than 3%, less than 2%, less than 1%, less than 0.5%, less than 0.2%, or the like) (e.g., at a particular wavelength, such as an IR, visible, and/or UV wavelength). In certain embodiments, the surface comprises a (e.g., bulk) material onto and/or into which the powder particle(s) are incorporated, and the material is silicon or silicon monoxide. In some embodiments, the powder particle(s) are any particle(s) of any one of the preceding claims. Any suitable particle provided herein is optionally utilized.

Provided in other embodiments herein is a method of altering the light reflectance of an article, the method comprising incorporating one or more functionalized crystalline, polycrystalline, semi-crystalline, or amorphous semiconductor or insulator powder particle into the article (e.g., a surface and/or a bulk material thereof), wherein the powder particle comprises one or more submillistructures, and wherein the diameter of the powder particle is between 0.01 and 10,000 microns. In some embodiments, the crystalline, polycrystalline, semi-crystalline, or amorphous powder particle is an elemental or compound crystalline, polycrystalline, semi-crystalline, or amorphous powder particle selected from group-IVA elements, groups-IV-VI compounds, groups II-IVB compounds, groups I-VII compounds, groups II-VI compounds, groups III-V compounds, groups IV-IV compounds, transition metal oxides, and compounds comprising three or more elements. In certain embodiments, the one or more submillistructures are selected from pores, pits, craters, nanowires, cones, pinnacles, hoodoos, coral, cords, walls, fins, ridges, crags, pyramids, and inverted pyramids. In some embodiments, the (e.g., specular and/or diffuse light) reflectance is about 25% or less (e.g., about 15% or less, about 10%, or less, or the like) than an otherwise identical surface, absent the one or more powder particle (e.g., at a particular wavelength, such as an IR, visible, and/or UV wavelength). In certain embodiments, the (e.g., specular and/or diffuse light) reflectance of the surface is less than 5% (e.g., less than 4%, less than 3%, less than 2%, less than 1%, less than 0.5%, less than 0.2%, or the like) (e.g., at a particular wavelength, such as an IR, visible, and/or UV wavelength). Any suitable particle provided herein is optionally utilized.

Provided in some embodiments herein is a fade resistant pigment (or article comprising the pigment incorporated therein, or into a surface thereof) comprising one or more functionalized crystalline, polycrystalline, semi-crystalline, or amorphous (e.g., semiconductor or insulator) powder particle, wherein the powder particle (e.g., optionally) comprises one or more structures selected from pores, pits, craters, nanowires, cones, pinnacles, hoodoos, coral, cords, walls, fins, ridges, crags, pyramids, and inverted pyramids, and wherein the diameter of the powder particle is between 0.01 and 10,000 microns. In certain embodiments, the powder particle(s) are any particle(s) of any one of the preceding claims. Any suitable particle provided herein is optionally utilized.

In certain embodiments, provided herein is a method of forming a fade resistant article, the method comprising incorporating one or more functionalized crystalline, polycrystalline, semi-crystalline, or amorphous (e.g., semiconductor or insulator) powder particle that resists fading from light exposure into the article (e.g., the surface or bulk of a material thereof), wherein the powder particle comprises one or more structures selected from pores, pits, craters, nanowires, cones, pinnacles, hoodoos, coral, cords, walls, fins, ridges, crags, pyramids, and inverted pyramids, and wherein the diameter of the powder particle is between 0.01 and 10,000 microns. Any suitable particle provided herein is optionally utilized.

In some embodiments, provided herein is a functionalized crystalline, polycrystalline, semi-crystalline or amorphous (e.g., semiconductor or insulator) particle, wherein the particle comprises one or more structures selected from pores, pits, craters, nanowires, cones, pinnacles, hoodoos, coral, cords, walls, fins, ridges, crags, pyramids and inverted pyramids (e.g., on the surface thereof), wherein the diameter of the powder particle is between 0.01 and 10,000 microns, and wherein at least a portion of the particle crystal lattice is altered relative to an otherwise identical particle that is not functionalized with the one or more structures. In some embodiments, at least a portion of the particle crystal lattice is expanded and/or contracted isotropically. In certain embodiments, at least a portion of the particle crystal lattice is expanded and/or contracted anisotropically. In some embodiments, the particle crystal lattice is anisotropically expanded and/or contracted by at least 0.1% along the <111> and/or <311> crystallographic directions relative to an otherwise identical particle that is not functionalized with the one or more structures. In certain embodiments, the band structure is altered for at least a portion of the particle, relative to an otherwise identical particle that is not functionalized with the one or more structures. Any suitable particle provided herein is optionally utilized.

Provided in some embodiments herein is a method of altering the band structure of at least a portion of a particle, the process comprising providing one or more structures selected from pores, pits, craters, nanowires, cones, pinnacles, hoodoos, coral, cords, walls, fins, ridges, crags, pyramids, and inverted pyramids (e.g., on the surface thereof) to the surface of the particle (e.g., according to a process of any one of the claims), wherein the diameter of the powder particle is between 0.01 and 10,000 microns, and wherein at least a portion of the particle crystal lattice is expanded and/or contracted isotropically or anisotropically relative to an otherwise identical particle that is not functionalized with the one or more structures. In certain embodiments, the particle crystal lattice is anisotropically expanded and/or contracted by at least 0.1% along the <111> and/or <311> crystallographic directions relative to an otherwise identical particle that is not functionalized with the one or more structures. Any suitable particle provided herein is optionally utilized.

Provided in some embodiments herein is a kit (e.g., for lysing one or more cell within a chamber thereof) comprising a vessel and one or more functionalized crystalline, polycrystalline, semi-crystalline, or amorphous semiconductor or insulator powder particle, wherein the powder particle (e.g., optionally) comprises one or more structures selected from pores, pits, craters, nanowires, cones, pinnacles, hoodoos, coral, cords, walls, fins, ridges, crags, pyramids, and inverted pyramids, and wherein the diameter of the powder particle is between 0.01 and 10,000 the vessel comprising a chamber, the one or more functionalized particles being configured within the chamber. In certain embodiments, provided herein is a vessel (e.g., for lysing one or more cell within a chamber thereof) comprising a chamber, the chamber comprising an inner surface or another functional surface, the vessel comprising one or more functionalized crystalline, polycrystalline, semi-crystalline, or amorphous semiconductor or insulator powder particle (e.g., embedded) in or on the surface thereof, wherein the powder particle (e.g., optionally) comprises one or more structures selected from pores, pits, craters, nanowires, cones, pinnacles, hoodoos, coral, cords, walls, fins, ridges, crags, pyramids, and inverted pyramids, and wherein the diameter of the powder particle is between 0.01 and 10,000 In some embodiments, the crystalline, polycrystalline, semi-crystalline, or amorphous powder particle is an elemental or compound crystalline, polycrystalline, semi-crystalline or amorphous powder particle selected from group-IVA elements, groups-IV-VI compounds, groups II-IVB compounds, groups I-VII compounds, groups II-VI compounds, groups III-V compounds, groups IV-IV compounds, transition metal oxides, and compounds comprising three or more elements. In certain embodiments, the particle further comprises a film coating, chemical functionalization, a dopant, a nanoparticle decoration, or a surface termination. In some embodiments, the functionalized particle is configured in the surface of the vessel. In certain embodiments, the functionalized particle is not embedded within another material or surface thereof, such as in loose powder form. In some embodiments, the functionalized particle mechanically binds, chemically binds, interacts, or reacts with elements, compounds, molecules, and particles. In certain embodiments, the functionalized particle extracts contaminants from a fluid or gas, catalysis or enhancement of chemical reactions, lysing of cells, removal of microorganisms from a fluid or gas, or any combination thereof.

In some embodiments, provided herein is a bulk composite (e.g., of an article) comprising one or more functionalized crystalline, polycrystalline, semi-crystalline, or amorphous semiconductor or insulator powder particle (e.g., the bulk comprising one or more particle being configured below the surface thereof), wherein the powder particle optionally comprises one or more structures selected from pores, pits, craters, nanowires, cones, pinnacles, hoodoos, coral, cords, walls, fins, ridges, crags, pyramids, and inverted pyramids, and wherein the diameter of the powder particle is between 0.01 and 10,000 In certain embodiments, the crystalline, polycrystalline, semi-crystalline, or amorphous powder particle is an elemental or compound crystalline, polycrystalline, semi-crystalline, or amorphous powder particle selected from group-IVA elements, groups-IV-VI compounds, groups II-IVB compounds, groups I-VII compounds, groups II-VI compounds, groups III-V compounds, groups IV-IV compounds, transition metal oxides, and compounds comprising three or more elements. In some embodiments, the powder particle comprises one or more crystal grains. In certain embodiments, the powder particle consists of a single crystal grain. In some embodiments, the diameter of the powder particle is between 0.1 and 1,000 In certain embodiments, the powder particle comprises two or more structures selected from pores, pits, craters, nanowires, cones, pinnacles, hoodoos, coral, fins, ridges, crags, pyramids, and inverted pyramids. In some embodiments, the one or more particle structures are submillistructures. In certain embodiments, the one or more particle structures are selected from microstructures and nanostructures. In certain embodiments, the mean diameter of the smallest 30% of powder particles is 200% smaller than the mean diameter of the largest 10% of powder particles. In some embodiments, the surface thereof is antireflective, reflective, adsorbing, conductive, insulating, antistatic, luminescent, antimicrobial, omniphobic, hydrophobic, hydrophilic, antifouling, non-stick, non-slip, or any combination thereof. In certain embodiments, the bulk is antistatic, light absorbing, light reflecting, antimicrobial, conductive, insulating, electrically resistive, photoluminescent, or any combination thereof. In some embodiments, at least a portion of the bulk material is removed exposing at least a portion of one or more functionalized particle (e.g., or the functionalized particle in the bulk is otherwise exposed to or on a surface of the bulk material).

In certain embodiments, any submillistructure provided herein has a dimension of less than 500 µm, less than 200 µm, less than 150 µm, less than 100 µm, less than 50 µm, or the like; and, e.g., having a dimension of at least 1 nm, at least 2 nm, at least 5 nm, at least 25 nm, at least 50 nm, at least 100 nm, or the like.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows a top-down view of the heterofunctionalized particle, and FIG. 2B is a magnified view of FIG. 2A. FIG. 2C shows a magnified view of a pit, shown in FIG. 2B, and shows the pore structure within the pit.

FIG. 3B is a magnified view of FIG. 3A.

FIG. 5A shows a functionalized power particle as imaged by SEM. FIG. 5B shows a magnified view of a functionalized powder particle as imaged by SEM. Irregular interconnected structures of the hoodoos can be seen. FIG. 5C shows a magnified top-down view of the irregular interconnected hoodoo structure as imaged by SEM. FIG. 5D shows a cross-sectional view of the functionalized powder particle comprising hoodoo nanostructures at the surface. Thin Pt coating is seen on the structures in the foreground.

FIG. 6A shows a porous nanowire, and FIG. 6B shows a nanowire with smaller secondary nanowires extending outward from the primary nanowire. The structures and features are not drawn to scale.

FIG. 9A shows functionalized powder particles on the surface of a binder or adhesive on a substrate or bulk medium. FIG. 9B depicts functionalized powder particles fully embedded in a substrate or bulk medium. FIG. 9C shows functionalized powder particles embedded and at the surface of a substrate or bulk medium. The structures and features are not drawn to scale. The configurations are not limiting.

FIGS. 13A-13C show SEM images of nanoparticles decorating the surface of functionalized powder particles. FIG. 13A shows an SEM image of Ag nanoparticles decorating a pitted surface of a functionalized powder particle prepared via Ag-MACE of Si crystalline particles. FIG. 13B shows an SEM image of a Si powder particle comprising pores and Ag nanoparticles. FIG. 13C shows an SEM image of Si powder particle comprising pores and Ag nanoparticles. The pores seen in FIG. 13C are smaller than in FIG. 13B and the Ag nanoparticles in FIG. 13C are larger than in FIG. 13B.

FIG. 16A shows a particle comprising coral structures, FIG. 16B shows a magnified top-down view of the coral structure seen in FIG. 16A, and FIG. 16C shows an edge view of the coal structure seen in FIG. 16B. The angle of observation shows the rough and complex coral structure. The images demonstrate the complex coral texture and interconnected structures that are formed.

FIG. 17A shows the irregular coral structures and FIG. 17B shows a cross-sectional view of the coral structure seen in FIG. 17A.

FIGS. 19A-19C show SEM images of examples of heterofunctionalized particle morphologies comprising pore and pit nanostructures. FIG. 19A shows a morphology comprising triangular-aperture pits and pores. The functionalized Si crystalline particle was synthesized via Ag-MACE and subsequently nitric acid etching. FIG. 19B shows square-aperture pores in a pit. The morphology was prepared via Cu-MACE. FIG. 19C shows a fine porous surface with triangular-aperture inverted pyramids. The morphology was synthesized via Cu-MACE.

FIG. 20A shows a morphology comprising triangular aperture inverted pyramids on the surface of a pit. FIG. 20B shows a morphology comprising micro- and nano-scale inverted pyramid structures. FIG. 20C shows a morphology comprising convex structures formed from intersecting inverted pyramid structures.

FIG. 22A shows a side view of the morphology and FIG. 22B shows a magnified top-down view of the pyramid structures.

FIGS. 24A-24B show SEM images of the surface of functionalized SiC particles (40 µm average diameter) that prepared via CE etched comprising HF and $HNO_3$ (3:1 v/v). FIG. 24A shows a morphology comprising intersecting fin structures and FIG. 24B shows a top-down view of a morphology comprising wall structures.

FIG. 27A shows average contact angle measurement results. The Sample 1 coating comprises functionalized Si particles prepared via the method discussed in Example 11, Sample 2 comprises functionalized Si particles prepared via the method discussed in Example 2, Sample 3 comprises functionalized Si particles prepared via the method discussed in Example 7, Sample 4 comprises functionalized SiO particles prepared via the method discussed in Example 13, and Sample 5 comprises nonfunctionalized Si particles (45 µm average diameter). FIG. 27B shows an example profile view of a DI-$H_2O$ drop on the Sample 3 surface.

FIG. 30A shows a vessel containing functionalized particles, FIG. 30B shows solution containing cells added to the vessel from FIG. 30A, and FIG. 30C shows agitation of solution containing cells and functionalized particles. Cells in solution were lysed from the interaction with the functionalized particles. FIG. 30D shows the extraction of the solution that contains cellular components. The design of the method is not limited to this depiction. The features and structures are not drawn to scale.

FIG. 31 shows the percent reduction of viable bacteria cells via standard plate counts following lysis protocol described in Example 25. Treatments (A) and (B) comprise structurally functionalized powder particles, (C) comprises nonfunctionalized Si powder particles (45 µm average diameter), and (D) comprises no powder, as a control. The initial bacteria culture population was 5.3×10$^8$ per mL and the method is illustrated in FIG. 30.

FIG. 32 shows a table of the etch depth of functionalized particles prepared via Ag-MACE for different etching durations and stirring speeds. The etch depths were determined via focused ion beam (FIB) cross sectioning and SEM. The data demonstrates the effect of stirring speed and etching time on the etching depth of functionalized Si particles that were prepared by otherwise identical conditions.

FIG. 33A shows coral structures, FIG. 33B is a magnified view of the structures shown in FIG. 33A, FIG. 33C shows hoodoo structures, and FIG. 33D is a magnified view of the structures shown in FIG. 33C.

FIG. 36B shows a magnified view of the structures shown in FIG. 36A.

Sample (E) is an ABS plastic substrate coated with heterofunctionalized Si particle comprising pits and pores prepared via method described in Example 2. Sample (F) is an ABS plastic substrate coated with nonfunctionalized Si particles (45 µm average diameter). The particle surfaces of samples (C), (E), and (F) have the same chemical composition and crystal structure as sample (A). The different surface morphologies result in different light reflectance spectra.

FIGS. 38A-38D show an optical photo of surfaces of samples (A), (B), (C) and (D), respectively. Sample (A) is a bare ABS plastic substrate, and samples (B), (C), and (D) are coated ABS plastic substrates that were prepared via method described in Example 16. Sample (B) is coated with heterofunctionalized Si particle comprising pits and pores prepared via method described in Example 2. Sample (C) is coated with functionalized amorphous SiO particles prepared via method described in Example 13. Sample (D) is coated with functionalized Si particles prepared via method described in Example 11.

DETAILED DESCRIPTION OF THE INVENTION

Methods of Functionalizing a Particle

Figure 14:
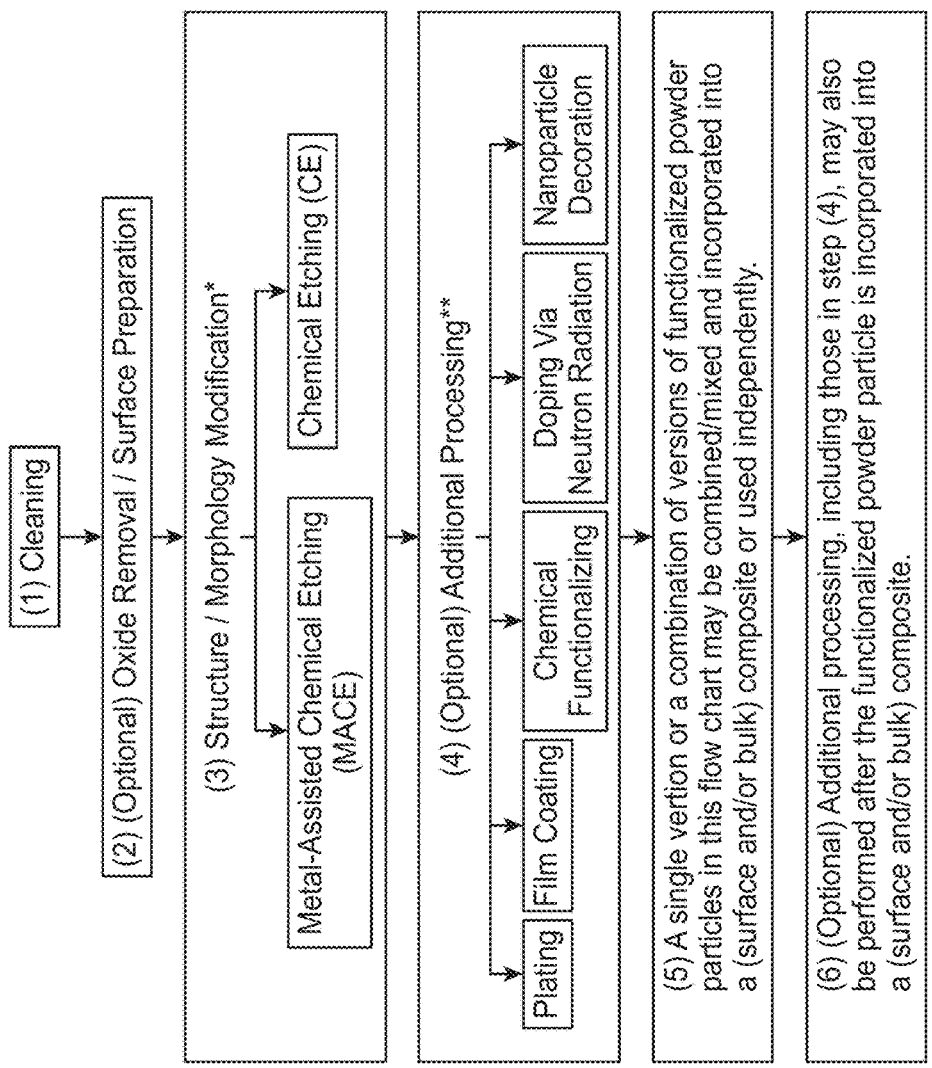
FIG. 14 depicts a proposed process schematic for the synthesis and application of functionalized powder particles.
Figure 15:
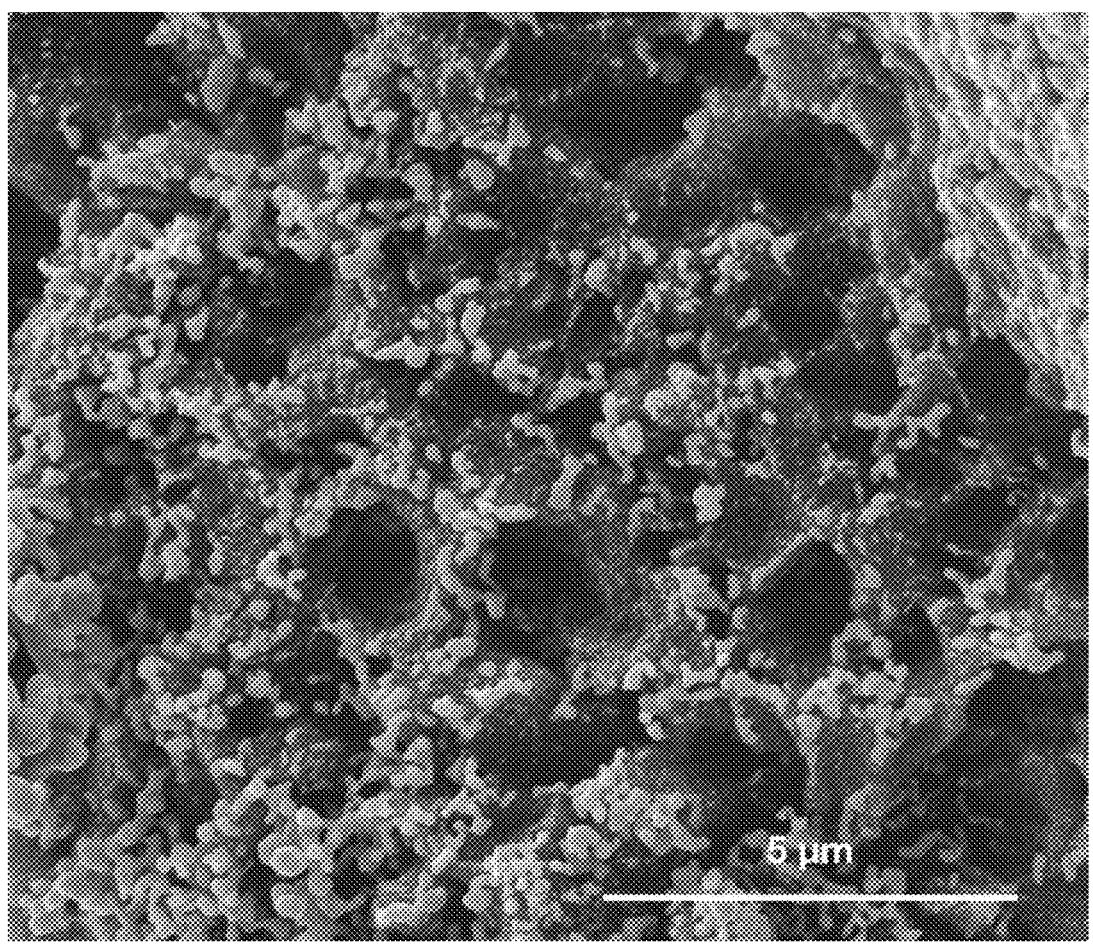
FIG. 15 shows a SEM image of a functionalized particle comprising pits and pores that is decorated with Cu nanoparticles. The particle was prepared via Cu-MACE of Si crystalline particles.

In some aspects, the present disclosure provides a method of forming structures on a powder particle. FIG. 14 provides a conceptual schematic of an exemplary method of forming structures on a powder particle. In some embodiments, the method comprises (a) providing one or more (e.g., crystalline, polycrystalline, semi-crystalline or amorphous) (e.g., semiconductor or insulator) powder particle; (b) (e.g., optionally), removing surface contaminants from the one or more powder particle; (c) (e.g., optionally), removing oxides from the one or more powder particle; (d) forming a (e.g., first type of) structure on the one or more powder particle, thereby forming one or more homofunctionalized powder particle; and (e) (e.g., optionally), forming a (e.g., second type of) structure on the one or more homofunctionalized powder particle, thereby forming one or more heterofunctionalized powder particle; wherein the first and the second types of structures are (e.g., optionally) selected from the group consisting of pores, pits, craters, nanowires, cones, pinnacles, hoodoos, coral, cords, walls, trenches, fins, ridges, crags, pyramids, and inverted pyramids.

In some aspects, the present disclosure provides a method of forming structures on a powder particle, the method comprising providing one or more (e.g., crystalline, polycrystalline, semi-crystalline or amorphous) (e.g., semiconductor or insulator) powder particle; and forming a (e.g., first type of) structure on the one or more powder particle, thereby forming one or more homofunctionalized powder particle. The (e.g., first type of) structure may be selected from the group consisting of pores, pits, craters, nanowires, cones, pinnacles, hoodoos, coral, cords, walls, trenches, fins, ridges, crags, pyramids, and inverted pyramids.

In some aspects, the present disclosure provides a method of forming structures on a powder particle, the method comprising (a) providing one or more (e.g., crystalline, polycrystalline, semi-crystalline or amorphous) (e.g., semiconductor or insulator) powder particle; (b) removing surface contaminants from the one or more powder particle; (c) (e.g., optionally), removing oxides from the one or more powder particle; (d) forming a (e.g., first type of) structure on the one or more powder particle, thereby forming one or more homofunctionalized powder particle; and (e) forming a (e.g., second type of) structure on the one or more homofunctionalized powder particle, thereby forming one or more heterofunctionalized powder particle; wherein the first and/or the second types of structures are (e.g., optionally) selected from the group consisting of pores, pits, craters, nanowires, cones, pinnacles, hoodoos, coral, cords, walls, trenches, fins, ridges, crags, pyramids, and inverted pyramids.

The powder processing methods described herein differ substantially from typical methods used to functionalize wafers or other substrates. The increased surface area of a powder relative to other substrates may alter the reaction characteristics, including reaction rates and chemical and particle dynamics of a functionalization reaction. In some examples, the chemical reaction used to create nanostructures on the surface of a powder particle may increase the solution temperature due to the reaction exotherm and rapid kinetics, which may alter the reaction rates. By contrast, the same reaction on a wafer may produce a negligible change in solution temperature due to the low surface area of the wafer. The exposed crystallographic planes or junctions may influence the functionalization process and resulting morphology. In some examples, the particle form factor provides a greater number and diverse selection of exposed crystallographic planes or junctions as compared to wafers. Stirring or agitating the reaction solution impacts the chemical reaction differently between powders and wafers and may result in different functionalization. In some examples, the powder is in motion through the solution, which may change the migration of catalyst nanoparticles within the powder particle and/or the dissolution of material from the powder. Different morphologies may be formed due to the differences in catalyst dynamics as a result of the differences in the motion between powder particles and wafers.

The methods described herein may be performed at room temperature and atmospheric pressure. In some embodiments, the pressure and temperature may be adjusted to alter the structure and morphology present on the surface of a powder particle. The reactions described herein may be performed in an open or closed reaction vessel.

Powder Particles

A powder particle of the present disclosure may be crystalline, polycrystalline, semi-crystalline, or amorphous. Preferably, the powder particle is crystalline or amorphous. The particle may be solid or it may comprise pores, and it may be regular or irregular in shape. The powder particle may be an elemental or compound crystalline particle. Preferably, the powder particle is selected from the group consisting of group-IVA elements, groups-IV-VI compounds, groups II-IVB compounds, groups I-VII compounds, groups II-VI compounds, groups III-V compounds, groups IV-IV compounds, transition metal oxides, and compounds consisting of three or more elements. The powder particle may be composed of a semiconducting or insulating element or compound, such as Si, Ge, Sn, CuCl, CaO, MgO, GaAs, GaN, BN, BP, AlN, InN, InP, SiO, and SiC.

A powder particle of the present disclosure may comprise one or more crystal grains. Optionally, the particle consists of a single crystal grain. The powder particle may also consist of 2, 3, 4 or more crystal grains held in close physical contact. The powder particle may have an irregular shape but will have an average effective diameter based upon the longest and shortest aspects of the particle. The average effective diameter of the particle may be between 0.01 µm and 10,000 µm, such as between 0.1 µm and 10,000 µm or between 0.1 µm and 1,000 µm. The average effective diameter of the particle may be at least about 0.01 µm, 0.1 µm, 1 µm, 10 µm, 100 µm, 1,000 µm, 10,000 µm or more. The average effective diameter of the particle may be no more than about 10,000 µm, 1,000 µm, 100 µm, 10 µm, 1 µm, 0.1 µm, 0.01 µm or less. Optionally, the average effective diameter of the powder particle may be between 0.1 µm and 100 µm, 0.1 µm and 10 µm, 1 µm and 10,000 µm, 1 µm and 1,000 µm, 1 µm and 100 µm, 10 µm and 10,000 µm, 10 µm and 1,000 µm, or between 100 µm and 10,000 µm. The average effective diameter and dispersity of powder particle sizes may be selected based upon the application and the desired properties of the modified particle.

A group of powder particles may have a characteristic size dispersity. A size dispersity may be monomodal, bimodal, trimodal, or multimodal. A size dispersity may be determined based upon a characteristic size of the powder particles, e.g., average diameter. A powder size dispersity may be determined by sieve sizing of powder particles. The size dispersity of powder particles may be determined such that about 10%, 20%, 30%, 40%, 50%, 60%, 70%, 80%, 90%, or 95% of the particles are within 50% of the average size of the particle. The size dispersity of particles may be determined such that at least about 10%, 20%, 30%, 40%, 50%, 60%, 70%, 80%, 90%, or 95% or more of the particles are within 50% of the average size of the particle. The size dispersity of particles may be determined such that no more than about 95%, 90%, 80%, 70%, 60%, 50%, 40%, 30%, 20%, or 10% of particles are within 50% of the average size of the particle. A particular characteristic particle size dispersity may be correlated to certain physical properties of the functionalized powder material.

Pre-Etching Preparation

Prior to forming structures on a powder particle, it may be advantageous to remove surface contaminants from one or more powder particle. Surface contaminants may include any organic or inorganic gas, liquid or solid other than the desired material located on the surface of the powder particle. The powder particle can be placed in a series of baths or solutions with one or more solvents. Optionally, the one or more powder particle is placed in a solvent bath, e.g., an acetone bath for at least 10 minutes. The powder particle may further be placed in a second solvent bath, e.g., methanol or ethanol bath for at least 10 minutes. Removing surface contaminants from the powder particle may comprise ultrasound sonication. In some embodiments, surface cleaning can be performed by immersing the powder is an acid bath or an acid bath augmented with an oxidizer, which may be conducted at room or elevated temperatures. Each bath may include additional consecutive treatments. For example, an acetone or ethanol bath may involve at least 10 minutes of stirring followed by at least 10 minutes of ultrasound sonication. In some embodiments, the powder particle may be placed in a solvent solution where both stirring and ultrasound sonication is performed simultaneously, to keep the powder suspended, for at least 10 minutes. In some embodiments, surface contaminants may also be removed from the one or more powder particle via prolonged heating at temperatures exceeding 20° C., 30° C., 40° C., 50° C., 60° C., 70° C., 80° C., 90° C., 100° C., 200° C., 300° C., 400° C., 500° C., 600° C., 700° C., 800° C., 900° C., 1000° C., or more. The heating may occur under one or more different gaseous environments. In some embodiments, the one or more powder particle may be heated under a vacuum with a pressure below 100 mbar. The powder particle may also be heated in a gaseous environment comprising air, $N_2$, $CO_2$, e, $H_2$, Ar or a mixture thereof.

A method of the present disclosure may also comprise removing oxides from one or more powder particle. The one or more powder particle may be washed in an acidic or basic solution. For example, the powder particle may be washed in a bath comprising a mixture of HF (>1M) and deionized $H_2O$ (DI-$H_2O$) for at least 5 minutes duration. In some embodiments, the bath may be buffered through the addition of $NH_4F$ to the HF solution. In some embodiments, the bath may be illuminated to photo-assist the dissolution of oxides and other surface atoms. The wavelength and intensity of the light may be varied depending upon the chemical nature of the powder particle. The powder particle may be rinsed with a rinsing agent (e.g., DI-$H_2O$) after a chemical bath. The bathed powder particle may be dried and flushed with a gas. The flush gas may comprise $N_2$, He, $H_2$ or another gas depending upon the desired surface chemistry. The powder particle may be thermally annealed following a bath preparation in order to reconfigure the surface atoms and evaporate residual surface moisture. In some embodiments, thermal annealing can be substituted for the above-described bath method. The powder particle may be soaked in an ion-rich solution after bathing or thermal annealing. The ion species is chosen to alter the surface chemistry as desired for the chosen application of the particles. In some embodiments, the ion-rich solution bath may be followed by a thorough rinse with a rinsing agent (e.g., DI-$H_2O$).

Etching Methods

Methods described herein typically comprise forming a first type of structure on the one or more powder particle, thereby forming one or more homofunctionalized powder particle. In some embodiments, a method may further comprise forming a second type of structure on the one or more homofunctionalized powder particle, thereby forming one or more heterofunctionalized powder particle. The forming may comprise forming a structure on a surface or within a pore of a powder particle. The method of forming may be selected based on the desired bulk structure and surface morphology of the powder. The particular structural modification may involve single or multi-process etching via plasma, gas or solution methods. For example, a method of creating functionalized powder particles may comprise a repeated sequence of metal-assisted chemical etching (MACE) followed by chemical etching (CE). Optionally, MACE may be performed several times consecutively without any CE. Optionally, CE may be performed followed by MACE. The sequencing of various etching methods may be altered to create differing morphologies of surface structures. The powder particles may be rinsed in a rinsing agent (e.g., DI-$H_2O$), flushed with a gas such as $N_2$, He or $H_2$, and/or thermally annealed following any etching method to remove any surface debris. Optionally, the particles may be rinsed in a solvent, such as methanol, ethanol or acetone.

Metal-assisted chemical etching (MACE) typically involves two main steps, 1) deposition of metal nanoparticles on a powder surface and 2) etching in an acidic or basic bath. The two steps may be performed simultaneously, optionally in a single vessel. Optionally, the deposition and etching processes may be performed separately. When separated, the deposition of metal nanoparticles may be performed once or multiple times prior to etching. Etching may be performed once or multiple times. Optionally, the solution may be stirred or agitated through use of a magnetic stir bar, overhead stirrer, circulation pump, impeller, or other mixing or agitating apparatus.

Deposition of metal nanoparticles on the powder particles for a MACE process may occur in a solution comprising an acid or base, DI-$H_2O$ and metal ions, such as (e.g., noble metal or precious metal) ions. For example, HF may be used with a concentration of at least 0.1 M. One or more species of metal ions can be used, including, for example, Ag. Noble metal salts, such as $AgNO_3$, can be used to introduce metal ions into the bath. In some embodiments, other metal salts may be substituted for or used in concert with $AgNO_3$, including, but not limited to $Fe(NO_3)_3$, $Cu(NO_3)_2$, $H_2PtCl_6$, $K_2PtCl_6$, $HAuCl_4$, or $RhCl_3$. Metal ions can be introduced into the bath solution by other methods including electrolysis. The solution temperature, duration, stirring and agitation rates, pH, chemical composition, volume, metal ion concentrations and base or acid concentrations can be adjusted to control the size and surface coverage of nanoparticle deposition. If two or more species of metal ions are to be deposited on the powder particle surface, they can be deposited simultaneously or in separate steps at identical or differing surface concentrations. In some embodiments, the solution may be illuminated to alter the deposition behavior of the metal nanoparticles. The wavelength and intensity of the light may be varied depending upon the physical and chemical nature of the one or more powder particle. The powder particle may be thermally annealed after MACE to alter the surface coverage of metal nanoparticles.

Alternatively, MACE can be performed in a solution comprising an acid or base, an oxidizing species and $DI-H_2O$. In some embodiments, $DI-H_2O$ may be replaced in part or in full by another solvent, such as methanol, ethanol, isopropyl alcohol or acetone. For example, HF may be chosen as an acid, preferably at a concentration above 4 M, and $H_2O_2$ may be chosen as an oxidant. In some embodiments, HF may be substituted with another acid, for example, $H_3PO_4$ or HCl, or with a base, for example, $NH_4F$. The oxidizing species may be selected from $H_2O_2$, $O_2$ gas, ozone, $H_2SO_4$, $H_2S_2O_8$, NaClO, $NaClO_4$, $KMnO_4$ and $Fe(NO_3)_3$. Optionally, the reagents may be added to the solution over a period of time. The acid or base concentration, oxidant concentration, solution duration, stirring and agitation rates, pH, chemical composition, volume, rate of chemical addition, and temperature may be varied to control the structure and morphology of etching performed on the powder particle surface. In some embodiments, the solution may be illuminated to alter the dissolution of the particle. The wavelength and intensity of the light may be varied depending upon the physical and chemical nature of the one or more powder particle and the desired surface structures and morphologies. Excess metal nanoparticles may be removed from the powder particle surface. For example, a solution of $HNO_3$ and $DI-H_2O$ can be used to remove the metal from the particle surface. In some embodiments, metals may be removed from the surface of particles using an acidic solution, e.g., sulfuric acid, perchloric acid, or aqua regia. In some embodiments, metal nanoparticle removal may be achieved with an electrochemical method, a suitable chemical method, or a combination of both methods. In some embodiments, the removed metal nanoparticles may be recovered and recycled for further use.

In practicing any of the subject methods, chemical etching (CE) of the one or more powder particle may preclude, precede or follow metal-assisted chemical etching. CE typically comprises any method for selectively removing surface material using a primarily chemical, non-mechanical means. A CE step may be performed once or multiple times in the subject methods. A CE method may involve an acid or base solution with the treated powder particle. For example, the CE bath may comprise KOH and $DI-H_2O$. In some embodiments, the KOH may be substituted with an acid or base species such as $NH_4F$, HF, NaOH, LiOH, RbOH, CsOH, $NH_4OH$, $Sr(OH)_2$, $Ca(OH)_2$, $Ba(OH)_2$, tetramethylammonium hydroxide, or HBr. The chemical concentrations, solution temperatures, durations, stirring and agitation rates, pH, chemical composition, volume, rate of chemical addition, may be varied depending upon the desired surface structures and morphologies. In some embodiments, the solution may be illuminated to enhance the surface dissolution of the powder particle. The wavelength and intensity of the light may be varied depending upon the physical and chemical nature of the one or more powder particle.

Additional Processing

Following the formation of one or more structures on one or more powder particle, the resultant homo- or heterofunctionalized powder particle may be subjected to one or more additional processes. Any combination of the optional additional processes described below may be performed, in any order and repeated any number of times. In some examples, any additional processing is performed prior to incorporating the functionalized powder particle into an article. Alternatively, any additional processing may be performed after incorporating the functionalized powder particle into an article.

An additional processing method may comprise a method of film coating or plating one or more powder particle. The film coating or plating method may include any process that results in a uniform, semi-uniform, non-uniform or patterned deposition of a thin layer of material over the entire surface or a portion of the surface of the powder particle. For example, vapor deposition may be used to deposit a thin film. In some embodiments, a chemical bath, an electrochemical method, spin coating, dip coating, spraying, roll-to-roll coating or lithography method may be used.

Another additional processing method may comprise a method of chemically functionalizing the surface of one or more powder particle. Chemical functionalization may include any process that creates reactive or non-reactive sites on the surface of one or more powder particle. For example, the surface of a powder particle may be bonded with an active antimicrobial chemical such as chlorhexidine digluconate or (3-aminopropyl) triethoxysilane. Alternatively, the surface of the particle may be functionalized through a reaction with a functionalizing compound, e.g., silane compounds, to include but not limited to octadecyltrichlorosilane or 1H,1H,2H,2H-perfluorodecyltriethoxysilane to produce highly hydrophobic surfaces which can also improve the bonding of the particle to substrates. In some embodiments, the surface may be functionalized with dispersants or peptides. In some embodiments, the surface of the particle may be functionalized to aid in the particle binding or adhering to an article or medium. For example, diethoxydiphenylsilane, allyltrichlorosilane, triethoxy-p-tolylsilane, allyltriethoxysilane, vinyltrimethoxysilane, or other derivatized silanes, may be used to bind the particle in a polymer medium through either covalent or non-covalent interactions. The powder particle surfaces may also be functionalized with more than one chemical species depending upon the desired material properties for a chosen application. Chemical functionalization may comprise methods for altering properties such as surface energy, surface area, surface roughness, density profile, refractive index, optical constant, electrostatic charge, bandgap, shear modulus, plasticity, specific weight, coefficient of friction, acoustic properties, thermal properties, optical properties, electrical properties, chemical properties, non-covalent interactions, photoluminescence, photo absorption, hydrophobicity and hydrophilicity.

Another additional processing method may comprise a method of doping one or more powder particle via neutron irradiation. The exposure of a powder particle to neutron radiation may alter its electronic properties, band structure, or its bandgap. Submillistructures created via methods such as MACE may be sensitive to the doping of the semiconductor particle. In some examples, nanostructure formation followed by neutron irradiation may allow particular structures and morphologies to be enhanced with desirable electronic properties.

Another additional processing method may comprise the decoration of one or more powder particle with nanoparticles, as shown in FIGS. 12A-12B, 13A-13C, and 15. The nanoparticles may be deposited or dispersed on the surface of the functionalized powder particle by any method of nanoparticle synthesis. For example, nanoparticles may be deposited in a chemical bath. In some embodiments, nanoparticles may be deposited by vapor deposition. Nanoparticle decoration may be used to alter and enhance the physical or chemical properties of the powder particle. Nanoparticles may be used to enhance the antimicrobial properties of powder particles. For example, Ag, Cu or ZnO nanoparticles may be added to one or more powder particles for their antimicrobial activity. Nanoparticles such as Ag, Au and Cu may enhance the electrical and optical properties of powder particles. Nanoparticles may decorate the powder particle surfaces to enhance UV light absorption. For example, $Al_2O_3$ or ZnO may enhance the UV absorption characteristics of powder particles. Nanoparticles may also be utilized to protect nanostructures from UV light degradation. For example, $CeO_2$ nanoparticles may be used as a UV protectant.

Structures

Figure 1:
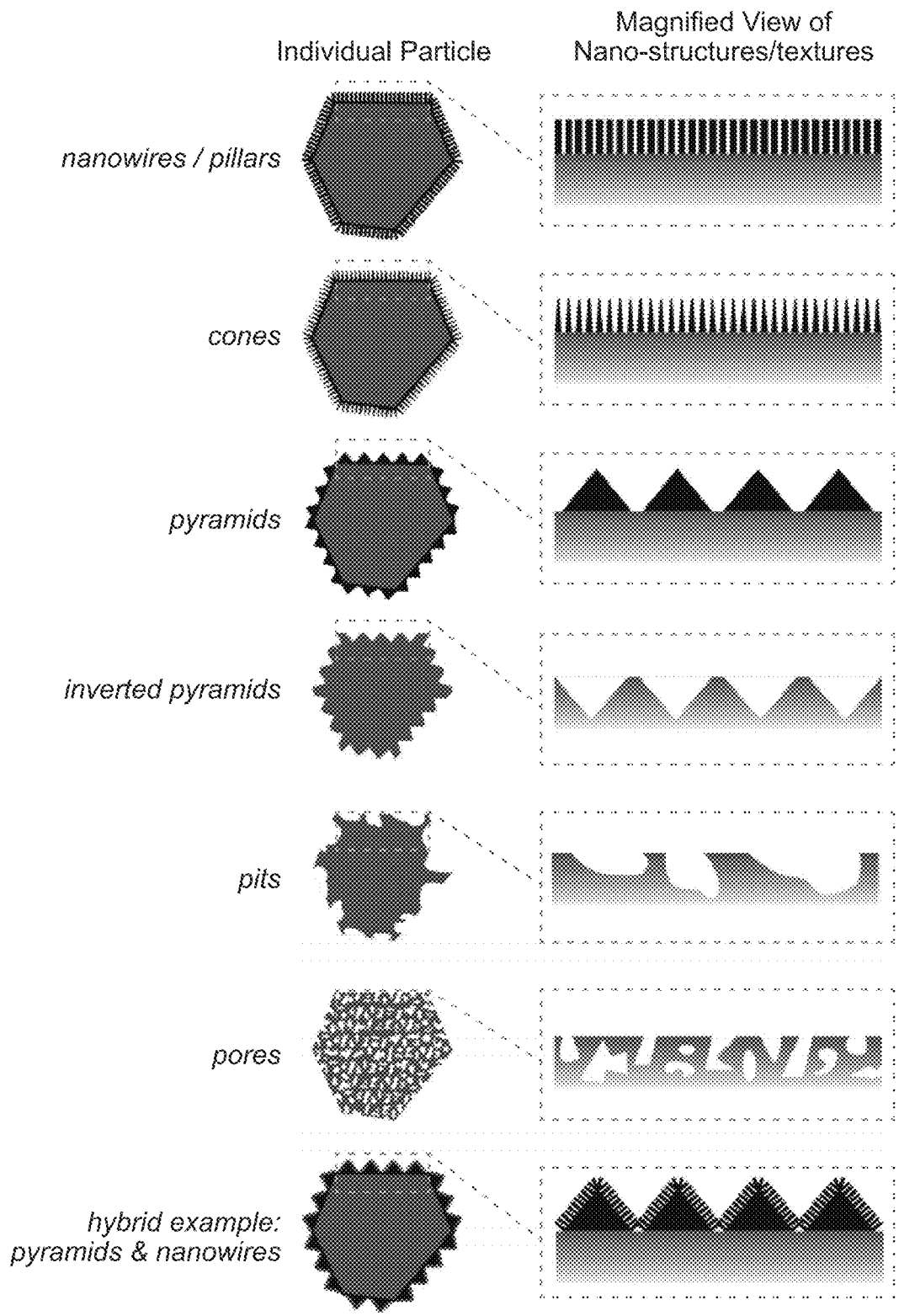
FIG. 1 provides illustrative graphical, cross-sectional representations of structures that may decorate a functionalized powder particle, including nanowires/pillars, cones, pyramids, inverted pyramids, pits, pores, and a hybrid comprising pyramids and nanowires. Structures and particles are not drawn to scale and are not limited to these examples.

The present disclosure provides powder particles comprising structures, methods of forming these structures, and compositions comprising the powder particles. Any structure disclosed herein may refer to a submillistructure, such as a microstructure or a nanostructure. Specific examples of types of structures suitable in the present methods and compositions include, but are not limited to, pores, pits, craters, nanowires, cones, pinnacles, hoodoos, coral, cords, walls, fins, ridges, crags, pyramids, and inverted pyramids. Examples of nanostructures that may decorate a functionalized powder particle are shown in FIG. 1.

Pits, craters, pores refer to indentations on the powder particle. Pits and craters may have a depth-to-diameter ratio of less than 2. The term pore is used to refer to any indentation with a depth-to-diameter ratio of 2 or more. Pores may have two open ends, though this is not required. Pits, craters, and pores may have a geometric or organic shaped aperture. Example images of pits and pores on a particle surface are shown in FIGS. 2A-2C, 3A-3B, and 19A-19C.

Figure 4:
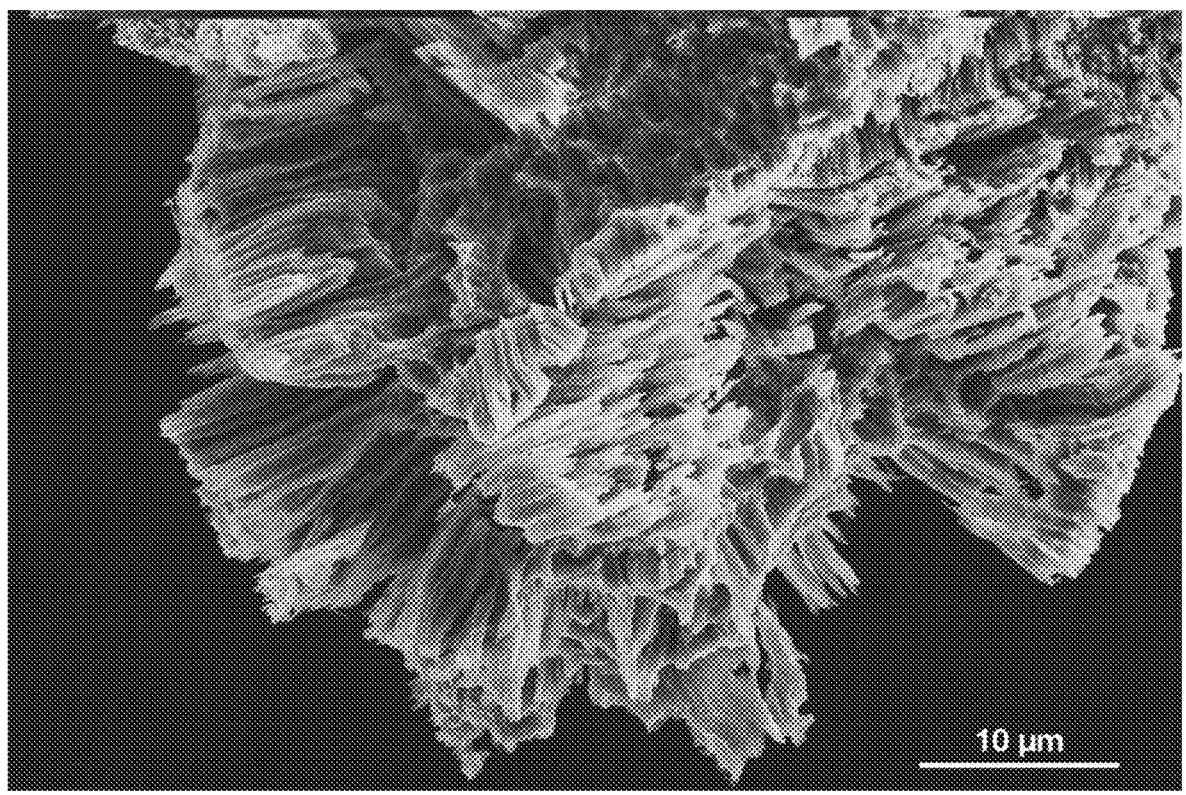
FIG. 4 shows a SEM image of a morphology comprising nanowires. The particles were prepared via Ag-MACE of Si crystalline particles. The nanowires were formed when the etching solution, during Ag-MACE, was static. Sections of the particle are missing nanowires because they were broken off during normal handling.

The terms nanowires, pinnacles and pillars are used interchangeably, and refer to an elongated structure that extends outward from the powder particle. A nanowire or pillar may have a height-to-diameter ratio of 2, 3, 4, 5, 6, 7, 8, 9, 10 or more. A nanowire or pillar may have a circular cross-section, though this is not required. A nanowire or pillar may have a similar average cross-sectional area or a variable cross-sectional area. An example of nanowires and nanopillars on the surface of a powder particle is shown in FIG. 4. The term cone refers to a pillar structure whose cross-sectional area continuously decreases from the base to the tip.

Figure 21:
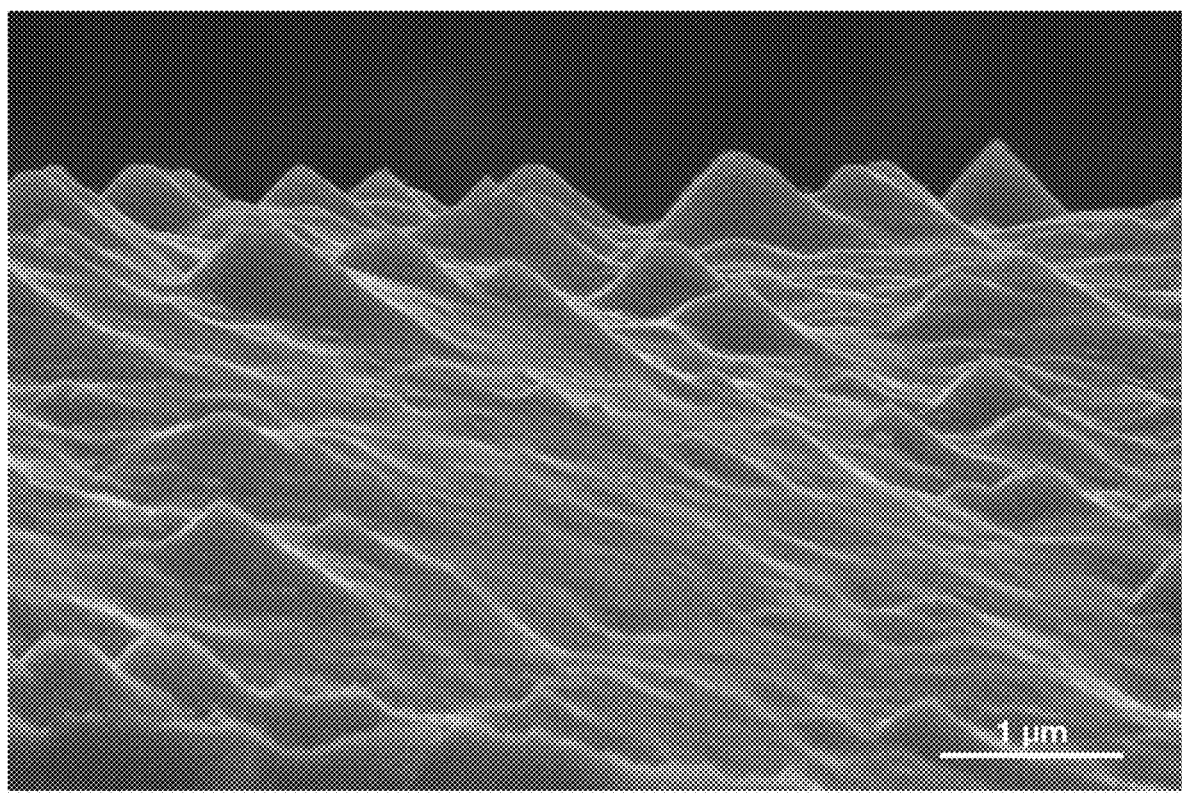
FIG. 21 shows a SEM image of morphologies comprising upright pyramid structures prepared via etching Si particles with 35% (wt/wt) KOH.
Figures 22A, 22B:
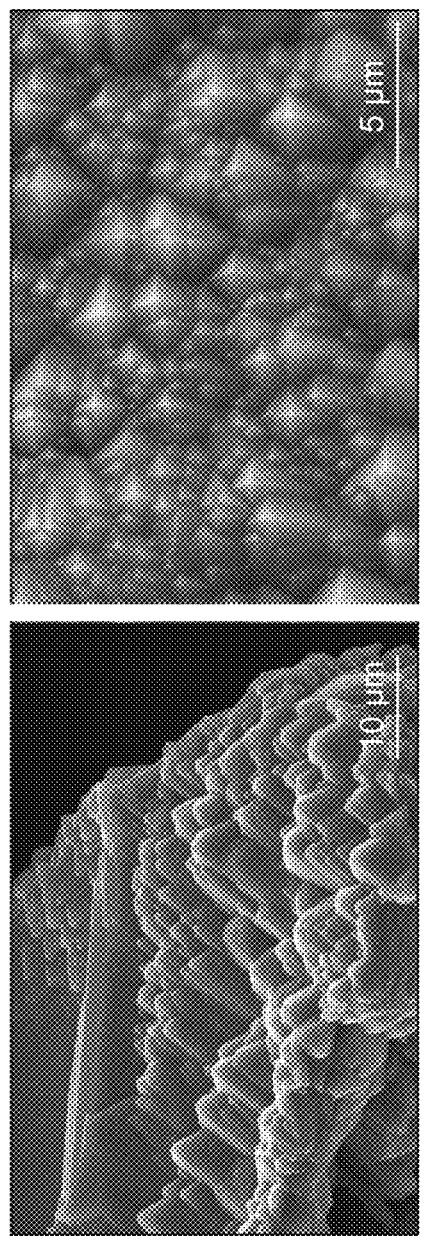
FIGS. 22A-22B show SEM images of morphologies comprising upright pyramid structures prepared via CE etching comprising 5% (wt/wt) NaOH.

The term pyramid refers to any structure that extends outward from the powder particle whose cross-sectional area decreases from the base to the tip and has three or more faces. Pyramid structures may have sharp edges or flat sides, though this is not required. Pyramid structures may be truncated or have a flat tip, though this is not required. Examples of pyramid structures on the surface of a powder particle is shown in FIGS. 21 and 22A-22B.

Figures 20A, 20B, 20C:
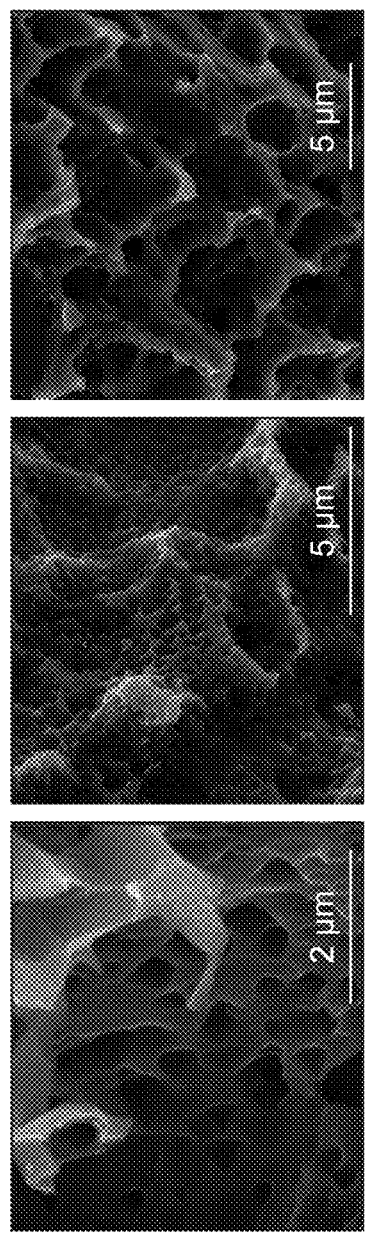
FIGS. 20A-20C show SEM images of morphologies comprising inverted pyramid structures. These morphologies were prepared via Cu-MACE of Si particles.

Inverted pyramids refer to any concaved pyramid structures that extend into the particle whose cross-sectional area decreases from the base to the tip and has three or more faces. Inverted pyramid structures may have flat sides, sharp corners, or a truncated or flat tip, though this is not required. Examples of inverted pyramid structures on the surface of a powder particle is shown in FIGS. 20A-20C.

Figure 23:
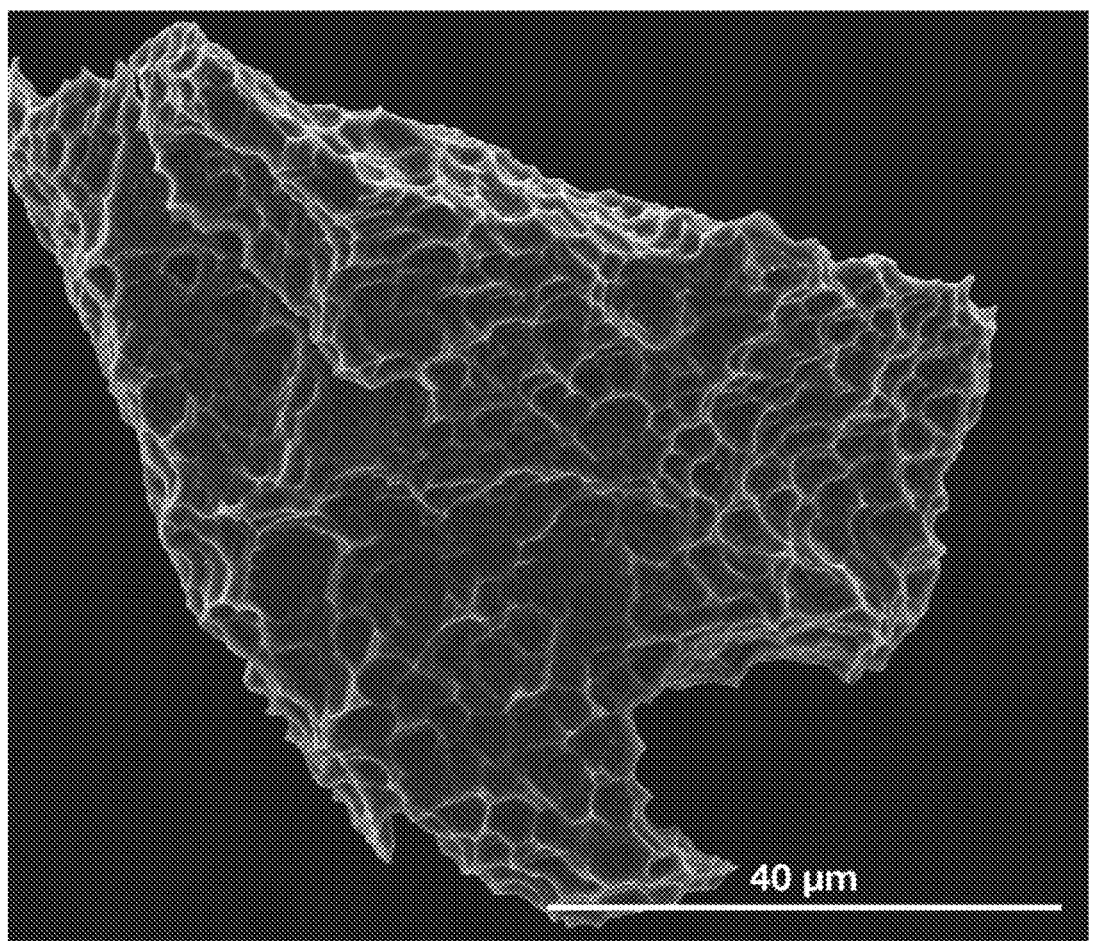
FIG. 23 shows a SEM image of a heterofunctionalized Si particle comprising intersecting ridge morphology produced via heterofuntionalization that comprises sequential etching, first etching with 1% (wt/wt) KOH and subsequently Ag-MACE.

The term ridge or crag refers to a protruding, intersecting structure along its length, whose cross-sectional width at FWHM (full width at half maximum) is sub-micron and is less than its length. The ridge or crag may consist of curved or straight sections along its length. The ridges or crags may form an enclosed, depressed area, though this is not required. An example of ridges or crags on the surface of a powder particle is shown in FIG. 23.

The term walls refer to a protruding structure whose length is greater than its height or cross-sectional width and consists of a similar width to height ratio along its length. The walls may have a constant cross-sectional width from base to top, though this is not required. An example of walls on the surface of a powder particle is shown in FIG. 24B.

The term fins refer to a protruding structure whose length is greater than its height or cross-sectional width that consist of varying heights along its length. The fins may have a cross-sectional area that decreases from base to top, though this is not required. An example of fins on the surface of a powder particle is shown in FIG. 24A.

Figure 35:
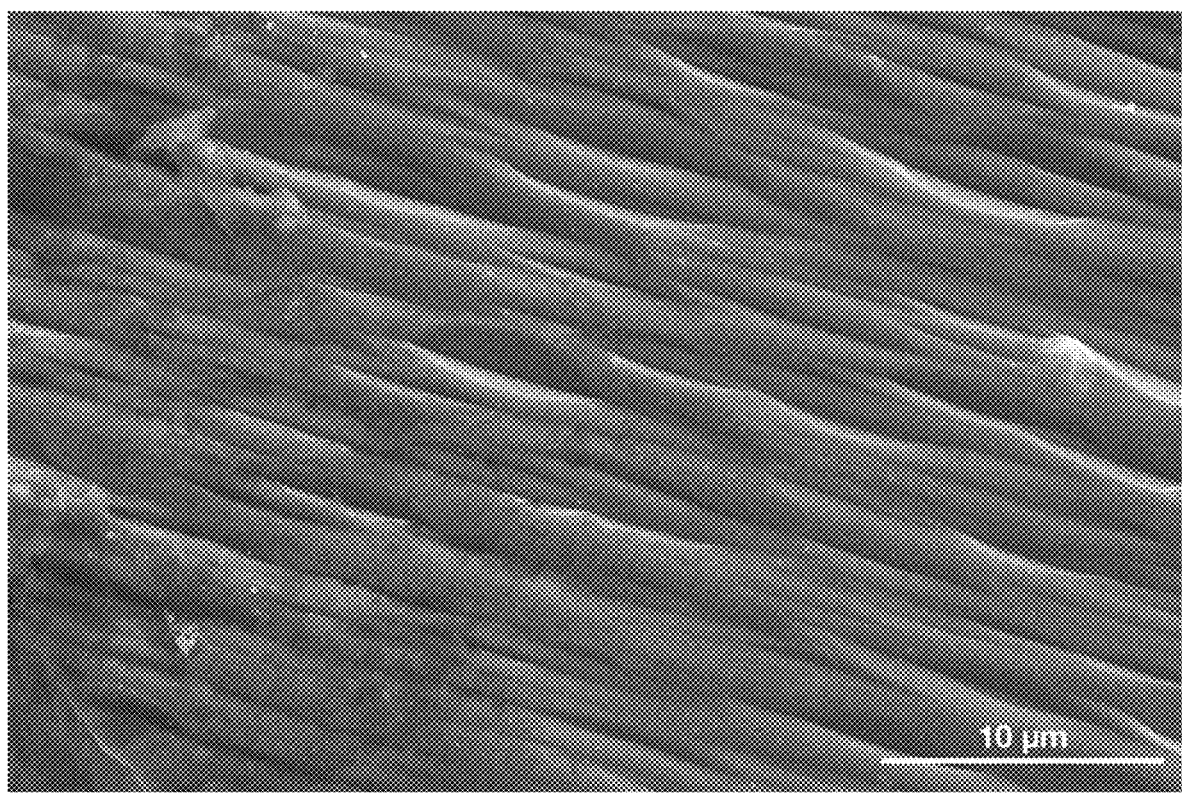
FIG. 35 shows SEM images of functionalized surfaces comprising cord structures on Ge particles prepared via method described in Example 15.

The term cords refer to elongated convex structures whose height does not exceed the width of the base. Cords may have a semi-circle cross-sectional shape, though this is not required. Cords may be parallel to other cords, though this is not required. An example of cords on the surface of a powder particle is shown in FIG. 35.

The term hoodoo refers to protruding pillar-like structures of variable cross-sectional area or cross-sectional shape that are laterally interlinked or interconnected. FIGS. 5A-5D and 33C-33D depict some laterally interlinked nanopillars that may be classified as hoodoos.

The term coral refers to any extending structure whose morphology is irregular or whose shape is not geometric. For example, an elongated structure whose direction changes along its length and whose cross-sectional area or cross-sectional shape is variable may be termed coral. Coral may have interlinked or interconnected features, though this is not required. Any nano- or micro-structure that cannot be easily classified among other classes of structures may be considered a coral. FIGS. 16A-16C, 17A-17B, and 33A-33B depict irregularly shaped nanoscale formations that may be classified as coral.

Figure 2:
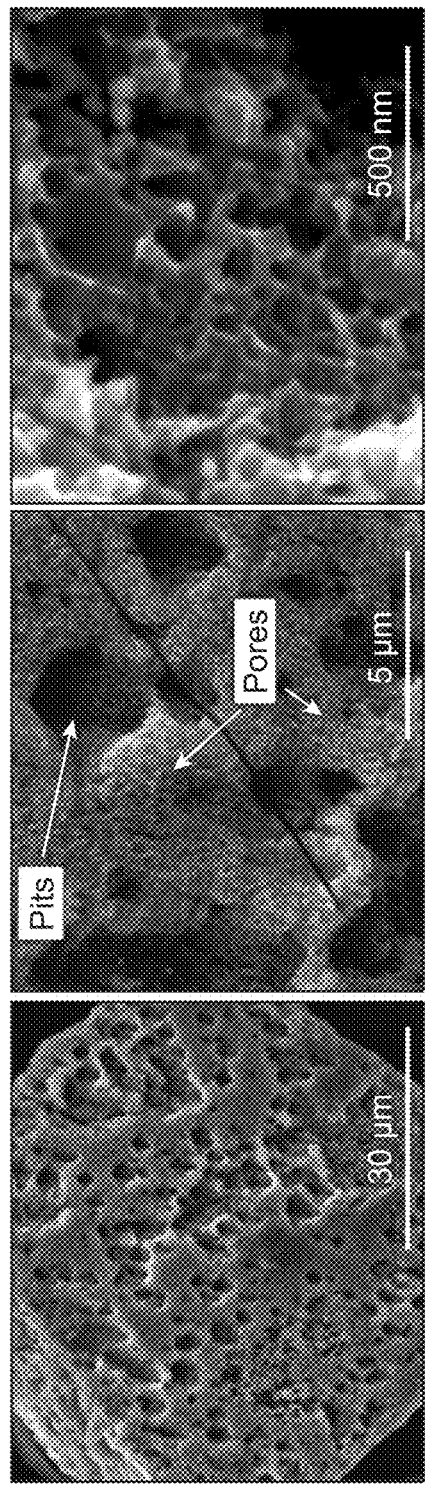
FIGS. 2A-2C depict scanning electron microscopy (SEM) images of a heterofunctionalized powder particle comprising pits and pores. The particle was prepared via the method discussed in Example 2 (Ag-metal-assisted chemical etching (MACE) of Si crystalline particles).
Figure 3:
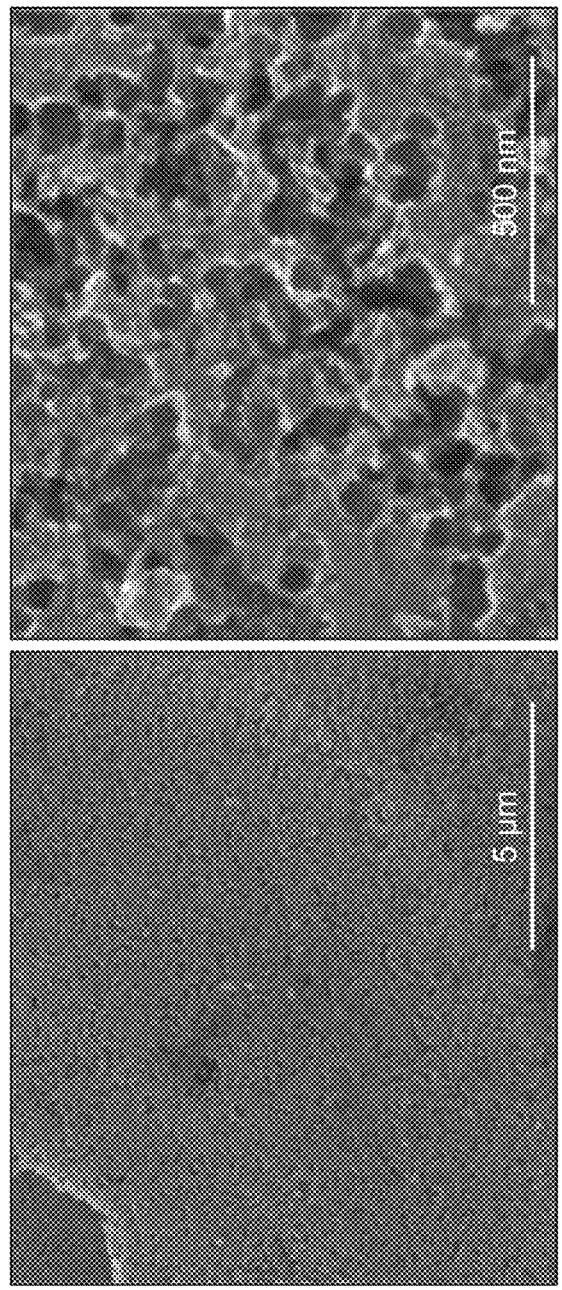
FIGS. 3A-3B depict SEM images of a porous functionalized powder. The particle was prepared via Ag-MACE of Si crystalline particles.
Figure 6A:
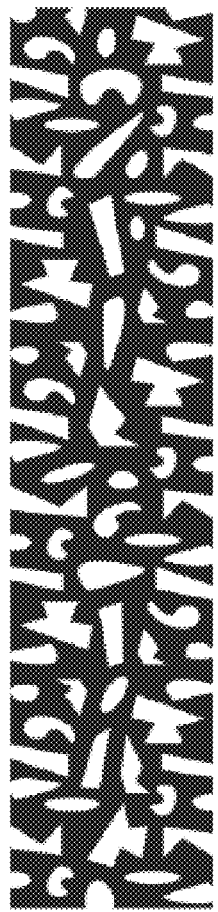
FIGS. 6A-6B depict illustrative cross-sectional views of heterofunctionalized nanowires.
Figure 6B:
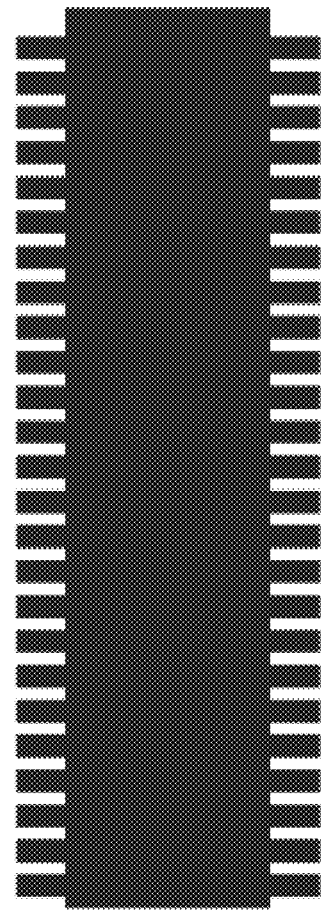
Figure 18:
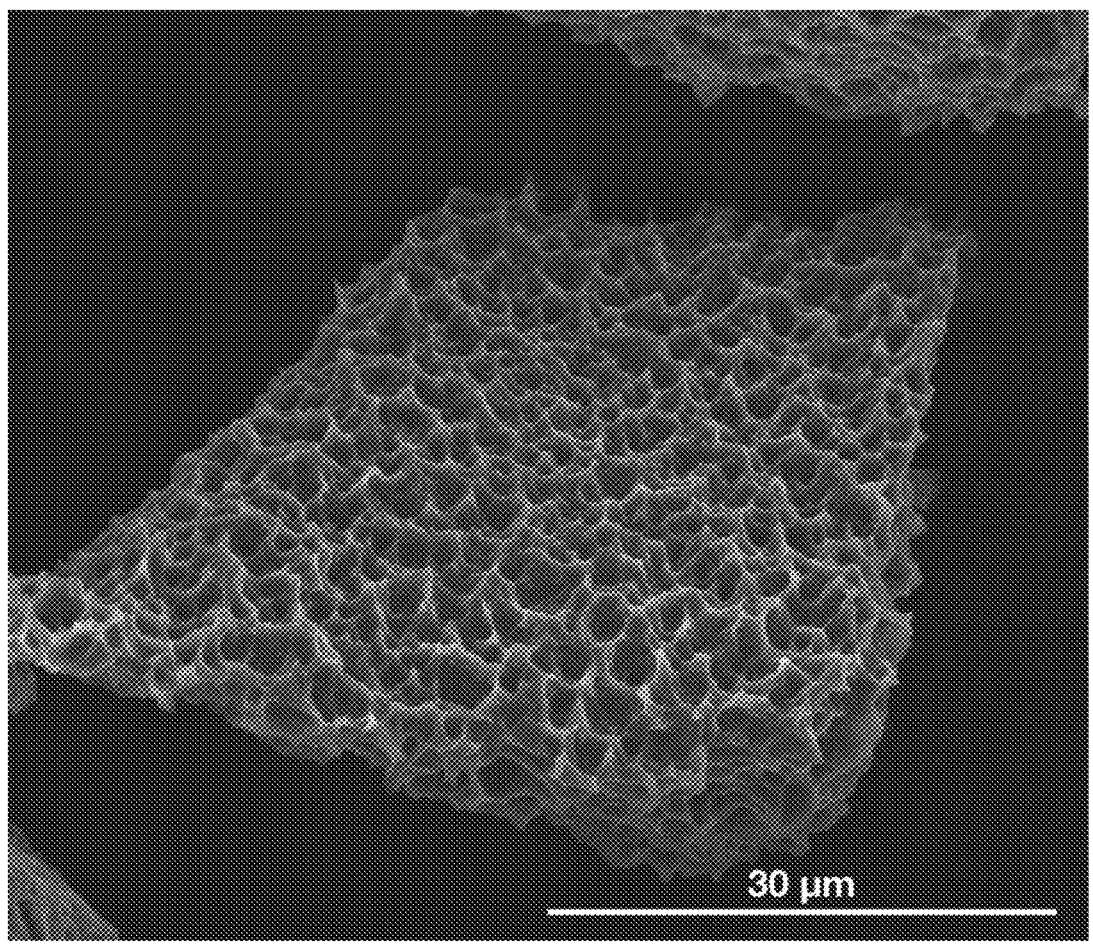
FIG. 18 shows a SEM image of heterofunctionalized morphology comprising pyramids and coral structures prepared via sequential etching of Si particles. The particles were first synthesized via KOH etching forming pyramid structures, as seen in FIG. 21, and then further functionalized via Ag-MACE.
Figure 36:
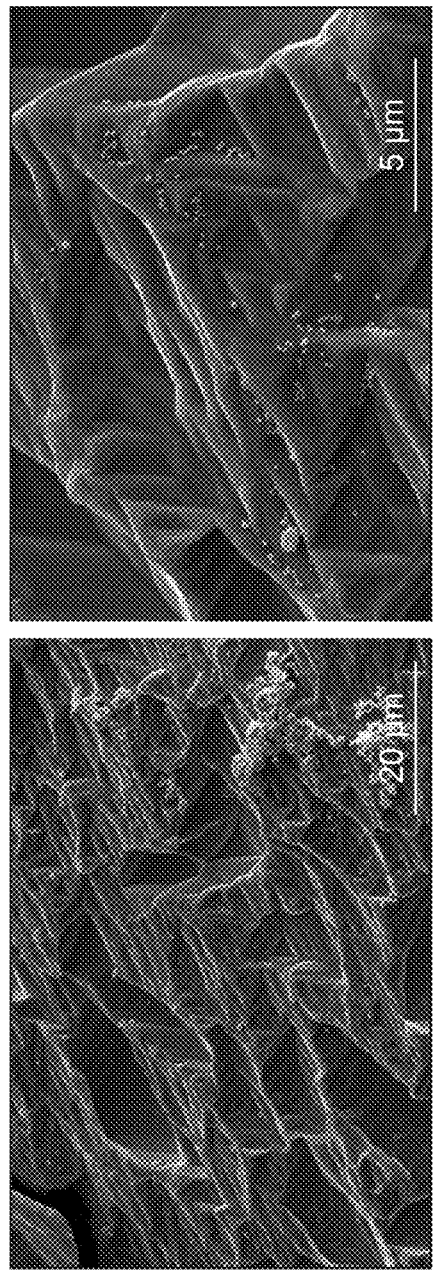
FIGS. 36A-36B show SEM images of heterofunctionalized surfaces comprising cord and triangular-aperture pit structures on Ge particles prepared via method described in Example 15.

A single powder particle may comprise two or more types of structures. In some embodiments, the structures are layered on top of one another, as shown in FIGS. 6A-6B. For example, a powder particle may comprise nanowires on the faces of pyramids. Nanowires may decorate the faces of pyramids, inverted pyramids, craters, cones, hoodoos, coral, cords, walls, fins, ridges, crags, or other nanowires. Pits and pores may decorate the surfaces of nanowires, craters, cones, pyramids, inverted pyramids, coral, cords, walls, fins, ridges, crags, or hoodoos or other pits and pores. A single powder particle may comprise any combination of primary and secondary structures. For example, FIG. 18 depicts a particle with heterofunctionalized morphology comprising pyramids and coral structures. For example, FIGS. 2A-2C depict a particle with overlapping structures comprising pits and pores. For example, FIGS. 36A-36B depict a particle with heterofunctionalized morphology comprising cord and triangular-aperture pits.

Structures formed on powder particles, including primary and second structures, may be characterized by a characteristic dimension. A characteristic dimension may include properties such as length, width, height, diameter, and circumference. The characteristic dimension of a structure formed on a powder particle may be uniform or may vary over the body of the structures. For example, a pyramidal or conical structure may be characterized as having a circumference that decreases from the base to the tip of the pyramid. A structure formed on a powder particle may have multiple characteristic dimensions, e.g., length and radius. A particular characteristic dimension or range of characteristic dimensions may be correlated to certain physical properties of the functionalized powder material. Characteristic dimensions of particular structures may vary over a single particle or may vary between particles.

A structure formed on a powder particle may have a characteristic dimension of about 1 nm, 10 nm, 25 nm, 50 nm, 75 nm, 100 nm, 200 nm, 300 nm, 400 nm, 500 nm, 600 nm, 700 nm, 800 nm, 900 nm, 1 µm, 10 µm, 100 µm, or 1000 µm. A structure formed on a powder particle may have a characteristic dimension of at least about 1 nm, 10 nm, 25 nm, 50 nm, 75 nm, 100 nm, 200 nm, 300 nm, 400 nm, 500 nm, 600 nm, 700 nm, 800 nm, 900 nm, 1 µm, 10 µm, 100 µm, or 1000 µm or more. A structure formed on a powder particle may have a characteristic dimension of no more than about 1000 µm, 100 µm, 10 µm, 1 µm, 900 nm, 800 nm, 700 nm, 600 nm, 500 nm, 400 nm, 300 nm, 200 nm, 100 nm, 75 nm, 50 nm, 25 nm, 10 nm, 1 nm or less.

Two characteristic dimensions of a structure formed on a powder particle may have a particular aspect ratio. For example, an aspect ratio may comprise the ratio of length to width for a particular structure. The aspect ratio may be calculated based upon the average value of a characteristic dimension. For example, a structure with a variable diameter may have an aspect ratio based upon the average diameter over the length of the structure. A particular characteristic aspect ratio or range of aspect ratios may be correlated to certain physical properties of the functionalized powder material. Aspect ratios of a particular structure may vary over a single powder particle or between two different powder particles.

In some cases, a structure formed on a powder particle may be characterized by more than one characteristic or feature dimension. Characteristic or feature dimensions may include widths, heights, depths, spacings, diameters, tip diameters, aperture widths, tip-to-tip distances, base diameters, and widths at peak. In some cases, the characteristic or feature dimensions may have characteristic values or ranges. A range may be defined by a minimum and/or maximum dimension for a structural dimension. Table I below highlights some approximate characteristic dimensions for various structures of the present invention. Actual observed feature dimensions may vary by as much as about 5%, 10%, 15%, 20%, 25% or more above or below the stated feature dimension ranges.

TABLE I

Characteristic Dimensions of Structures

| Structure Type | Feature Dimension | Min Value (nm) | Max Value (nm) |
|---|---|---|---|
| Hoodoo | Width | 30 | 400 |
| Hoodoo | Tip diameter | 10 | 450 |
| Hoodoo | Height | 600 | 9000 |
| Pits | Aperture Width | 10 | 5500 |
| Pore | Aperture Width | 10 | 2500 |
| Coral | Tip to Tip Distance | 100 | 5000 |
| Coral | Tip diameter | 50 | 2000 |
| Coral | Height | 600 | 3000 |
| Nanowire | Width/Diameter | 40 | 1200 |
| Nanowire | Height | 1500 | 10000 |
| Pyramids | Base Diameter (Full Width) | 25 | 5000 |
| Pyramids | Height | 600 | 3000 |
| Pyramids | Tip to Tip Distance | 100 | 5000 |
| Inverted Pyramids | Aperture Width | 100 | 6000 |
| Inverted Pyramids | Depth | 25 | 2500 |
| Walls | Spacing | 200 | 1500 |
| Walls | Width at Peak | 50 | 500 |
| Cords | Width | 500 | 3500 |
| Cu Particles | Diameter | 10 | 800 |
| Ag Particles | Diameter | 5 | 1500 |

A structure or group of structures on a functionalized powder particle may be characterized as having an average aspect ratio of about 1:1000, 1:100, 1:10, 1:5, 1:2, 1:1, 2:1, 5:1, 10:1, 100:1, or about 1000:1. A structure or group of structures on a functionalized powder particle may be characterized as having an average aspect ratio of at least about 1:1000, 1:100, 1:10, 1:5, 1:2, 1:1, 2:1, 5:1, 10:1, 100:1, or about 1000:1 or more. A structure or group of structures on a functionalized powder particle may be characterized as having an average aspect ratio of no more than about 1000:1, 100:1, 10:1, 5:1, 2:1, 1:1, 1:2, 1:5, 1:10, 1:100, or 1:1000 or less.

Structures on a powder particle may have a characteristic size dispersity. A size dispersity may be monomodal, bimodal, trimodal, or multimodal. The size dispersity may be determined for any characteristic dimension of the structures. For example, a powder particle functionalized with pillars may have a monomodal pillar length dispersity around the average value of the pillar lengths. The size dispersity of structures may be determined such that about 10%, 20%, 30%, 40%, 50%, 60%, 70%, 80%, 90%, or 95% of the structures are within 50% of the average size of the structure. The size dispersity of structures may be determined such that at least about 10%, 20%, 30%, 40%, 50%, 60%, 70%, 80%, 90%, or 95% or more of the structures are within 50% of the average size of the structure. The size dispersity of structures may be determined such that no more than about 95%, 90%, 80%, 70%, 60%, 50%, 40%, 30%, 20%, or 10% of structures are within 50% of the average size of the structure. A particular characteristic structure size dispersity may be correlated to certain physical properties of the functionalized powder material. The size dispersity of a particular structure may vary between regions of a single powder particle or between two different powder particles.

Structures on a particle may have a characteristic surface density. The surface density may be defined as the number of unique structures per unit of area. A surface density may be calculated for a single type of structures (e.g., pillars) or may include the density of two or more types of structures (e.g., the total surface density of all structures on a powder particle). A particular characteristic surface density may be correlated to certain physical properties of the functionalized powder material. The surface density of a particular structure may vary between regions of a single powder particle or between two different powder particles.

A powder particle may have a structure surface density of at least about 1 structure per $\mu m^2$, 5 structures per $\mu m^2$, 10 structures per $\mu m^2$, 15 structures per $\mu m^2$, 20 structures per $\mu m^2$, 25 structures per $\mu m^2$, 30 structures per $\mu m^2$, 40 structures per $\mu m^2$, 50 structures per $\mu m^2$, 100 structures per $\mu m^2$, 250 structures per $\mu m^2$, 500 structures per $\mu m^2$, 1000 structures per $\mu m^2$, or 10000 structures per $\mu m^2$ or more. A powder particle may have a structure surface density of no more than about 10000 structures per $\mu m^2$, 1000 structures per $\mu m^2$, 500 structures per $\mu m^2$, 250 structures per $\mu m^2$, 100 structures per $\mu m^2$, 50 structures per $\mu m^2$, 40 structures per $\mu m^2$, 30 structures per $\mu m^2$, 25 structures per $\mu m^2$, 20 structures per $\mu m^2$, 15 structures per $\mu m^2$, 10 structures per $\mu m^2$, 5 structures per $\mu m^2$, 1 structures per $\mu m^2$ or less.

Functionalized Particle

In some aspects, the present disclosure provides a homofunctionalized (e.g., crystalline, polycrystalline, semi-crystalline or amorphous) (e.g., semiconductor or insulator) powder particle, wherein the powder particle comprises one type of structure selected from the group consisting of pores, pits, craters, nanowires, cones, pinnacles, hoodoos, coral, cords, walls, fins, ridges, crags, pyramids, and inverted pyramids. In some aspects, the present disclosure provides a homofunctionalized (e.g., crystalline, polycrystalline, semi-crystalline, or amorphous) (e.g., semiconductor or insulator) powder particle, wherein the powder particle comprises a structure selected from the group consisting of pits, craters, cones, pinnacles, hoodoos, coral, cords, walls, fins, ridges, crags, pyramids, and inverted pyramids. In some aspects, the present disclosure provides a homofunctionalized (e.g., crystalline, polycrystalline, semi-crystalline, or amorphous) (e.g., semiconductor) powder particle, wherein the powder particle comprises one type of structure selected from the group consisting of pores, pits, craters, nanowires, cones, pinnacles, hoodoos, coral, cords, walls, fins, ridges, crags, pyramids, and inverted pyramids, and wherein the powder particle is not an elemental silicon particle. In some aspects, the present disclosure provides a functionalized (e.g., crystalline, polycrystalline, semi-crystalline, or amorphous) (e.g., semiconductor or insulator) powder particle, wherein the powder particle comprises a submillistructure and further comprises a film coating, plating, chemical functionalization, a dopant, a nanoparticle decoration, or a surface termination. In other aspects, the present disclosure provides a heterofunctionalized (e.g., crystalline, polycrystalline, semi-crystalline, or amorphous) (e.g., semiconductor or insulator) powder particle, wherein the powder particle comprises two or more types of structures. The two or more types of structures may be selected from the group consisting of pores, pits, craters, nanowires, cones, pinnacles, hoodoos, coral, cords, walls, fins, ridges, crags, pyramids, and inverted pyramids.

The average effective diameter of the functionalized powder particle may be between 0.01 and 10,000 μm, such as between 0.1 and 10,000 μm or 0.1 and 1,000 μm. Optionally, the average effective diameters of powder particle may be between 0.1 and 100 μm, 0.1 and 10 μm, 1 and 10,000 μm, 1 and 1,000 μm, 1 and 100 μm, 10 and 10,000 μm, 10 and 1,000 μm, or between 100 and 10,000 μm.

The functionalized powder particle may comprise two or more overlapping structures, such as a nanowire on the face of a pyramid. In some embodiments, nanowires may decorate the faces of pyramids, inverted pyramids, cones, hoodoos, coral, cords, walls, fins, ridges, crags, or other nanowires, and pits and pores may decorate the surfaces of nanowires, cones, pyramids, inverted pyramids, coral, cords, walls, fins or hoodoos or other pits and pores. A single powder particle may comprise any combination of primary and secondary structures.

Figure 37:
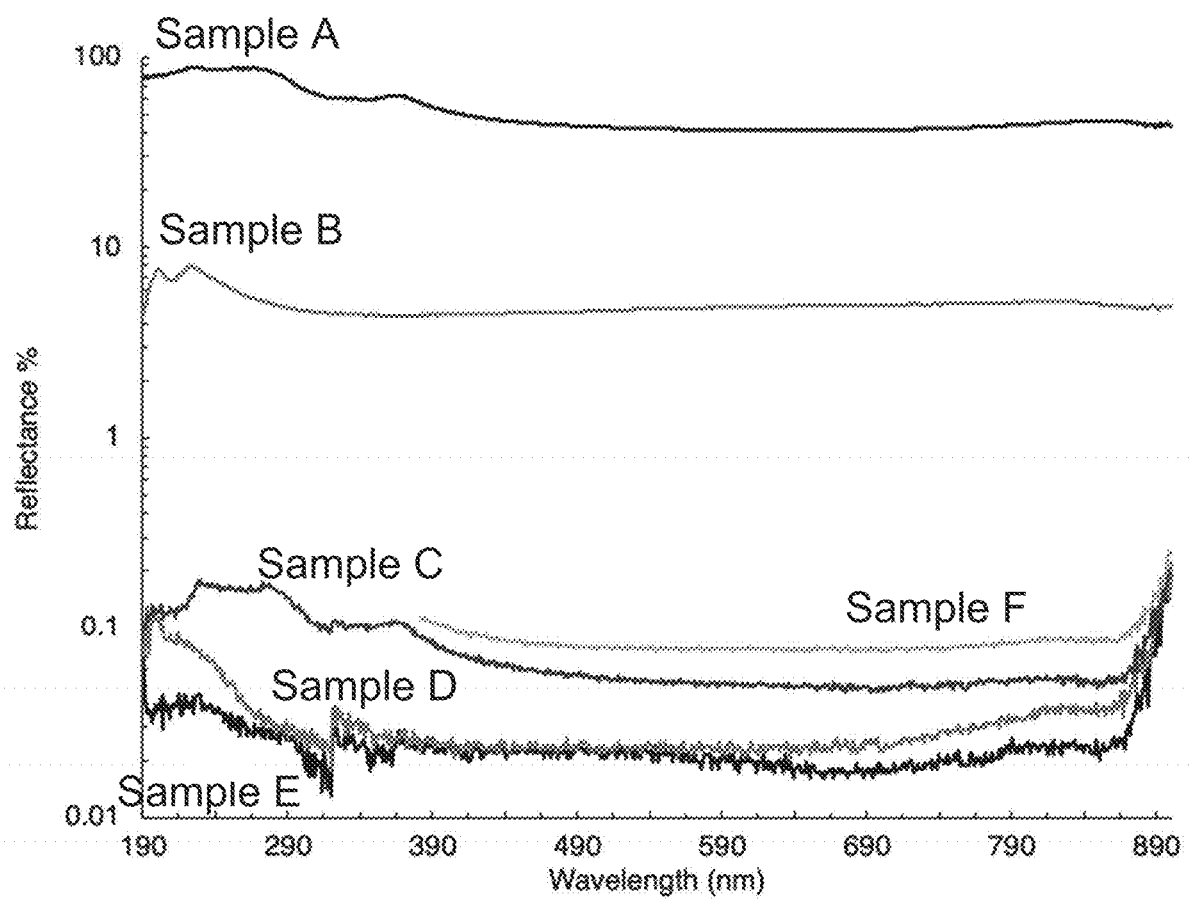
FIG. 37 shows specular UV-VIS reflectance data of several surfaces, measured at 45° angle of incidence with a Shimadzu UV-2401 UV-VIS spectrophotometer. Sample (A) is a polished Si wafer and sample (B) is a bare ABS plastic substrate, for comparison. Samples (C), (D), (E), and (F) are functionalized substrates that were prepared via method described in Example 16. Sample (C) is an ABS plastic substrate coated with functionalized Si particles prepared via method described in Example 11. Sample (D) is an ABS plastic substrate coated with functionalized amorphous SiO particles prepared via method described in Example 13.

In some examples, the particle reflects at most an average of 0.1% of all electromagnetic radiation (e.g., specular and/or diffuse) between the wavelengths of 10 nm and 1,050 nm. In some embodiments, the particle may reflect at most an average of 0.01% of all electromagnetic radiation (e.g., specular and/or diffuse) between 10 nm and 400 nm, at most an average of 0.1% of all electromagnetic radiation (e.g., specular and/or diffuse) between 300 nm and 1,050 nm or at most an average of 0.1% of all electromagnetic radiation (e.g., specular and/or diffuse) between 700 nm and 1,050 nm. In some examples, the particle reflects at most an average of 0.03% of all specular electromagnetic radiation, at 45° angle of incidence, between the wavelengths of 190 nm and 900 nm, as seen in FIG. 37. In some examples, the particle reflects at most 0.046% of specular electromagnetic radiation, at 45° angle of incidence, between the wavelengths of 180 nm and 380 nm, and at most 0.026% between 380 nm and 740 nm. In some examples, the particle reflects at most 1% of all electromagnetic radiation (e.g., specular and/or diffuse) between the wavelengths of 300 nm and 1,050 nm. In some embodiments, the particle may reflect at most 1% of all electromagnetic radiation (e.g., specular and/or diffuse) between 10 nm and 400 nm, 1% of all electromagnetic radiation (e.g., specular and/or diffuse) between 300 nm and 1,050 nm or 1% of all electromagnetic radiation (e.g., specular and/or diffuse) between 700 nm and 1,050 nm. In some examples, the particle reflects at most an average of 10% of all electromagnetic radiation (e.g., specular and/or diffuse) between the wavelengths of 10 nm and 1,050 nm. In some embodiments, the particle may reflect at most 10% of all electromagnetic radiation (e.g., specular and/or diffuse) between 10 nm and 400 nm, 10% of all electromagnetic radiation (e.g., specular and/or diffuse) between 190 nm and 900 nm or 10% of all electromagnetic radiation (e.g., specular and/or diffuse) between 700 nm and 1,050 nm. In some examples, the particle reflects at most 25% of all electromagnetic radiation (e.g., specular and/or diffuse) between the wavelengths of 300 nm and 1,050 nm. In some embodiments, the particle may reflect at most 25% of all electromagnetic radiation (e.g., specular and/or diffuse) between 10 nm and 400 nm, 25% of all electromagnetic radiation (e.g., specular and/or diffuse) between 190 nm and 900 nm or 25% of all electromagnetic radiation (e.g., specular and/or diffuse) between 700 nm and 1,050 nm.

Physical and Chemical Properties of Functionalized Particle

The structure and texture of a functionalized powder particle may alter the physical and/or chemical properties of at least a portion of the particle. The properties may vary radially and/or angularly. Examples of powder particle properties and characteristics that may be altered due to the structure and texture include, but are not limited to, surface energies, surface area, surface roughness, density profile, refractive index, optical constant, electrostatic, band structure, bandgap, shear modulus, plasticity, coefficient of friction, specific weight, acoustical properties, thermal properties, optical properties, electrical properties, chemical properties, non-covalent interactions, photoluminescence, photo absorption, cell lysis, omniphobicity, hydrophobicity and hydrophilicity.

Functionalized powder particles may display altered material properties more readily than common substrates that have been similarly structurally functionalized. Structurally functionalizing powder particles will create more complexity than similar structuring on a non-particulate substrate, such as a Si wafer. Functionalized powder particles have a high surface area to volume ratio (or surface area to mass ratio) and are smaller than non-powder particle forms, so more functionalized powder particle mass or volume is comprised of submillistructures. Submilli-structures on a (e.g., crystalline, polycrystalline, semi-crystalline, or amorphous) powder particle may display a greater directional range than structures on non-particulate substrates due to functionalization of the entire powder surface. Omnidirectional structures may enhance the material properties of functionalized powder particles for three-dimensional applications. Functionalized powder particles may feature a broader range of physical length scales than on non-particulate substrates. A broader range of length scales may offer a broader range of material properties in functionalized powder particles.

Figures 25A, 25B:
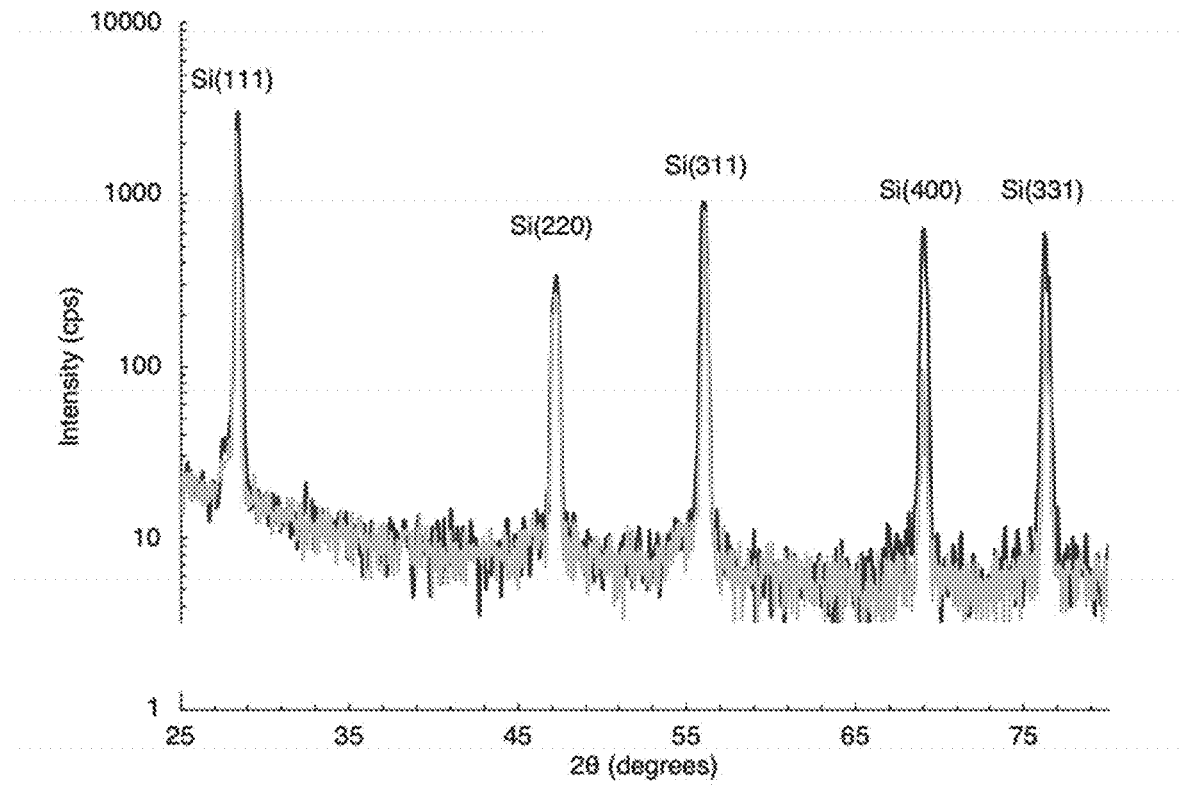
FIG. 25A shows X-ray (Cu Kαi) powder diffraction data from nonfunctionalized and functionalized crystalline Si powder, measured with a Rigaku Ultima IV 3 kW X-ray diffractometer system. The functionalized powder was prepared via the method discussed in Example 7. Shifts in peak position are seen for the Si(111) and Si(311) peaks for the functionalized powder, indicating lattice expansion and contraction along the <111> and <311> directions, respectively.
FIG. 25B shows the peak fitting results.

Functionalized (e.g., crystalline, polycrystalline, and semi-crystalline) powder particles may have altered crystalline lattice structure and band structure than nonfunctionalized particles or nonfunctionalized substrates. For example, FIGS. 25A-25B show X-ray (Cu Kαi) powder diffraction data from nonfunctionalized crystalline Si powder and functionalized crystalline Si powder prepared via methods described in Example 7 after 90 minutes of etching. These functionalized particles (45 μm average diameter) have a structurally functionalized surface that is 1.5 μm thick. This structural functionalization results in lattice expansion and contraction of the whole functionalized particle, including the solid core and the structured surface, even though the structural functionalization accounts for a small portion of the particle volume. The crystal lattice expansion and contraction along the <111> and <311> directions is evident by shifts in the peak positions for the Si(111) and Si(311) peaks, respectively. Alterations to the crystal lattice structure may alter the band structure, compared to nonfunctionalized particles or nonfunctionalized substrates, and is done so without changing the bulk chemical composition or introducing bulk crystalline defects.

Functionalized powder particles may have altered thermal properties. Thermal expansion and contraction may have diminished impact on the nanostructures. Cracking and other mechanical disruptions may be reduced in functionalized powder particles.

Pluralities of Functionalized Particles

A functionalized particle may form part of a homogeneous mixture of like particles or part of a heterogeneous mixture of two or more variants of particles. One variant may differ from another by at least one physical or chemical property, such as chemical composition, size, shape, surface modification, type of structure on the surface, type of structure on the subsurface, chemical functionalization, nanoparticle decoration, surface termination, or doping.

In some embodiments, two or more functionalized particle variants are blended together to achieve a desired physical property. For example, a mixture of functionalized particles comprising different elemental or compound species, such as Si or Ge, can be used to provide a blend having preferred optical properties. The packing density of particles may be increased by mixing functionalized particles having different sizes, such that smaller particles occupy or fill in the voids between larger particles. A mass density gradient may be formed by mixing particles of different sizes. A graded optical index of refraction may also be formed by mixing particles of different sizes. A mixture of particles may be formed wherein some particles have durable or delicate features. For example, large particles with inverted pyramid structures may be mixed with small particles covered in nanowires. The small particles may occupy the voids between the larger particles such that the more delicate nanowires are protected from mechanical or other disruptions.

Such mixtures, either homogeneous or heterogeneous, may be used in a variety of applications. Examples include a filter, such as a fluid or gas filter, that comprises a vessel containing one or more functionalized particles. In this example, the functionalized particles may mechanically or chemically bind, interact or react with elements, compounds, molecules, particles or cells as the fluid or gas flows through the filter. The application of such a filter would include the extraction of contaminants from a fluid or gas, catalysis or enhancement of certain chemical reactions, lysing of cells for intracellular analysis and harvesting of cellular components, and the removal of unwanted microorganisms from a fluid. This high surface area of the functionalized particles allow for a greater amount of chemicals to be embedded or decorated per particle than nonfunctionalized particles. In some embodiments, functionalized powder particles may be utilized in an analytical column. In some embodiments, functionalized powder particles may be modified with a functional group such as a flavor or scent compound. In some embodiments, nanoparticles containing flavor or scent compounds could be embedded or decorated on the surface of functionalized powder particles. Functionalized powder particles may be used to transfer or replicate nanostructures on other materials. For example, powder particles with nanowires could be used as a mold, stamp or template to create structures in the surface of a softer material.

Composites of Functionalized Particles

In certain aspects, the present disclosure provides a surface comprising one or more functionalized (e.g., crystalline, polycrystalline, semi-crystalline or amorphous) (e.g., semiconductor or insulator) powder particle, wherein the powder particle optionally comprises one or more structures selected from the group consisting of pores, pits, craters, nanowires, cones, pinnacles, hoodoos, coral, cords, walls, fins, ridges, crags, pyramids, and inverted pyramids, and wherein the diameter of the powder particle is between 0.01 μm and 10,000 μm. The mean diameter of the smallest 30% of powder particles may be 200% smaller than the mean diameter of the largest 10% of powder particles. Optionally, the mean diameter of the smallest 10% of powder particles may be 200% smaller than the mean diameter of the largest diameter of the largest 10%, or the mean diameter of the smallest 1% of powder particles may be 200% smaller than the mean diameter of the largest diameter of the largest 10%, or the mean diameter of the smallest 30% of powder particles may be 100% smaller than the mean diameter of the largest diameter of the largest 10%, or the mean diameter of the smallest 10% of powder particles may be 50% smaller than the mean diameter of the largest diameter of the largest 10%. The surface may further comprise a film separating the powder particle from the atmosphere. The surface may be anti-reflective, reflective, antimicrobial, hydrophobic, hydrophilic, antifouling, non-stick, or have any physical property or combination of physical properties as desirable for a chosen application.

Figure 9C:
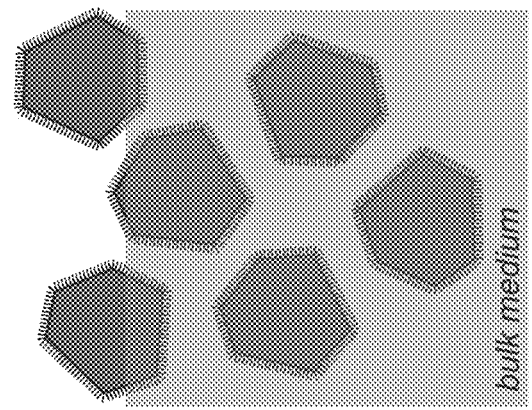
FIGS. 9A-9C depict a cross-sectional view of several possible configurations for integration of functionalized powder particles into a coating or composite.
Figure 9B:
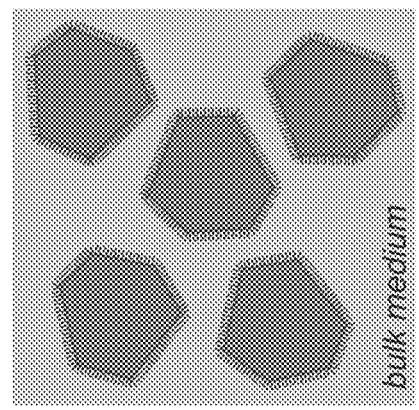
Figure 9A:
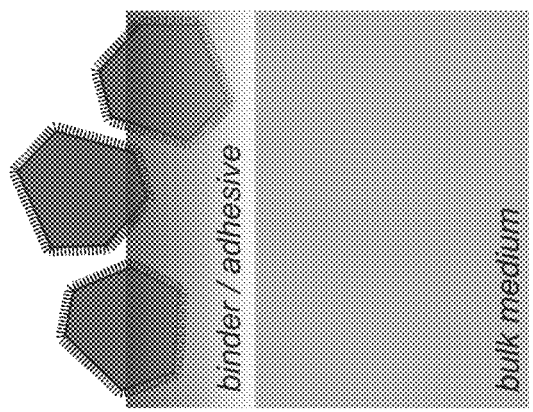

One or more functionalized particles described herein may be used as a component or additive in a bulk material, fiber, surface, or surface coating, for example, as shown in FIGS. 9A-9C, The concentration, distribution (e.g., out-of-plane and in-plane positioning), and orientation of the functionalized particles may be determined separately for a given application. A functionalized powder particle may have altered interactions with a matrix or medium due to its increased surface area when compared to a nonfunctionalized particle. For example, the functionalized powder particle may have increased chemical or bonding sites compared to nonfunctionalized particles. Functionalized powder particles may be used to formulate more durable composites. The smaller length scales of the nanostructures may inhibit fracture propagation when compared to substrates such as semiconductor wafers. In some examples, the decreased mass density of functionalized particles may reduce the mass of a composite when compared to nonfunctionalized particles.

In some examples, one or more functionalized particle is embedded in a surface such that at least one powder particle is exposed to the atmosphere. In this arrangement, structures of the embedded functionalized particles are at least partially exposed at the surface of the matrix, medium, fiber, binder or adhesive. Optionally, one or more functionalized particles may adhere to a matrix, medium, fiber, binder or adhesive such that a particle is fully exposed. The heights of exposed particles may be varied and the heights of particles relative to each other may be homogeneous or heterogeneous. Also, the volumes of exposed particles may be varied and the volumes of particles relative to each other may be homogeneous or heterogeneous. Optionally, one or more functionalized particle may adhere to a matrix, medium, fiber, binder or adhesive such that a particle is fully submerged.

Figure 7:
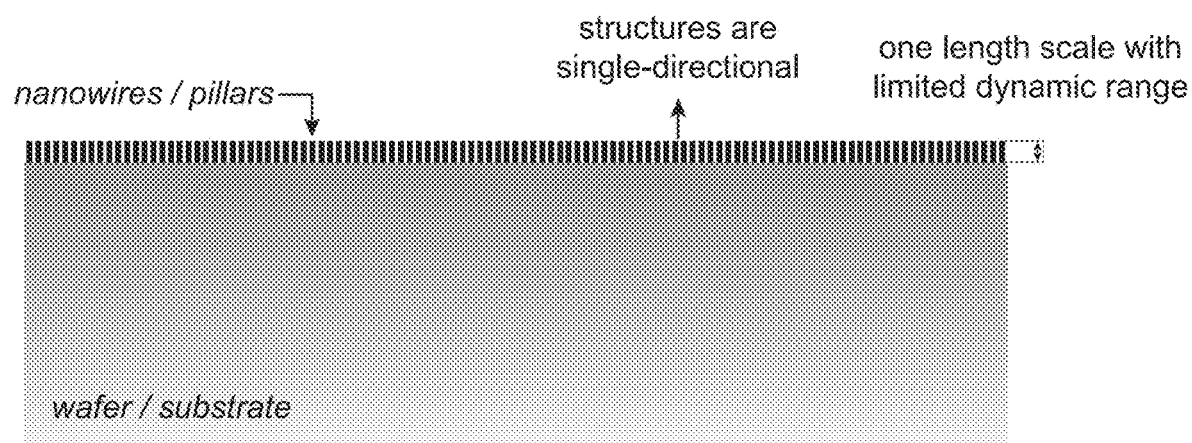
FIG. 7 illustrates a cross-sectional view of the geometry of nanostructuring on a wafer or substrate. The nanowires and wafer are not drawn to scale.
Figure 8:
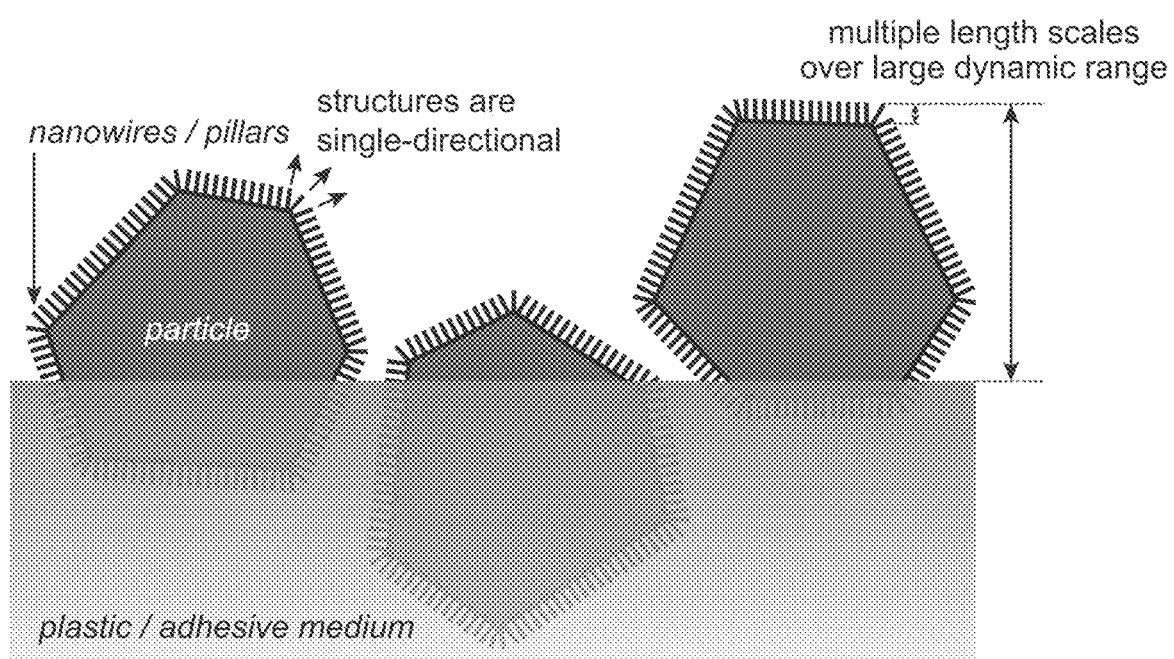
FIG. 8 illustrates a cross-sectional view of a composite comprising a few functionalized powder particles embedded in a plastic or other medium. The particles and nanostructuring are not drawn to scale. The illustrated structures are omni-directional.

In some examples, one or more functionalized powder particles at the surface of a composite material may confer a broader range of length scales at the composite surface in comparison to a nanostructured wafer or substrate, altering the physical properties of the material, as shown in FIGS. 7 and 8. For example, a composite comprised of functionalized powder particles in a resin may absorb a broader range of electromagnetic radiation than a non-particulate substrate, such as a semiconductor wafer, due to the presence of nanoscale and microscale features.

In some examples, one or more partially-exposed functionalized powder particles may alter the mechanical properties of a composite material. The exposed nanostructures at the surface of the composite may be protected from damage by the particle cores or their orientation relative to the macro surface.

In some examples, one or more functionalized powder particle at the surface of a composite may increase the surface area of the composite surface. The composite surface area may exceed that of a non-particulate substrate, such as semiconductor wafers. Composites comprising one or more exposed functionalized powder particle may have a larger functional density (functional surface area per particle footprint area) when incorporating powder particles with sufficient surface packing density.

Method of Altering a Surface Characteristic

In some aspects, the present disclosure provides a method of altering a characteristic of an article, the method comprising incorporating one or more functionalized (e.g., crystalline, polycrystalline, semi-crystalline, or amorphous) (e.g., semiconductor or insulator) powder particle into the article, wherein the powder particle comprises one or more submillistructures optionally selected from the group consisting of pores, pits, craters, nanowires, cones, pinnacles, hoodoos, coral, cords, walls, fins, ridges, crags, pyramids, and inverted pyramids, wherein the diameter of the powder particle is between 0.01 µm and 10,000 µm. The article may be any article described herein, such as a medical device, cookware, an appliance, a countertop, a vehicle, a boat, or an aircraft. The article may be selected from office supplies, office equipment, electronics, containers, kitchenware, cookware, housewares, textiles, hardware, consumer products, vehicles and vessels, filters, pumps, aquatic equipment, surfaces, furniture, appliances, devices, building materials, military equipment, tools, solar cells, currency, medical supplies, medical devices, paper goods, manufacturing equipment, food processing equipment and optical equipment. In some embodiments, the article comprises rubber, plastic, metal, glass or ceramic. In some embodiments, the altering comprises one or more of reducing absorbance of visible light, increasing absorbance of visible light, increasing reflectivity of light, reducing reflectivity of light, increasing antimicrobial activity, increasing antifouling activity, increasing hydrophobicity, increasing hydrophilicity, increasing electrical conductivity, increasing electrical resistivity, increasing luminescence, increasing the surface energy, reducing the surface energy, increasing the coefficient of friction, and reducing the coefficient of friction of the article. The incorporating may comprise coating the article with the powder particle or embedding the powder particle in the article.

Antimicrobial Applications

Functionalized particles of the present disclosure may be used to form an antimicrobial surface. The antimicrobial mode of action may be physical or chemical, including ultraviolet radiation, microwave radiation and heating. An antimicrobial functionalized particle described herein may exhibit one or more antimicrobial mode of action. In some examples, the nanostructures that may provide antimicrobial activity may include nanowires, pinnacles, cones, pores, hoodoos, coral, cords, walls, fins, ridges, crags, pyramids, inverted pyramids and hybrid structures. The height of nanowires for antimicrobial activity may fall within a range of 10 nm to 5 µm. In some embodiments, the height of nanowires for antimicrobial activity may fall within 10 nm to 200 nm, 50 nm to 500 nm, 100 nm to 1 µm, 250 nm to 2 µm, or 500 nm to 5 µm. The diameter of nanowires for antimicrobial activity may fall within the range of 10 nm to 1000 nm. In some embodiments, they may have diameters of 10 nm to 100 nm, 50 nm to 250 nm, 100 nm to 500 nm or 250 nm to 1000 nm. The extending or convex vertical component of cones, pores, hoodoos, coral, cords, walls, fins, ridges, crags, pyramids, inverted pyramids and hybrid structures for antimicrobial activity may fall within a range of 1 nm to 5 µm. In some embodiments, the extending or convex vertical component of cones, pores, hoodoos, coral, trenches, fins, ridges, crags, pyramids, inverted pyramids and hybrid structures for antimicrobial activity may fall within 1 nm to 200 nm, 50 nm to 500 nm, 100 nm to 1 µm, 250 nm to 2 µm, or 500 nm to 5 µm. The width along the narrow dimension of the cross-section of extending or convex components of cones, pores, hoodoos, coral, trenches, fins, ridges, crags, pyramids, inverted pyramids and hybrid structures for antimicrobial activity may fall within the range of 1 nm to 10,000 nm. In some embodiments, they may have dimensions of 1 nm to 100 nm, 50 nm to 250 nm, 100 nm to 500 nm, or 250 nm to 1000 nm.

Physical mode of action: A cell may be killed or lysed by the physical interaction between the cell membrane and the functionalized particle surface. The antimicrobial activity and efficacy may depend on the specific type of structure on the particle that is in contact with the cell membrane. Not wishing to be bound by any particular theory, the cell may be killed when the adhesion force between the functionalized particle and the cell membrane is greater than the cohesion force of the cellular membrane. In some examples, a virus may be captured, immobilized, or inactivated by the interaction between the virus and the functionalized particle surface.

In some examples, a cell may be killed when it adsorbs onto the surface of a functionalized powder particle. The physical mode of cell death may vary depending upon whether a surface is hydrophobic or hydrophilic. For example, a functionalized powder particle with a hydrophobic surface may attract the hydrophobic tail of lipids in the cell membrane, causing the extraction of lipid molecules from the membrane. If a sufficient amount of lipids are extracted, the membrane may rupture, leading to cell death. In some embodiments, a functionalized powder particle with a hydrophilic surface may adsorb the hydrophilic heads of membrane lipids, leading the membrane to spread itself over the nanostructure surface. As the spread of the membrane increase, the membrane may become strained to failure, leading to cell death. For both examples, the physical cause of cell death may not be linked to cell membrane piercing by any nanostructures. In some examples, the hydrophobicity or hydrophilicity may be altered or enhanced by further functionalizing the particle with functional compounds.

In some examples, the cell kill rate (cells killed per time) or cell lysis rate (cells lysed per time) may be increased by subjecting the antimicrobial functionalized powder particles to a mechanical process. Any mechanical process may be chosen such that it imposes additional forces upon a cell, which may result in increased attractive forces between the functionalized powder and the cell membrane which in turn may cause membrane failure. For example, one or more functionalized particle may be subjected to mechanical vibration to rupture a cell. In some embodiments, one or more functionalized particles may be subjected to a mechanical deformation to rupture a cell. In some examples, mechanical deformation of a functionalized powder particle may be achieved by thermal cycling or piezoelectric deformation.

Chemical mode of action: In some examples, one or more functionalized powder particle may be subject to one or more additional processes that add active antimicrobial chemical components. Such surface functionalization may be aided by the increased amount of surface area of the functionalized particle compared to a nonfunctionalized particle, wafer, or substrate. For example, one or more functionalized particles decorated with Ag or Cu nanoparticles may comprise a composite material with antimicrobial properties. In some examples, metal nanoparticles may remain residually from the MACE process. In some examples, an active antimicrobial chemical may be added to the functionalized particle. In some embodiments, active chemical components may be added to structurally functionalized particles that do not have antimicrobial properties. In some embodiments, functionalized particles may be used as a vehicle for integrating chemicals into a composite.

Other physical modes of action: In some examples, one or more functionalized powder particles may be antimicrobial if its chemical composition and crystal structure allows the emission of ultraviolet (UV) light. UV light emission may be prompted by the application of an electric field or other methods. For example, a functionalized particle may comprise InGaN, a UV-emitting semiconductor material. In some embodiments, InGaN, diamond carbon, BN, AlN, AlGaN, or AlGaInN may be chosen as UV-emitting materials for antimicrobial functionalized powder particles.

In some examples, functionalized powder particles may have enhanced antimicrobial properties in the presence of microwave radiation. Microwave radiation of sufficient intensity is capable of killing cells. At lower intensity, microwave radiation may produce significant damage to a cell. Microwave radiation in the presence of one or more antimicrobial functionalized particles may kill cells as a result of two or more mechanisms of cellular damage acting in concert. Such an embodiment may reduce the intensity of microwave radiation necessary to kill cells.

In some examples, one or more functionalized powder particles may be designed for efficient light absorption, thereby enhancing the antimicrobial properties of the material. Efficient light absorbers may convert light energy into heat, leading to cellular damage or death for cells in contact with the material. In some examples, one or more functionalized powder particles may be designed to efficiently emit infrared radiation, thereby enhancing the antimicrobial properties of the material. Irradiation of cells via infrared light may promote sufficient heating to damage or kill microorganisms. For example, a GaAs powder may be chosen as a particle to be functionalized due to the enhanced infrared (IR) emission spectrum of the material. In some embodiments, AlGaAs may be chosen as an infrared emitting semiconductor particle.

In some examples, the functionalized powder particle may be chosen such that the surface of a functionalized powder particle prevents adhesion of cells. Such a surface may inhibit or prevent the growth and reproduction of cells that come in contract with the composite surface.

Other Exemplary Applications

Figure 27A:
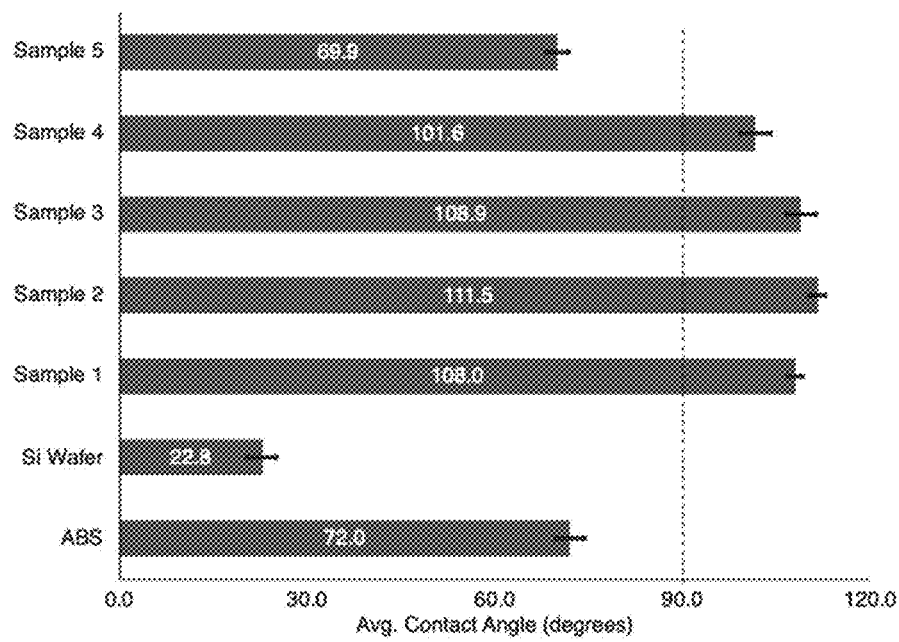
FIGS. 27A-27B show contact angle measurements of an ABS plastic substrate functionalized via attached functionalized Si particles, functionalized SiO particles, nonfunctionalized Si particles. A polished Si wafer and bare ABS substrate are shown for comparison. DI-$H_2O$ contact angle measurements were performed on a ramé-hart Model 200 Standard Contact Angle Goniometer. The functionalized ABS plastic substrates were prepared via the method described in Example 16 and had 100% coverage of particles on the examined surfaces.
Figure 27B:
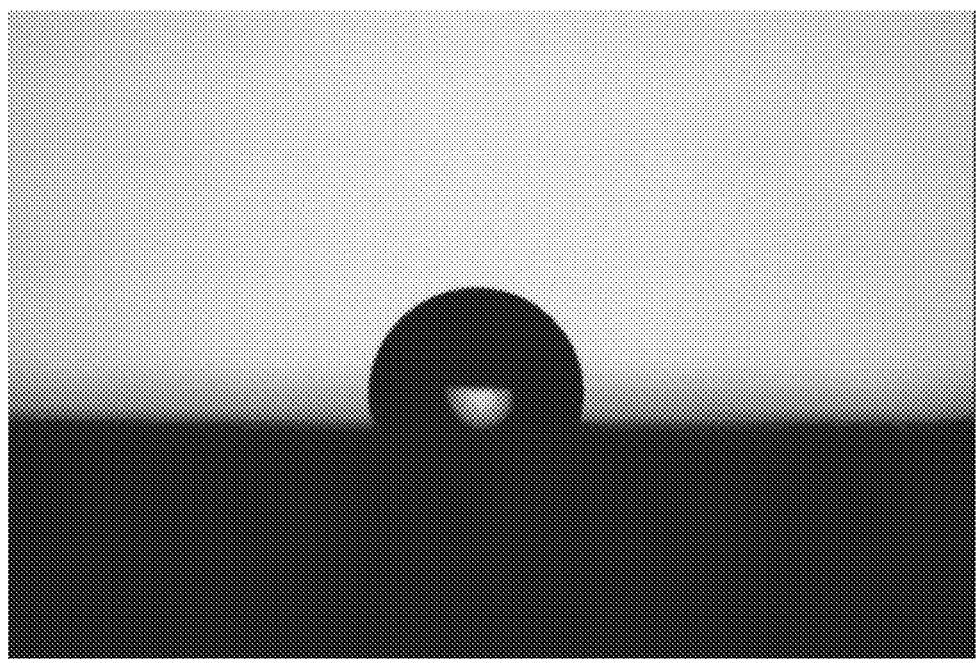

Hydrophobic and hydrophilic surfaces: One or more functionalized particles described herein may be incorporated into the surfaces of articles to alter the hydrophobicity or hydrophilicity of the surface. The surface energy, surface chemistry, nanotexture and microtexture of the functionalized particles each influence the interaction between water and the macro-surface. Suitable functionalized particles may be selected for a given application. For example, FIGS. 27A-27B show examples of DI-$H_2O$ contact angle measurement results for functionalized ABS plastic substrates. Samples 1, 2, 3, and 4 comprise structurally functionalized particles resulting in hydrophobic surface coatings, whereas, Sample 5 comprises nonfunctionalized particles resulting in a hydrophilic surface coating. The alteration to the surface energy can be seen when comparing the contact angles of Samples 1, 2, 3, and 5, which all have the same Si chemical composition and crystal structure, but the structural functionalization of Samples 1, 2, and 3 result in a greater contact angle. Chemical functionalization of the structurally functionalized particles may increase the hydrophobic or antifouling properties of the coating.

Antireflective surface: One or more functionalized powder particles may be designed to create an antireflective surface. A significant amount of light is typically reflected at the abrupt surface/air interface of a given surface, due to the difference in refractive indices of the material and air. Functionalized particles may be designed with multidirectional microstructures and nanostructures to enhance the wide-angle anti-reflective property of the material. FIG. 37 shows an example of specular reflectance spectra at 45° angle of incidence (190-900 nm wavelength) from ABS plastic substrates coated via the method described in Example 16 with functionalized powder particles via the method described in Example 2 (Sample E), 11 (Sample D), and 13 (Sample C). A ABS plastic substrate coated via the method described in Example 16 with nonfunctionalized Si particles (Sample F), bare ABS substrate, and a polished Si wafer are shown as references. The average reflectance of Sample E shown in FIG. 37 is 0.026% for light between 190-900 nm, 0.029% between 190-380 nm, 0.021% between 380-740 nm, and 0.033% between 740-900 nm. The average reflectance of Sample D shown in FIG. 37 is 0.035% for light between 190-900 nm, 0.046% between 190-380 nm, 0.024% between 380-740 nm, and 0.045% between 740-900 nm. The average reflectance of Sample C shown in FIG. 37 is 0.077% for light between 190-900 nm, 0.13% between 190-380 nm, 0.055% between 380-740 nm, and 0.062% between 740-900 nm. The average reflectance of Sample F shown in FIG. 37 is 0.085% for light between 380-900 nm, 0.081% between 380-740 nm, and 0.095% between 740-900 nm. The decrease in reflectance between the surface comprising nonfunctionalized Si powder particles (Sample F) and the surfaces comprising functionalized particles (Samples C, D, and E) is noticeable across a broad range of wavelengths. For example, the average reflectance of Sample F between 380-740 nm is roughly four times that of Sample E. The heterofunctionalized particle morphology of Sample E, which comprises pits and pores, as seen in FIGS. 2A-2C, aids in the broad wavelength antireflective properties. Additionally, these functionalized particle surface composites are antireflective across a wide angular range due to their nano- and micro-scale morphologies.

Light absorbing surface: One or more functionalized powder particles may be designed to create a light absorbing surface. One or more functionalized particles described herein may be embedded in a surface to form a material density gradient, which may result in a refractive index gradient that smoothly transitions between air to the bulk material. Such a gradient may be a broadband light absorber. In some embodiments, antireflective materials may have enhanced light absorbing characteristics due to multiple light scattering events increasing the number of interactions between a photon and the functionalized powder particle. In some embodiments, the combination of heterofunctionalized morphologies may aid in broadband light absorbance. For example, as seen in the broadband antireflective character of Sample E shown in FIG. 37, which comprises heterofunctionalized particles with surfaces comprising pits and pores, as seen in FIGS. 2A-2C.

Figure 10:
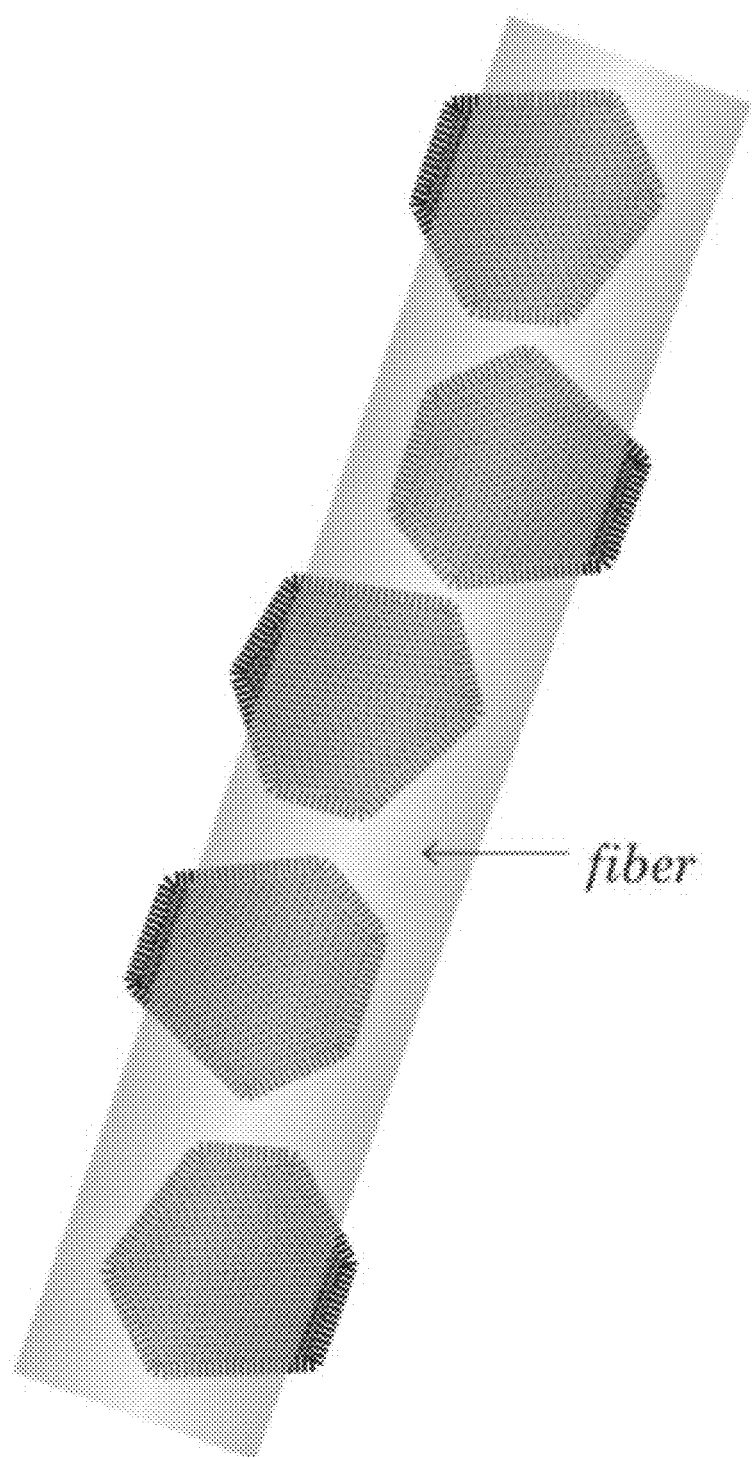
FIG. 10 illustrates a representation of functionalized powder particles embedded within a fiber. The structures and features are not drawn to scale.

Fibers: One or more functionalized powder particles may be embedded in a synthetic or natural fiber, for example, as depicted in FIG. 10. Such fibers may be used in fabrics, composites or other materials. Functionalized powders may be selected to confer various properties upon fibers. Such applications may include, but are not limited to, rendering fibers antimicrobial, hydrophobic, hydrophilic, antireflective, light absorbing, antistatic and increasingly durable.

Figure 11:
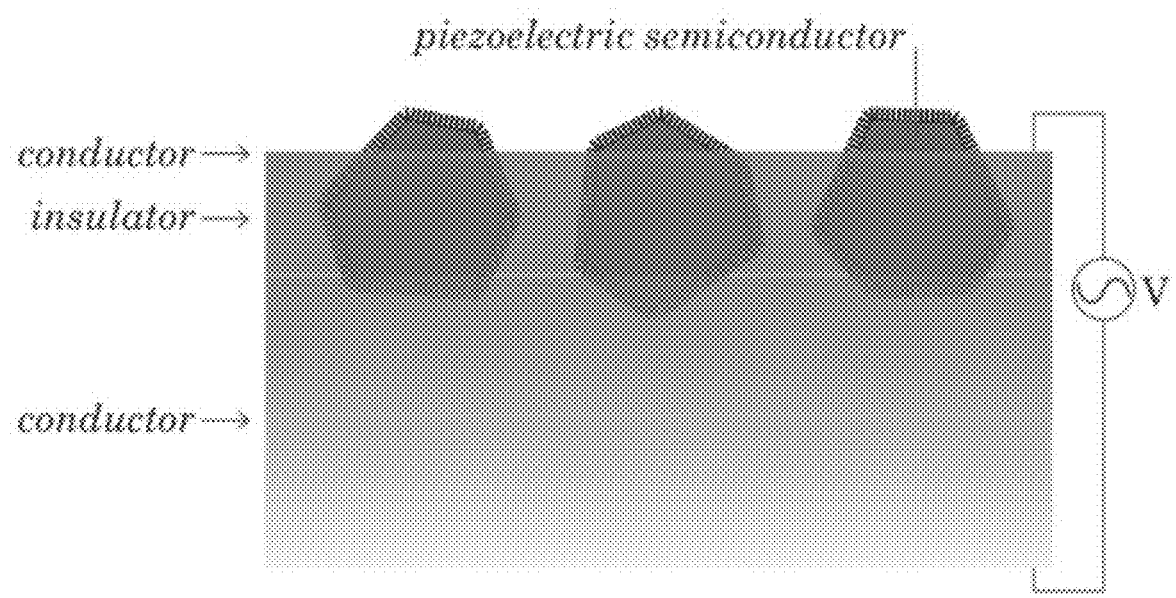
FIG. 11 illustrates an example of a piezoelectric device that utilizes functionalized powder particles and an applied alternating voltage. The design of the device is not limited to this depiction. The features and structures are not drawn to scale.
Figures 12A, 12B:
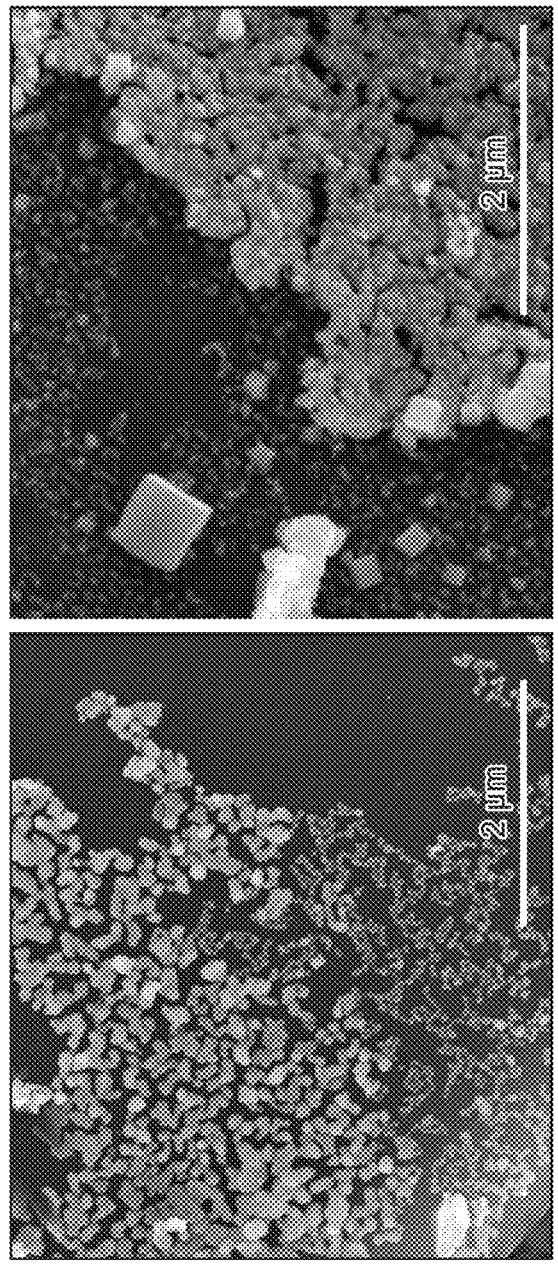
FIGS. 12A-12B show SEM images of Ag (FIG. 12A) and Cu (FIG. 12B) nanoparticles on the surface of powder particles after deposition and rinsing with DI-$H_2O$. Multiple Ag particle size domains are seen in FIG. 12A. Cubic and organic shaped Cu particles are seen in FIG. 12B.

Piezoelectric devices: One or more functionalized powder particle may comprise a piezoelectric device, for example, as shown in FIG. 11. In some examples, a functionalized semiconductor powder particle is embedded in an insulating material while making physical contact with a conducting material on either side of the insulator. The application of an electric field across the device may result in mechanical changes of the functionalized powder particle. Optionally, the device may allow detection of a mechanical force acting on the particle or device due to changes in the electric field across the device. Optionally, the structural functionalization of the particle may alter the particles lattice structure and therefore its band structure and may aid in the utilization of its piezoelectric properties.

Figure 5A:
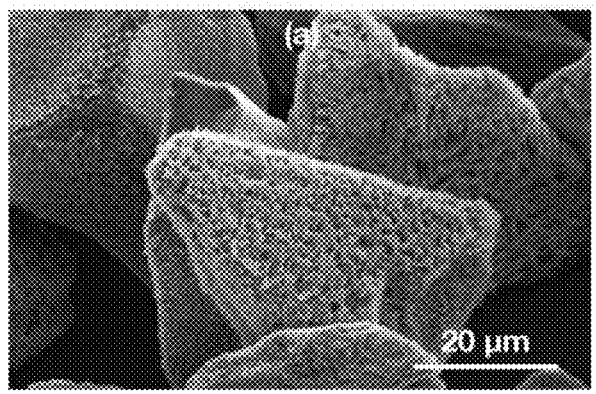
FIGS. 5A-5D show functionalized powder particle comprising hoodoo nanostructures. The particles were prepared via Ag-MACE of Si crystalline particles.
Figure 5B:
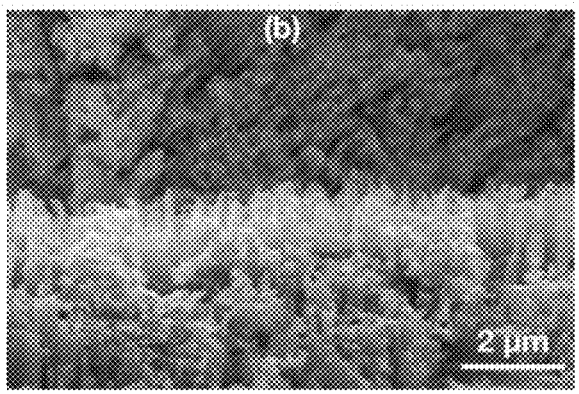
Figure 5C:
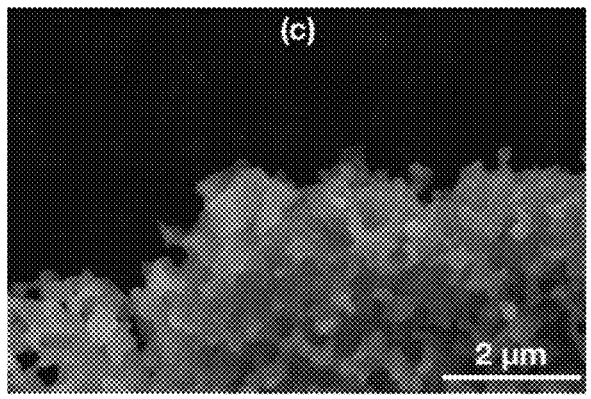
Figure 5D:
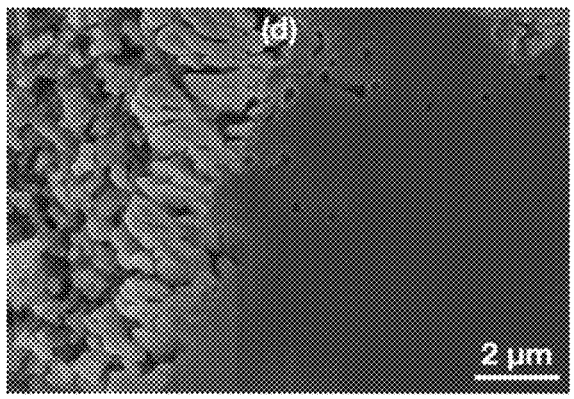

Antistatic applications: One or more functionalized powder particles may be used to reduce the buildup of electrical charge. One or more functionalized particles embedded within a medium may reduce the overall resistivity of the composite due to the electronic properties of chosen semiconductors. For example, one or more functionalized powder particles might be embedded within a plastic to reduce the buildup of electrical charge in the plastic. Materials rendered antistatic by the incorporation of functionalized powder particles may be more resistant to dust accumulation and less likely to produce an electric shock. Optionally, one of more functionalized powder particles may be affixed to the surface of an article and then decorated, coated, or plated with a conductive material. The micro- and nano-scale structures will increase the capacitance per footprint area. The micro- and nano-scale geometry and protruding structures may increase electric discharge from the surface. FIG. 5D shows an example cross sectional SEM image of Pt coated hoodoo structures.

Isolated nanostructures: Prepared nanostructures may be harvested from the surface of one or more functionalized powder particles by mechanical separation or other means. In some examples, separated nanostructures may be dispersed in a bulk medium when the nanoscale properties of the semiconductor or insulator are preferable over the properties of functionalized powder particles with a broader range of nanoscale and microscale physical behaviors. In some examples, a layer-by-layer growth method may be used to form an interface between one or more functionalized powder particle and another medium with the nanostructure embedded in the interface. In such an example, the powder particle core can be separated from the nanostructures, leaving behind a medium with semiconductor or insulator nanoparticles embedded at the surface. The embedded nanostructures may be used as a catalyst growing other structures on the surface of the medium.

Photovoltaic devices: One or more functionalized powder particles may be applied as an additive or component of a photovoltaic device. For example, one or more p-type functionalized powder particles may be coated with an n-type semiconductor to create a material for application in a photovoltaic device. The size and geometry of the functionalized powder particle nanostructure may alter its band structure or bandgap, which may be attributed to quantum confinement. Therefore, the design of functionalized powder particles may allow bandgaps to be altered to be optimal for a photovoltaic device. The nanostructures at the particle surface may increase light absorption due to increased light scattering events and a refractive index gradient formed by the nano- and microstructures on the powder surface. The functionalized powder particle may absorb light over a broader bandwidth and at a greater range of angles due to its surface morphology and structure. The increased efficiency of light absorption is not exclusive to any particular nanostructure and may be caused by several variants of functionalized powder particles.

Photo-detecting devices: In some examples, one or more functionalized powder particles may be used as an additive or component of a photo-detecting device. The nanostructures at the particle surface may increase light absorption due to increased light scattering events and a refractive index gradient formed by the nano- and microstructures on the powder surface. The functionalized powder particle may absorb light over a broader bandwidth and at a greater range of angles due to its surface texture and structure. The increased efficiency of light absorption is not exclusive to any particular nanostructure and may be caused by several variants of functionalized powder particles.

Photo-emitting devices: In some examples, one or more functionalized powder particles may be used as an additive or component in light-emitting devices. For example, one or more grains of a functionalized powder may comprise a light-emitting diode (LED) device. Light extraction is an important aspect of LED efficiency because a large difference in refractive index between a light-emitting material and air can result in high internal reflection. The nanostructures on the surface of a functionalized powder particle may provide a refractive index gradient due to the material density gradient at the particle surface, decreasing the amount of internal reflection between the LED material and air interface. For example, a porous pyramid structure on the powder surface would provide a material density gradient. A broad range of surface nano- and microstructures may be used for LED applications and is not limited to the aforementioned structure.

Non-limiting examples: One or more functionalized particles of the present disclosure may be incorporated into a number of articles, including, but not limited to, keyboards, computers, computer peripherals, computer mouse, film with pressure sensitive adhesive backing, containers, bottles, utensils, cookware, kitchenware, curtains, beverage dispensers, shopping carts, hydration packs, bladders, valves, tubing, and bags, fluid pipes, sewage pipes, gas pipes, footwear, phones and peripherals, video game consoles and controllers, manned and unmanned vehicles, tires, buttons, vents, handrails, trains, window shades, cutting boards, drying racks, fluid tanks, drains, tubing, filters, traps, nets, aquatic, marine, and amphibious vehicles, refrigerators, freezers, biometric readers and scanners, such as finger and palm print readers, propellers, humidifier, dehumidifier, shower mats, athletic, gym, and yoga mats, athletic equipment, liquid dispensers, handles and knobs, automated teller machines, credit cards and other plastic cards, litterboxes, pet bowls, pet carriers, mass transit, electronics, tiles, showers, toilets, trash and recycling receptacles, rails, floors, ceilings, walls, seat covers, tables, counters, chairs, cabinets, switches and switch plates, food preparation surfaces, food wraps, hair dressing tools and equipment, such as combs, brushes, razors and scissors, sinks, fluid taps, basins, bench tops, shelves, processing and packaging devices and machines, food and beverage processing and production equipment, abattoirs, clothing, eyewear, bags, surfaces of aquatic and marine installations such as jetty, pier and pontoon pillars, maritime and aquatic pipes and cables, oil and gas installations, aircraft, military vehicles, military equipment and gear, siding, building materials, concrete, textiles/fabric, firearms, paint, surface coatings, wetsuits, aquatic equipment, lighting, solar cells, HVAC, telescopes, cameras and lenses, optical devices, photodetectors, tools, masks, grips, watches, coolers, two-way radio, lockers, storage bins, dumpster, packaging, squeegee, footings, currency, musical instruments and equipment, textile equipment, fishing equipment, jewelry, cutlery, locks, clothes washers and dryers, ovens, dishwashers, stoves, TVs, carpets and carpeting, rugs, tactical gear, pens, pencils, other writing implements, office supplies, furniture, artwork, roofing, automobiles, medical equipment and devices, dental equipment and devices, bandages, cribs, pacifiers, trays, toys, baby bottles and accessories, thermometers, changing tables and covers, high chairs, breast pumps, fuel pumps, electric charging stations, cords, bicycles, motorcycles, remote controllers, mattresses, aquatic pool and peripherals, walkers/canes, school supplies, playground equipment, cafeteria equipment, hoses, tents, rain flies and tarps, umbrellas, gutters, grills, smokers, smoking apparatus, rubber articles, plastic articles, appliances, speakers, condoms, toothbrush holders, sponges, towels, pumps, rope, biological analysis device, biological cell component extraction/harvesting device, gloves, architectural components, office equipment, packaging, conveyer belts, manufacturing equipment, scooters, drones, cases, metal articles, glass articles, ceramic articles, books, restaurant menus, paper and paper goods, utility cables, placemats, protective coverings, and signage. The article may be selected from office supplies, office equipment, electronics, containers, kitchenware, cookware, housewares, textiles, hardware, consumer products, vehicles and vessels, filters, pumps, aquatic equipment, surfaces, furniture, appliances, devices, building materials, military equipment, tools, solar cells, currency, medical supplies, medical devices, paper goods, manufacturing equipment, food processing equipment and optical equipment. Optionally, the article comprises rubber, plastic, metal, glass or ceramic.

Methods of Fabricating Composite Articles

Conventional techniques may be used to coat an article with one or more functionalized particles of the present disclosure. For example, an adhesive, binder or similar material may be used to attach at least one functionalized particle to an article. Functionalized powder particles may be fully exposed, partially exposed or fully embedded in an adhering medium on the article surface.

Method for embedding functionalized particles in a thermoplastic: One or more functionalized powder particles may be added to thermoplastics. In some examples, one or more heated functionalized powder particles may be added to the surface of a heated thermoplastic. The elevated temperature of the thermoplastic and the functionalized particles allows the thermoplastic to adsorb onto the particle surface. Optionally, the thermoplastic may comprise the functionalized powder particle in the bulk. The thermoplastic is allowed to solidify so that particles are partially adsorbed or fully absorbed into the plastic medium. Optionally, a plastic solvent may be used to temporarily liquefy or melt the plastic. Optionally, powder coating, electrostatic spraying, or roll-to-roll methods may be used to add functionalized particles to thermoplastics. Methods of adding functionalized particles to thermoplastics is not limited to the aforementioned methods.

Method for embedding functionalized particles in a molded material: In some examples, one or more functionalized powder particles are temporarily secured to the interior surface of a mold or template. The mold or template is filled with a liquid or pliable material, including glass, ceramic, concrete, elastomer or metal. The molded or templated material is allowed to solidify then the mold or template is removed. In some examples, the molded or templated material will retain one or more functionalized powder particles, which are embedded on the material surface. Optionally, the molded or template material may retain no particles but will retain impressions of the surface nanostructures of one or more functionalized powder particles. In other examples, the molded or templated material will retain the nanostructured portions of one or more functionalized powder particles while the original mold or template will retain the bulk portion of the powder particle.

EXAMPLES

Example 1: A crystalline Si powder, 99.995% pure, 10.0 g, with a particle size range between 10 μm and 150 μm, and an average particle size of 28 μm, is suspended via stirring in a bath of acetone for 10 minutes. The acetone bath is then sonicated for 10 minutes. The acetone/Si powder mixture is filtered and the Si powder is transferred into a methanol bath. The crystalline Si powder is suspended via stirring in a bath of methanol for 10 minutes. The methanol bath is then sonicated for 10 minutes. The methanol/Si powder mixture is filtered and rinsed with DI-$H_2O$. The powder is transferred and suspended via stirring into a solution of DI-$H_2O$ and 1.5 M HF for 5 minutes to remove the native oxide. The powder is then filtered and rinsed with DI-$H_2O$. The Si powder is then subjected to metal-assisted chemical etching (MACE). The Si powder is suspended via stirring in a solution of 0.15 M HF, 0.035 M $AgNO_3$ and DI-$H_2O$ for 8 minutes to deposit Ag nanoparticles on the surface of the powder particles. The powder is then filtered and transferred to a solution of 5.5 M HF, 2 M $H_2O_2$, and DI-$H_2O$ and suspended via stirring for 30 minutes at an initial bath temperature of 25° C. This reaction is exothermic and therefore the bath temperature may increase and accelerate the etching rate. After the MACE process, the Si powder is filtered and then thoroughly rinsed with DI-$H_2O$ and then may be flushed with nitrogen gas to remove residual moisture. The resultant material is a Si powder with a nanostructured surface.

Example 2: A functionalized Si powder is prepared via the method described in Example 1. The functionalized Si particles are then subject to a bath of 7 M $HNO_3$ and DI-$H_2O$ for 5 minutes to remove and recover the Ag from the Si particles. The Si powder is given a final rinse with DI-$H_2O$ and then may be flushed with nitrogen gas to remove residual moisture. The resultant material is a Si powder with a nanostructured surface. The recovered metal may be recycled for further use.

Example 3: A crystalline Si powder, 99.995% pure, 10.0 g, with a particle size range between 10 μm and 150 μm, and an average particle size of 28 μm, is suspended via stirring in a bath of acetone for 10 minutes. The acetone bath is then sonicated for 10 minutes. The acetone/Si powder mixture is filtered and the Si powder is transferred into a methanol bath. The crystalline Si powder is suspended via stirring in a bath of methanol for 10 minutes. The methanol bath is then sonicated for 10 minutes. The methanol/Si powder mixture is filtered and rinsed with DI-$H_2O$. The powder is transferred and suspended via stirring into a solution of DI-$H_2O$ and 1.5 M HF for 5 minutes to remove the native oxide. The powder is then filtered and rinsed with DI-$H_2O$. The Si powder is then subjected to MACE. The Si powder is suspended via stirring in a solution of 0.15 M HF, 0.035 M $AgNO_3$ and DI-$H_2O$ for 8 minutes to deposit Ag nanoparticles on the surface of the powder particles. The powder is then filtered and transferred to a solution of 5.5 M HF, 2 M $H_2O_2$, and DI-$H_2O$ and suspended via stirring for 25 minutes at an initial bath temperature of 25° C. This reaction is exothermic and therefore the bath temperature may increase and accelerate the etching rate. After the MACE process, the Si powder is filtered and then thoroughly rinsed with DI-$H_2O$.

The Si powder is then subjected to a subsequent round of MACE. The Si powder is suspended via stirring in a solution of 0.15 M HF, 0.035 M $AgNO_3$ and DI-$H_2O$ for 0.5 minutes to deposit additional Ag nanoparticles on the surface of the powder particles. The powder is then filtered and transferred to a solution of 5.5 M HF, 2 M $H_2O_2$, and DI-$H_2O$ and suspended via stirring for 15 minutes at an initial bath temperature of 25° C. This is reaction is exothermic and therefore the bath temperature may increase and accelerate the etching rate. After MACE, the Si powder is given a final rinse with DI-$H_2O$ and then may be flushed with nitrogen gas to remove residual moisture. The resultant material is a Si powder with a nanostructured surface.

Example 4: A functionalized Si powder is prepared via the method described in Example 3. The functionalized Si particles are then subject to a bath of 7.85 M $HNO_3$ and DI-$H_2O$ for 5 minutes to remove and recover the Ag from the Si particles. The Si powder is given a final rinse with DI-$H_2O$ and is then placed in a vacuum chamber to remove residual moisture. The resultant material is a Si powder with a nanostructured surface. The recovered metal may be recycled for further use.

Example 5: A crystalline Si powder with a particle size range between 10 μm and 200 μm is suspended via stirring in a bath of acetone for 10 minutes. The acetone bath is then sonicated for 10 minutes. The acetone/Si powder mixture is filtered and then Si powder is transferred into a methanol bath. The crystalline Si powder is suspended via stirring in a bath of methanol for 10 minutes. The methanol bath is then sonicated for 10 minutes. The methanol/Si powder mixture is filtered and then powder is moved into a vacuum oven where it is heated at 80° C. for at least one hour. The Si powder is then subjected to chemical etching (CE). The Si powder is stirred in a solution of 1.0 M KOH and DI-$H_2O$ at an initial bath temperature of 50° C. for 20 minutes. This is reaction is exothermic and therefore the bath temperature may increase and accelerate the etching rate. The resultant powder morphology and etch rate are dependent on the bath temperature, duration, and agitation. Agitating the solution reduces thermal gradients in the bath, which may result in more homogenous functionalization between particles. Optionally, a static bath may result in functionalized particles that are heterogeneously structured between particles and may be favorable for fabricating a distribution of structurally functionalized particles in a single batch. After the CE process, the Si powder is filtered and thoroughly rinsed with deionized water.

The Si powder is then subjected to MACE. The Si powder is suspended via stirring in a solution of 0.20 M HF, 0.05 M $AgNO_3$ and DI-$H_2O$ for 5 minutes to deposit Ag nanoparticles on the surface of the powder particles. The powder is then filtered and transferred to a solution of 5.5 M HF, 2 M $H_2O_2$, and DI-$H_2O$ and suspended via stirring for 30 minutes at an initial bath temperature of 25° C. This is reaction is exothermic and therefore the bath temperature may increase and accelerate the etching rate. After the MACE process, the Si powder is filtered and then thoroughly rinsed with DI-$H_2O$. The Si particles are then subject to a bath of 7.85 M $HNO_3$ and DI-$H_2O$ for 5 minutes to remove and recover the Ag from the Si particles. The Si powder is given a final rinse with DI-$H_2O$ and is then placed in a vacuum chamber to remove residual moisture. The resultant material is a Si powder with a nanostructured surface.

Example 6: A crystalline Si powder, 99.995% pure, 10.0 g, with a particle size range between 10 μm and 150 μm, and an average particle size of 28 μm, is sonicated and suspended via stirring in a bath of acetone and then methanol for 15 minutes each to remove organic contaminants. The cleaned Si powder is filtered and rinsed with DI-$H_2O$. The powder is transferred to a filter reactor vessel and suspended via stirring at 400 rpm in a solution of DI-$H_2O$ and 1.35 M HF for 5 minutes to remove the native oxide. The solution is then evacuated from the vessel. The Si powder is then subjected to MACE. The Si powder is suspended via stirring at 400 rpm in a solution of 0.15 M HF, 0.035 M $AgNO_3$ and DI-$H_2O$ to deposit Ag nanoparticles on the surface of the powder particles. The solution is then evacuated from the vessel after 8 minutes. The powder is then etched in a static etch solution, initially at 25° C., that comprises 48% w/w HF, 30% w/w $H_2O_2$, and DI-$H_2O$ (1:1:3 v/v). The $H_2O_2$ is added continuously over the initial 10 minutes. The etching duration, chemical concentrations, temperature, and the rate of adding $H_2O_2$ are varied depending on the intended resultant nanostructured Si powder. The etch solution is evacuated from the vessel and then the powder is rinsed with DI-$H_2O$ or ethanol. Optionally, the powder is then subject to a bath of 7.85 M $HNO_3$ and DI-$H_2O$ for 5 minutes to remove and recover the Ag from the functionalized particles. The recovered metal may be recycled for further use. The powder is given a final rinse with DI-$H_2O$ or ethanol and is then placed in an oven at 50° C. or vacuum chamber to remove residual moisture. FIG. 4 shows an example of the resultant nanowire surface that was formed after 60 minutes of etching.

Example 7: A crystalline Si powder, 99.995% pure, 10.0 g, with a particle size range between 10 µm and 150 µm, and an average particle size of 28 µm, is sonicated and suspended via stirring in a bath of acetone and then in a bath of methanol for 15 minutes each to remove organic contaminants. The cleaned Si powder is filtered and rinsed with DI-$H_2O$. The powder is transferred to a filter reactor vessel and suspended via stirring at 400 rpm in a solution of DI-$H_2O$ and 1.35 M HF for 5 minutes to remove the native oxide. The solution is then evacuated from the vessel. The Si powder is then subjected to MACE. The Si powder is suspended via stirring at 400 rpm in a solution of 0.15 M HF, 0.035 M $AgNO_3$ and DI-$H_2O$ to deposit Ag nanoparticles on the surface of the powder particles. The solution is then evacuated from the vessel after 8 minutes. The powder is then suspended in an etch solution, initially at 25° C., via stirring at 250 rpm. The powder containing solution is agitated such that a film or foam or crust is prevented from forming at the solution/air interface. A film, foam, or crust may result in functionalized particles that are non-homogenous between particles. The etch solution comprises 48% w/w HF, 30% w/w $H_2O_2$, and DI-$H_2O$ (1:1:3 v/v) and $H_2O_2$ is added continuously over the initial 10 minutes. The etching duration, chemical concentrations, temperature, agitation rate, and the rate of adding $H_2O_2$, may be varied depending on the intended resultant nanostructured Si powder. FIGS. 5C-5D, 16A-16C, and, 17A-17B, show examples of the resultant nanostructured surface for etching durations of 30, 60, and 90 minutes, respectively. The etch solution is evacuated from the vessel and then the powder is rinsed with DI-$H_2O$ or ethanol. Optionally, the powder is suspended via stirring at 250 rpm in a solution of 7.85 M $HNO_3$ and DI-$H_2O$ for 5 minutes to remove and recover the Ag from the functionalized particles. The solution is evacuated from the vessel and then powder is given a final rinse with DI-$H_2O$ or ethanol.

Figure 16C:
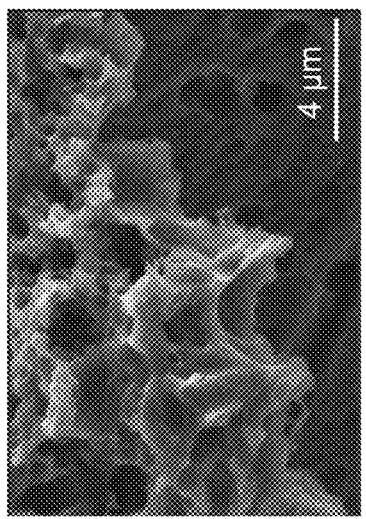
FIGS. 16A-16C show SEM images of morphology comprising coral structures. The particles were synthesized via Ag-MACE of Si crystalline particles. These morphologies have been demonstrated to have antimicrobial properties.
Figure 16B:
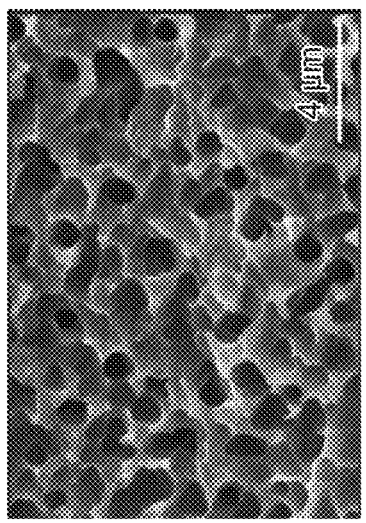
Figure 16A:
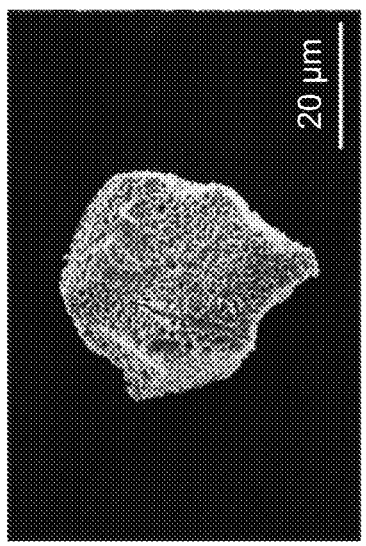
Figures 17A, 17B:
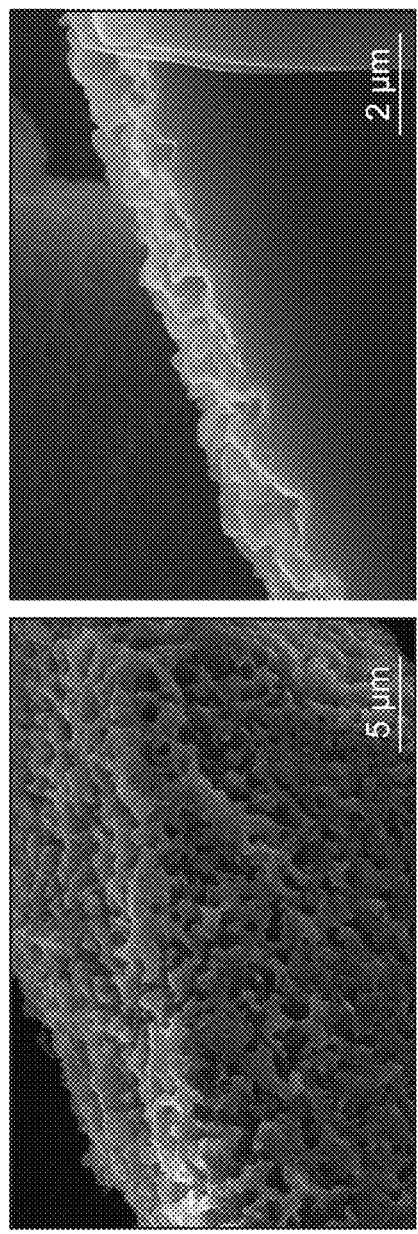
FIGS. 17A-17B show SEM images of morphology comprising coral structures. The particles were synthesized via Ag-MACE of Si crystalline particles.

The motion of the etch solution has a significant impact on the resultant nanostructure. For example, the nanostructures shown in FIGS. 4 and 16A-16C were fabricated from the procedure described in Example 6 and above (Example 7). Except for not stirring (Example 6) and stirring (Example 7) the etching solution, the etching conditions and duration are identical. However, FIG. 4 shows a morphology comprising nanowires, while FIGS. 16A-16C show a morphology comprising coral structures. Additionally, the resulting etch depth (distance between the surface and the outer edge of the unetched solid particle core), for the same duration, is 10 times deeper when the etching solution is static than when it is stirred at 250 rpm, as seen in FIG. 32. Consequently, the etch depth rate (etch depth/time) is about 10 times greater when the etching solution is static than when it is stirred at 250 rpm. In the static case, the Ag-nanoparticles migrate from the surface of the Si particle toward the particle core along a relatively straight path, which forms the high-aspect ratio nanowires shown in FIG. 4. Whereas the agitation and motion during etching introduces additional forces on the Ag-nanoparticle during its migration into the Si particle, which may alter the migration and the resultant etched structure. As seen in FIGS. 16A-16C, stirring may result in low-aspect ratio irregular coal structures.

The nanowire structures formed via the method described in Example 6 are structurally more delicate than the structures formed via the method described in Example 7. For example, stirring the particles, separately, in solution at 250 rpm for 5 minutes resulted in significant damage and loss of nanowires from the Example 6 particles. Whereas the interconnected structures found on the Example 7 particles showed no noticeable degradation due to being stirred in solution or from normal handling. Additionally, FIG. 4 shows a particle that was not subject to additional stirring, however, sections of the particle surface are missing nanowires (the functional structure), which were broken off from normal handling. The interconnected structural features found in structures, such as but not limited to hoodoos and corals, provide mechanical durability.

FIGS. 25A-25B show X-ray diffraction data from functionalized powder particles after 90 minutes of etching as well as nonfunctionalized Si particles for comparison. Shifts in peak position are seen for the Si(111) and Si(311) peaks for the functionalized powder, which indicates a 0.194% lattice expansion along the <111> direction and a 0.143% contraction along <311> directions, respectively. Whereas the positions for the Si(220), Si(400), and Si(331) peaks remain unchanged. This X-ray data suggests that the crystalline unit cell is anisotropic deformed due to the structural functionalization of the particle.

Figure 28:
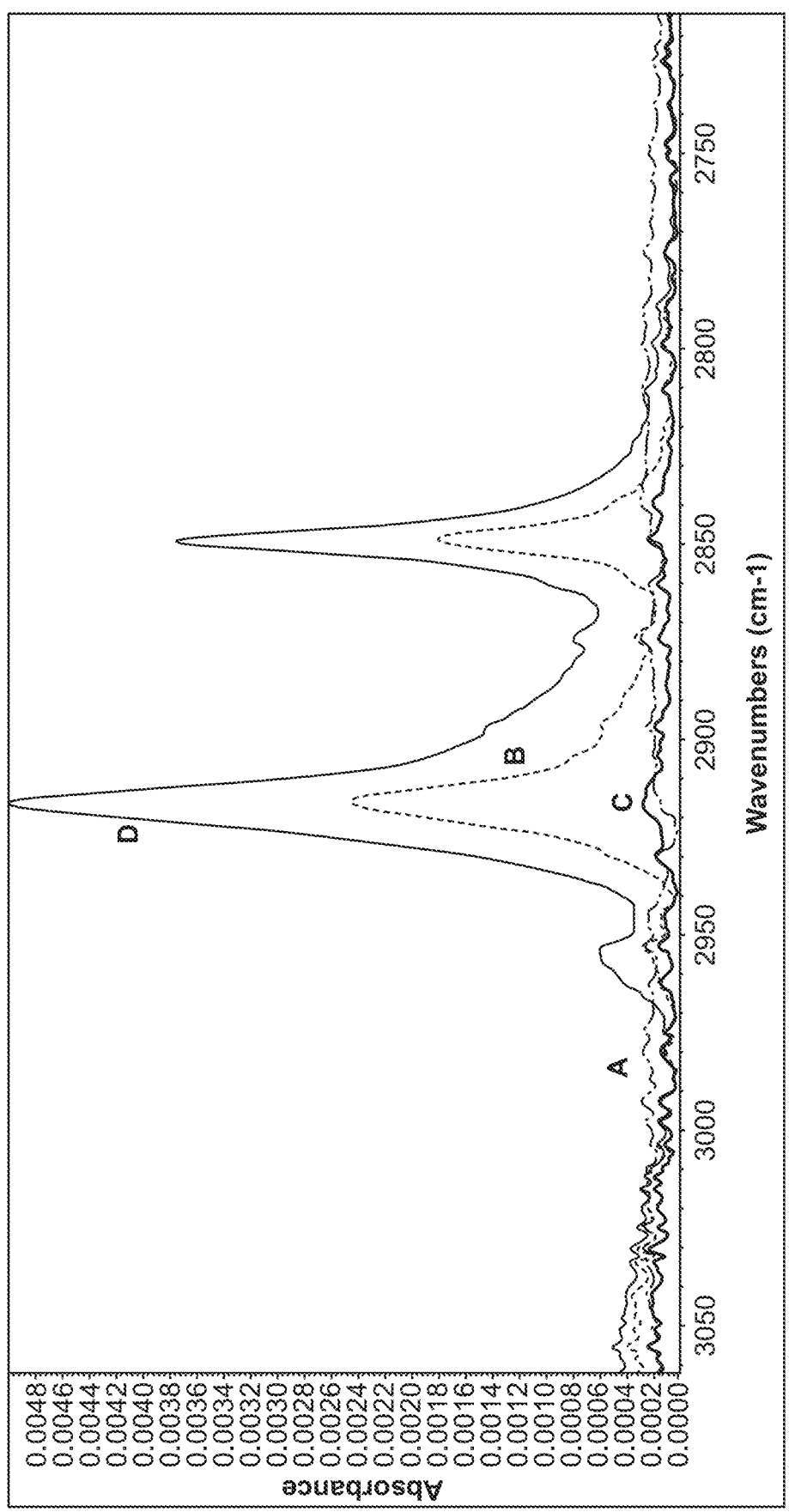
FIG. 28 shows attenuated-total reflectance infrared spectra, measured with a Nicolet iS50 FT-IR spectrometer, of the symmetric and asymmetric vibrational C—H modes for (A) nonfunctionalized Si powder, (B) chemically functionalized Si powder, (C) structurally functionalized Si powder, and (D) chemically and structurally functionalized Si powder.

Example 8: A functionalized Si powder is prepared via the method described in Example 7, with an etch duration of 90 minutes. The powder is added to $H_2SO_4$ and $H_2O_2$ (4:1 v/v) for 25 minutes to remove organic residues and prepare silanol groups on the surface. The powder is filtered, thoroughly rinsed with DI-$H_2O$, then dried in at 75° C. for 30 minutes. The powder is added to a 2.5 mM octadecyltrichlorosilane solution prepared in toluene and allowed to react for 120 minutes. The chemically functionalized powder is then removed from the solution by filtration and rinsed with chloroform. FIG. 28 shows attenuated total reflectance Fourier transform infrared spectra (ATR-FTIR) for the chemically and structurally functionalized Si powder (Sample D), the structurally functionalized Si powder (Sample C), chemically functionalized Si powder (Sample B), and nonfunctionalized Si powder (Sample A). Based on the peak positions for the symmetric and asymmetric C—H stretches, the two chemically functionalized powders (Samples B and D) both show well-ordered monolayer formations. However, at least a threefold increase absorbance is seen for the structurally and chemically functionalized powder (Sample D), which corresponds to a greater number of functional molecules per particle as a result of the higher surface area of the structurally functionalized particle. Additionally, this result indicates that the structurally functionalized particles (Samples C and D) have at least three times the surface area than the nonfunctionalized Si particles (Samples A and B). The chemical functionalization may further increase the hydrophobicity of the structurally functionalized particle. Generally, structurally functionalized particles may allow greater amounts of chemical functionalization per particle due to the greater surface area than nonfunctionalized particles.

Example 9: A crystalline Si powder, 99.995% pure, 10.0 g, with a particle size range between 10 µm and 150 µm and, an average particle size of 45 µm, is sonicated and suspended via stirring in a bath of acetone and then methanol for 15 minutes each to remove organic contaminants. The cleaned Si powder is filtered and rinsed with DI-$H_2O$. The powder is transferred to a filter reactor vessel and suspended via stirring at 400 rpm in a solution of DI-$H_2O$ and 1.35 M HF for 5 minutes to remove the native oxide. The solution is then evacuated from the vessel. The Si powder is then subjected to one-step MACE. The Si powder is suspended via stirring at 250 rpm in a solution of 4.6 M HF, 0.55 M $H_2O_2$, 0.035 M $Cu(NO_3)_2 \cdot 2.5H_2O$ and DI-$H_2O$ to deposit Cu nanoparticles on the surface of the powder particles and etch the particles. The solution is initially at 25° C. The etching duration, chemical concentrations, temperature, and stirring rate may be varied depending on the intended resultant nanostructured Si powder. FIGS. 20A-20B show examples of the resultant nanostructured surface for etching durations of 30 and 10 minutes, respectively. The etch solution is evacuated from the vessel and then the powder is rinsed with DI-$H_2O$ or ethanol. Optionally, the powder is suspended via stirring at 250 rpm in a solution of 7.85 M $HNO_3$ and DI-$H_2O$ for 5 minutes to remove and recover the Cu from the functionalized particles. The recovered metal may be recycled for further use. The solution is evacuated from the vessel and then powder is given a final rinse with DI-$H_2O$ or ethanol.

Example 10: A crystalline Si powder, 99.995% pure, 10.0 g, with a particle size range between 10 μm and 150 μm, and an average particle size of 45 μm, is sonicated and suspended via stirring in a bath of acetone and then in a bath of methanol for 15 minutes each to remove organic contaminants. The cleaned Si powder is filtered and rinsed with DI-$H_2O$. The powder is then suspended in an etch solution, initially at 25° C., via stirring at 250 rpm. The powder containing solution is agitated such that a film or foam or crust is prevented from forming at the solution/air interface. The etch solution consists of 6.7 M KOH and DI-$H_2O$. The temperature of the solution increased over the course of the reaction and after 9 minutes the temperature measured by an IR thermometer at the top surface of the solution was 55° C. The etching duration, chemical concentration, and solution temperature may be varied depending on the intended resultant nanostructured Si powder. FIG. 21 shows examples of the resultant nanostructured surface produced after 9 minutes. The etch solution is evacuated from the vessel and then the powder is rinsed with DI-$H_2O$ or ethanol.

Example 11: A crystalline Si powder, 99.995% pure, 10.0 g, with a particle size between 75 and 150 μm is sonicated and suspended via stirring in a bath of acetone and then in a bath of methanol for 15 minutes each to remove organic contaminants. The cleaned Si powder is filtered and rinsed with DI-$H_2O$. The powder is then suspended in an etch solution via stirring at 250 rpm. The etch solution consists of 5% (w/w) NaOH and DI-$H_2O$, initially at 60° C. The temperature, measured by an IR thermometer at the top surface of the solution, increased over the course of the first 5 minutes with a maximum temperature of 71° C. and then decreased over the next 55 minutes to a final temperature of 33° C. The etching duration, chemical concentrations, and solution temperature may be varied depending on the intended resultant structured Si powder. FIGS. 22A-22B show the resultant nanostructured surface produced after 15 minutes. The particles are removed by filtration and the powder is rinsed with DI-$H_2O$ or ethanol.

Example 12: A crystalline Si powder, 99.995% pure, 10.0 g, with a particle size between 75 and 150 μm is sonicated and suspended via stirring in a bath of acetone and then in a bath of methanol for 15 minutes each to remove organic contaminants. The cleaned Si powder is filtered and rinsed with DI-$H_2O$. The powder is then suspended in an etch solution via stirring at 250 rpm. The powder containing solution is agitated such that a film or foam or crust is prevented from forming at the solution/air interface. The etch solution consists of 1% (w/w) KOH and DI-$H_2O$, initially at 60° C., and is not heated thereafter. The etching duration, chemical concentrations, and solution temperature may be varied depending on the intended resultant structured Si powder. The solution is evacuated from the vessel after 70 minutes and the powder washed with DI-$H_2O$ which is then evacuated from the vessel. The Si powder is then subjected to MACE. The functionalized Si powder is suspended via stirring at 400 rpm in a solution of 0.15 M HF, 0.035 M $AgNO_3$, and DI-$H_2O$ to deposit Ag nanoparticles on the surface of the functionalized powder particles. The solution is then evacuated from the vessel after 8 minutes. The powder is then suspended in an etch solution, initially at 25° C., via stirring at 250 rpm. This reaction is exothermic, and the peak temperature measured by an IR thermometer at the top surface of the solution is 85° C., at 5 minutes. The powder containing solution is agitated such that a film or foam or crust is prevented from forming at the solution/air interface. The etch solution comprises 48% w/w HF, 30% w/w $H_2O_2$, and DI-$H_2O$ (1:1:3 v/v) and $H_2O_2$ is added continuously over the initial 9 minutes. The etching duration, chemical concentrations, solution temperature, and agitation rate may be varied depending on the intended resultant micro and nano-structured Si powder. FIG. 23 shows the resultant heterofunctionalized surface produced after 15 minutes. The solution is evacuated from the vessel and the powder is rinsed with DI-$H_2O$ or ethanol. Optionally, the powder is suspended via stirring at 250 rpm in a solution of 7.85 M $HNO_3$ and DI-$H_2O$ for 5 minutes to remove and recover the Ag from the functionalized particles. The recovered metal may be recycled for further use. The solution is evacuated from the vessel and then powder is given a final rinse with DI-$H_2O$ or ethanol.

Example 13: Amorphous SiO powder, 99% pure, 10.0 g, with a particle size range between 38 and 45 μm, is transferred to a filter reactor vessel. The SiO powder is then subjected to MACE. The SiO powder is suspended via stirring at 400 rpm in a solution of 0.15 M HF, 0.035 M $AgNO_3$ and DI-$H_2O$ to deposit Ag nanoparticles on the surface of the powder particles. The solution is then evacuated from the vessel after 8 minutes. The powder is then suspended in an etch solution, initially at 25° C., via stirring at 250 rpm. This reaction is exothermic, and the peak temperature measured by an IR thermometer at the top surface of the solution is 83° C., at 2 minutes. The powder containing solution is agitated such that a film or foam or crust is prevented from forming at the solution/air interface. The etch solution comprises 48% w/w HF, 30% w/w $H_2O_2$, and DI-$H_2O$ (1:1:3 v/v) and $H_2O_2$ is added continuously over the initial 7.5 minutes. The etching duration, chemical concentrations, solution temperature, and agitation rate may be varied depending on the intended resultant nanostructured SiO powder. FIGS. 33A-33D show examples of the resultant nanostructured surface for an etching duration of 60 minutes. The etch solution is evacuated from the vessel and then the powder is rinsed with DI-$H_2O$ or ethanol. Optionally, the powder is suspended via stirring at 250 rpm in a solution of 7.85 M $HNO_3$ and DI-$H_2O$ for 5 minutes to remove and recover the Ag from the functionalized particles. The recovered metal may be recycled for further use. The solution is evacuated from the vessel and then powder is given a final rinse with DI-$H_2O$ or ethanol.

Figure 26:
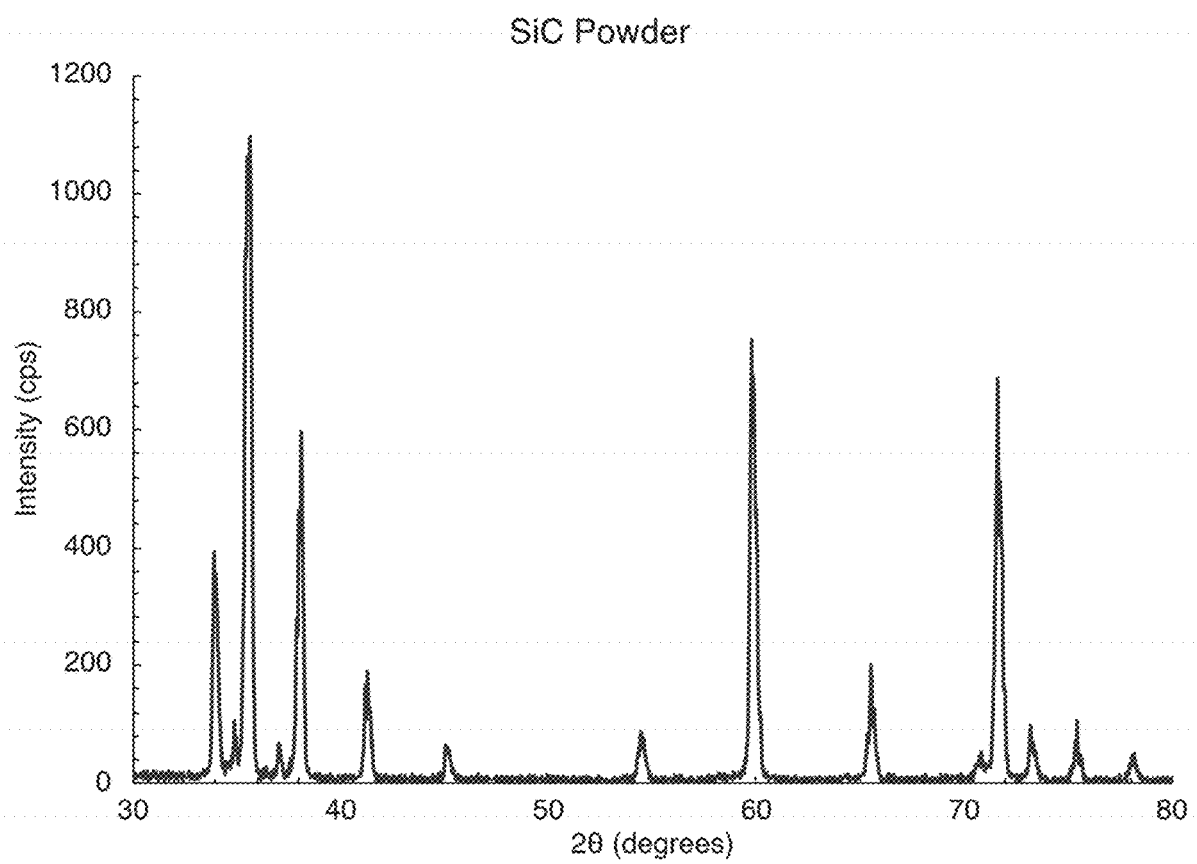
FIG. 26 shows X-ray (Cu Kαi) powder diffraction data for nonfunctionalized crystalline SiC powder (40 µm average diameter) containing both α- and β-crystal types, measured with a Rigaku Ultima IV 3 kW X-ray diffractometer system.

Example 14: A crystalline SiC powder, 99% pure, 3.0 g, consisting of α- and β-phases as shown by X-ray diffraction in FIG. 26, with an average particle sizes of 40 μm, is transferred to a reactor vessel that comprises 48% w/w HF and $HNO_3$ (3:1 v/v), initially heated to 80° C. and maintained between 75-100° C. The powder is then suspended in an etch solution via stirring at 241 rpm. The powder containing solution is agitated such that a film or foam or crust is prevented from forming at the solution/air interface. The etching duration, chemical concentrations, solution temperature, and agitation rate may be varied depending on the intended resultant nanostructured SiC powder. FIGS. 24A-24B show examples of the resultant nanostructured surface for etching 150 minutes. The particles are removed by filtration and the powder is rinsed with DI-$H_2O$ or ethanol.

Example 15: A crystalline Ge powder, 99.999% pure, 3.3 g, with a particle size smaller than 150 μm is transferred to a reactor vessel and suspended via stirring at 400 rpm in a solution of DI-$H_2O$ and 1.35 M HF for 5 minutes to remove the native oxide. The solution is then removed from the vessel. The Ge powder is then subjected to MACE. The Ge powder is suspended via stirring at 400 rpm in a solution of 0.14 M HF, 0.035 M $AgNO_3$ and DI-$H_2O$ to deposit Ag nanoparticles on the surface of the powder particles. The solution is then removed from the vessel after 8 minutes. The powder is then suspended in an etch solution, initially at 25° C., via stirring at 250 rpm. This reaction is exothermic, and the temperature measured by an IR thermometer at the top surface of the solution is 55° C., at 12 minutes. The powder containing solution is agitated such that a film or foam or crust is prevented from forming at the solution/air interface. The etch solution comprises 48% w/w HF, 30% w/w $H_2O_2$, and DI-$H_2O$ (1:1:3 v/v) and $H_2O_2$ is added continuously over the initial 6 minutes. The etching duration, chemical concentrations, solution temperature, and agitation rate may be varied depending on the intended resultant nanostructured Ge powder. FIGS. 35 and 36A-36B show the resultant functionalized surface for an etching duration of 5 minutes. The etch solution is removed from the vessel and then the powder is rinsed with DI-$H_2O$ or ethanol. Optionally, the powder is suspended via stirring at 250 rpm in a solution of 7.85 M $HNO_3$ and DI-$H_2O$ for 5 minutes to remove and recover the Ag from the functionalized particles. The recovered metal may be recycled for further use. The solution is evacuated from the vessel and then powder is given a final rinse with DI-$H_2O$ or ethanol.

Figure 38A:
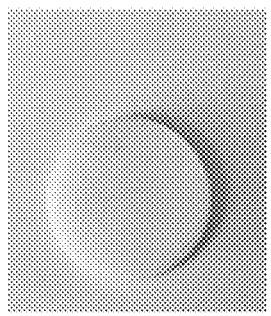
Figure 38B:
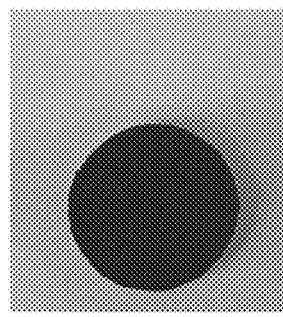
Figure 38C:
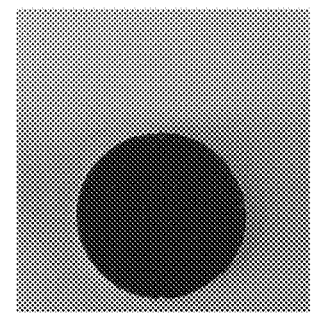
Figure 38D:
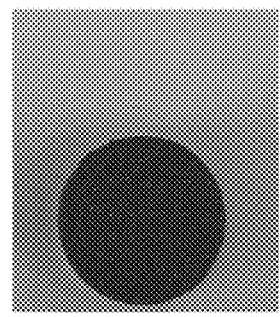

Example 16: A functionalized powder is prepared via the method described in Example 1, 2, 3, 4, 5, 6, 7, 8, 9, 10, 11, 12, 13, 14, or 15. The functionalized powder is affixed to a plastic by temporarily liquifying the plastic with a chemical solvent. Examples of the plastic solvent include, but are not limited to, dichloromethane, benzene, toluene, n-hexane, hexanes, petroleum ether, acetone, acetalaldehyde, methanol, analine, carbon tetrachloride, cyclohexane, diethyl ether, xylene, methyl ethyl ketone, methyl acetate, trichloroethylene, methyl methacrylate monomer. The solvent and functionalized powder may be applied to the plastic in any order or simultaneously. The solvent is then allowed to evaporate, and the plastic is allowed to solidify. As illustrated in FIGS. 9B-9C, the resultant composite consists of functionalized powder affixed to plastic surface and/or within the bulk, which may have a complex geometry or shape (in comparison, structurally functionalized rigid wafers would not be able to conform to complex surface shapes). The functionalized powder surface may be partially exposed at the plastic/atmosphere interface. FIG. 38A shows a bare ABS plastic substrate while FIGS. 38B-38D show example functionalized surfaces comprising ABS plastic substrates that have been coated with functionalized particles via plastic solvents. Optionally, the powder may be electrostatically applied to the surface of the plastic.

Example 17: A functionalized powder is prepared via the method described in Example 1, 2, 3, 4, 5, 6, 7, 8, 9, 10, 11, 12, 13, 14, or 15. The plastic is heated, temporarily melting the plastic. Subsequently the functionalized powder is deposited, and the plastic is allowed to solidify, affixing the powder to and/or in the article. As illustrated in FIGS. 9B-9C, the resultant bulk and/or surface composite consists of functionalized powder affixed to a plastic surface and/or within the bulk. The functionalized powder surface may be partially exposed at the plastic/atmosphere interface. Optionally, the powder may be electrostatically applied to the surface of the plastic.

Example 18: A functionalized powder is prepared via the method described in Example 1, 2, 3, 4, 5, 6, 7, 8, 9, 10, 11, 12, 13, 14, or 15. A binder medium is applied to the surface of an article. The binder may be applied through spraying, rolling, coating, brushing, stamping or any other deposition technique. The functionalized powder is deposited on the binder medium, leaving behind a coated article that may have partially exposed functionalized powder particles at the surface/atmosphere interface, as illustrated in FIG. 9A. Optionally, paint may be used as the binder medium.

Example 19: A functionalized powder is prepared via the method described in Example 1, 2, 3, 4, 5, 6, 7, 8, 9, 10, 11, 12, 13, 14, or 15. Acrylic paint or another polymer paint (or coating) is applied to the surface of an article. Subsequently, the functionalized powder is affixed to a painted surface by temporarily liquifying the paint with a chemical solvent. Examples of the plastic solvent include, but are not limited to, dichloromethane, benzene, toluene, hexane, hexanes, petroleum ether, acetone, acetalaldehyde, methanol, analine, carbon tetrachloride, cyclohexane, diethyl ether, xylene, methyl ethyl ketone, methyl acetate, trichloroethylene, methyl methacrylate monomer. The solvent and functionalized powder may be applied to the painted surface in any order or simultaneously. The solvent is then allowed to evaporate, and the paint is allowed to solidify. The resultant composite consists of functionalized powder affixed to the painted surface. The surface of the functionalized powder may be partially exposed at the paint/atmosphere interface, as illustrated in FIG. 9A. Optionally, the powder may be electrostatically applied to the surface of the paint.

Example 20: A functionalized powder is prepared via the method described in Example 1, 2, 3, 4, 5, 6, 7, 8, 9, 10, 11, 12, 13, 14, or 15. The functionalized powder is suspended into a metal-adhering paint via stirring. The paint is applied in a thin layer to the working surface of a set of a medical device or equipment. The paint is allowed to dry, leaving behind a painted metal surface with partially exposed functionalized powder particles exposed at the paint/atmosphere interface, as illustrated in FIG. 9A.

Example 21: A functionalized powder is prepared via the method described in Example 1, 2, 3, 4, 5, 6, 7, 8, 9, 10, 11, 12, 13, 14, or 15. The functionalized powder is temporarily secured to the interior surface of a mold for casting an article, such as medical device or equipment. The mold is filled with liquid plastic and then the plastic is allowed to solidify. The functionalized powder particles are embedded in the plastic surface wherein the nanostructures may be partially exposed to atmosphere.

Example 22: A functionalized powder is prepared via the method described in Example 1, 2, 3, 4, 5, 6, 7, 8, 9, 10, 11, 12, 13, 14, or 15. The powder is suspended into a metal-adhering paint via stirring. The paint is applied in a thin layer to the exterior surface of a watercraft. The paint is allowed to dry, leaving behind a painted metal surface with partially exposed functionalized powder particles exposed at the paint/atmosphere interface. Due to the presence of nano- and micro-structure at the watercraft surface, the hull may have antifouling and hydrophobic properties that would serve to prevent aquatic life from adhering to the surface of the watercraft and to reduce drag.

Example 23: A functionalized powder is prepared via the method described in Example 1, 2, 3, 4, 5, 6, 7, 8, 9, 10, 11, 12, 13, 14, or 15. Using traditional powder coating techniques, thermoset polymer particles are applied to a surface via electrostatic charge. Subsequently the functionalized powder is applied to the surface. Optionally, the functionalized powder may be applied to the surface via electrostatic charge. The article is then cured under heat to affix the functionalized particles to the article surface. The thermoset polymer acts as a binder between the substrate and the functionalized particles. The surface of the functionalized powder may be partially exposed at the paint/atmosphere interface.

Example 24: A functionalized powder is prepared via the method described in Example 1, 2, 3, 4, 5, 6, 7, 8, 9, 10, 11, 12, 13, 14, or 15. At least a part of a metal article is temporarily melted via heat. Subsequently the functionalized powder is applied to the melted metal. The metal is allowed to solidify, affixing the functionalized particles to the metal article.

Example 25: A functionalized powder is prepared via the method described in Example 1, 2, 3, 4, 5, 6, 7, 8, 9, 10, 11, 12, 13, 14, or 15. A predetermined amount of sterile functionalized powder is added to a sterile vessel or the sterile functionalized powder is affixed to the internal surface of a sterile vessel. Cells, such as $E.\ coli$ or $C.\ albicans$, in an aqueous solution (e.g. 500 μL), such as nutrient broth (or another solution such as NaCl (e.g. 0.14 M)) are added to the vessel comprising functionalized particles. The vessel is then closed and the whole system is agitated/vortexed (e.g. for 30 seconds). Optionally, following agitation/vortexing the vessel is allowed to sit (e.g. for up to 1 hour), to let the contents to settle or the vessel is centrifuged to aid in content separation. FIGS. 30A-30D show an example illustrative representation of this method. The functionalized particle may increase the cell lysing rate and allow intracellular component extraction, for example but not limited to DNA, RNA, macromolecules, proteins, organelles, and metabolites. These intracellular components may then be utilized in downstream assays, experimentation protocols, or tests. Optionally, the functionalized particles may also be chemically functionalized to aid in lysis and/or intracellular component extraction.

Cell lysis with nonfunctionalized particles (e.g. bead beating) may require longer agitation/vortexing durations, than compared with functionalized particles, because the cell lysis relies on ballistic interactions between the nonfunctionalized particle and cell. This may cause the vessel and the temperature-sensitive contents to heat up. Whereas cell lysis with functionalized particles also involve interactions with the particle surface structure and thus may aid in the lysis process. Functionalized particles may require less mechanical energy to lyse cells and therefore may result in a lower thermal load or heat transfer on the vessel and its contents (resulting in less damage to intracellular components).

In one example, functionalized particles were prepared via the method described in Example 7, with an etch duration of 60 minutes and with residual Ag removed. These functionalized particles were sterilized and added to a sterile vessel, along with $E.\ coli$ in 500 μL LB Broth ($OD_{600}$ 1.1). The vessel was vortexed for 30 seconds and allowed to sit for 1 hour at 37° C. Compared with using nonfunctionalized Si particles, the functionalized Si particles showed a 533% increase in lysed $E.\ coli$, as seen in FIG. 31. The nonfunctionalized Si particles lysed 9% of cells via ballistic interaction. Whereas the functionalized Si particles lysed 57% of cells via an additional mechanism, via the interaction between the functionalized surface structure and the cell membrane. Optionally, other types of cells may be lysed with this method. The solution volume, duration, and intensity of agitation may be altered for the application.

Figure 29:
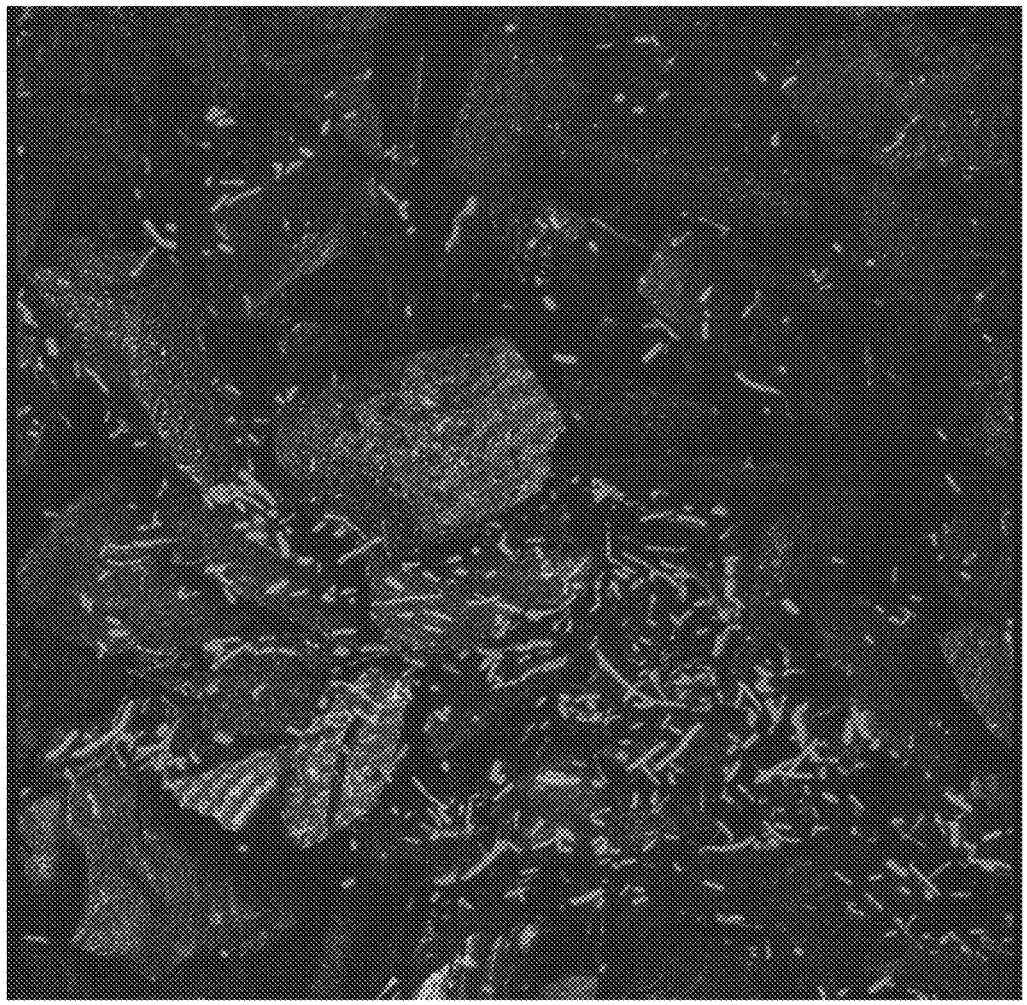
FIG. 29 shows an example Live/Dead fluorescent microscopy composite Z-stack image of *E. coli* on a nanostructured antimicrobial surface coating on an ABS plastic substrate that was prepared via the method discussed in Example 16. The antimicrobial functionalized particles are seen in the background and the rod-shaped features are stained *E. coli*. After 1 hour of growth at 37° C. on the nanostructures, 89±6% of the cells were identified as dead.
Figure 30:
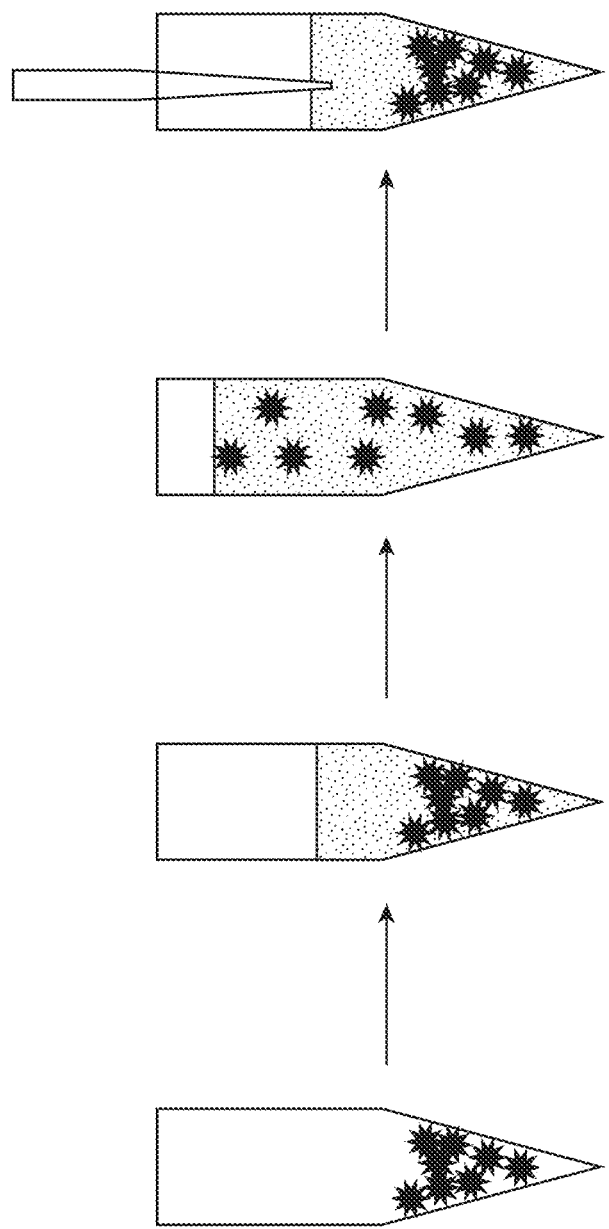
FIGS. 30A-30D illustrate a method of lysing cells using the functionalized powered.
Figure 33A:
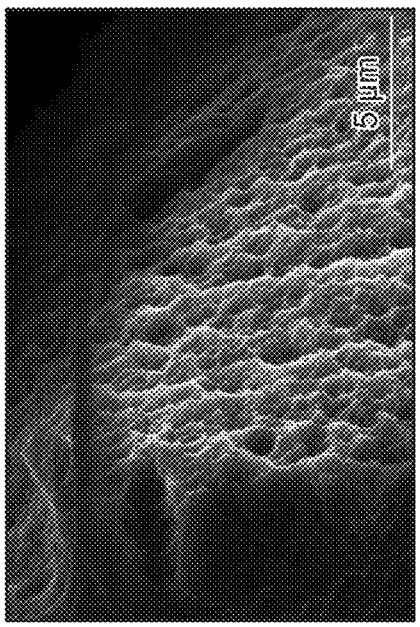
FIGS. 33A-33D show SEM images of functionalized surfaces produced on amorphous SiO particles using Ag-MACE.
Figure 33B:
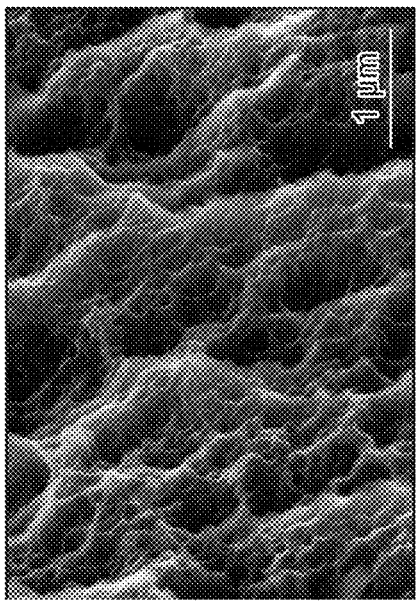
Figure 33C:
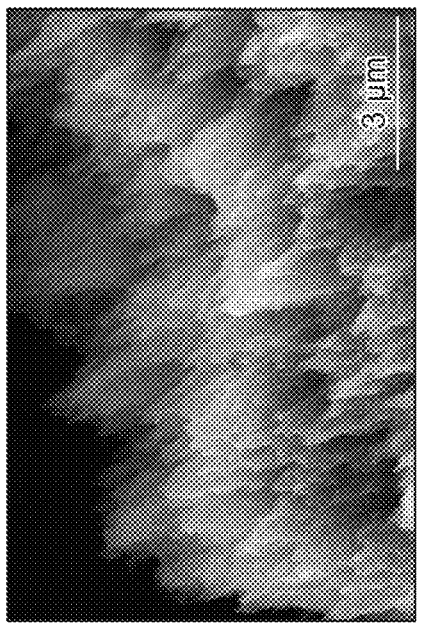
Figure 33D:
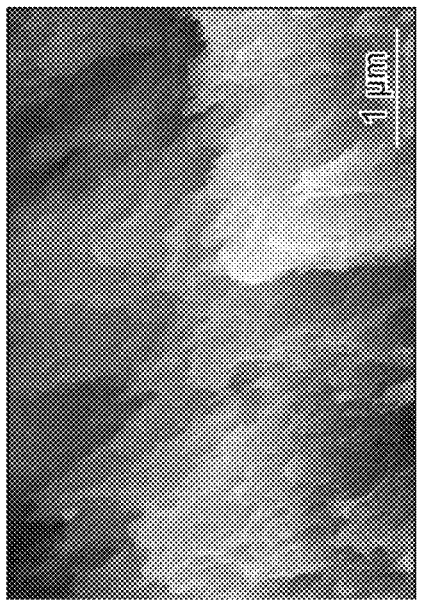
Figure 34:
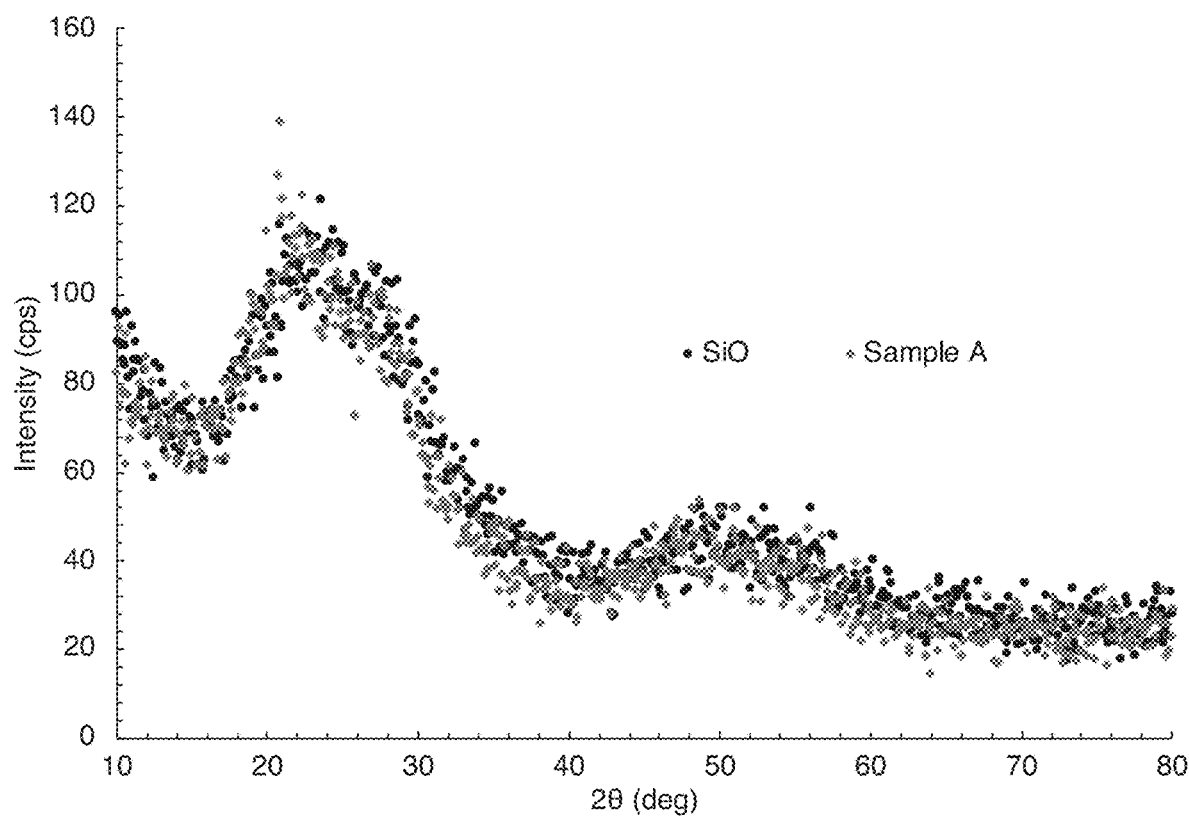
FIG. 34 shows X-ray (Cu Kαi) powder diffraction data for nonfunctionalized and functionalized (Sample A) amorphous SiO powder (particle diameter is between 38-45 µm) prepared via method described in Example 13 measured with a Rigaku Ultima IV 3 kW X-ray diffractometer system. The broad peaks centered near 24° and 50° 2θ indicate that the crystal structure of the SiO particles is amorphous.

Example 26: Surface of an article is prepared via the method described in Examples 16, 17, 18, 19, 23, or 24. The exposed texture of the functionalized particles may have antimicrobial properties that would physically disrupt colonization or kill microorganisms. FIG. 29 shows an example Z-stack composition fluorescent microscopy image of a surface prepared on an ABS plastic substrate via the method described in Example 16, with functionalized particles prepared via the method described in Example 7, with an etch duration of 60 minutes and with residual Ag removed. Cell viability was measured using the BacLight Live/Dead fluorescent kit (L7012 made up of Propidium Iodide and SYTO9 components) with the manufacturer recommended method. Averaging across micrographs of three functionalized surfaces, 89±6% of $E.\ coli$ (adjusted to $OD_{600}$ 0.3) were killed after 1 hour of contact in optimal growth conditions (37° C.). The results show that the bacteria were killed by physical interaction between the functionalized particle surface structure and the bacteria membrane, which does not rely on resistance promoting chemical antimicrobials. Optionally, the functionalized particles may also be chemically functionalized to disrupt colonization or kill microorganisms. Optionally, the hydrophobicity or hydrophilicity may be altered or enhanced by further functionalizing the particle with functional compounds.

Example 27: Functionalized powder particles are prepared via the method described in Example 1, 2, 3, 4, 5, 6, 7, 8, 9, 10, 11, 12, 13, 14, or 15. The functionalized particles have a surface roughness that is greater, across many length scales, than their nonfunctionalized counterparts and may be used to abrade or polish other materials. For example, the abrasive functionalized particles may be used as an abrasive material in abrasive blasting or tumbling.

Example 28: A composite article is prepared via the method described in Examples 16, 17, 18, 19, 23, or 24. The functionalized particles have a surface roughness that is greater, across many length scales, than their nonfunctionalized counterparts and may be used to abrade or polish other materials. The functionalized particle and its application are chosen for its abrasion or polishing properties. The article may be used to abrade or polish other materials or articles.

Example 29: An antireflective surface was prepared via the method described in the method described in Examples 16, 17, 18, 19, 23, or 24. For example, FIG. 37 shows the specular reflectance (190-900 nm wavelength) data from several surfaces at 45° angle of incidence. Samples include, ABS plastic substrates coated via the method described in Example 16 with functionalized powder particles prepared via the method described in Example 2 (Sample E), 11 (Sample D), and 13 (Sample C) and with nonfunctionalized Si powder particles (Sample F). A bare ABS substrate (Sample B) and a polished Si wafer (Sample A) are shown as references. The average reflectance of Sample E shown in FIG. 37 is 0.026% for light between 190-900 nm, 0.029% between 190-380 nm, 0.021% between 380-740 nm, and 0.033% between 740-900 nm. The average reflectance of Sample D is 0.035% for light between 190-900 nm, 0.046% between 190-380 nm, 0.024% between 380-740 nm, and 0.045% between 740-900 nm. The average reflectance of Sample C is 0.077% for light between 190-900 nm, 0.13% between 190-380 nm, 0.055% between 380-740 nm, and 0.062% between 740-900 nm. The average reflectance of Sample F is 0.085% for light between 380-900 nm, 0.081% between 380-740 nm, and 0.095% between 740-900 nm. The decrease in reflectance between the surface comprising nonfunctionalized Si powder particles (Sample F) and the surfaces comprising functionalized particles (Samples C, D, and E) is noticeable across a broad range of wavelengths. For example, the average reflectance of Sample F between 380-740 nm is roughly four times that of Sample E. Additionally, these functionalized particle surface composites are antireflective across a wide angular range due to their nano- and micro-scale morphologies.

Example 30: An antifouling or hydrophobic surface is prepared via the method described in Examples 16, 17, 18, 19, 23, or 24. The micro- and nano-scale texture formed on the surface by the functionalized particles alter the surface energy of the article. For example, FIGS. 27A-27B show contact angle measurements of an ABS plastic substrate functionalized via attached functionalized Si particles, functionalized SiO particles, nonfunctionalized Si particles. A polished Si wafer and bare ABS substrate are shown for comparison. The functionalized ABS plastic substrates were prepared via the method described in Example 16 and had 100% coverage on the examined surfaces. The Si wafer and the particles on Samples 1, 2, 3, 4, and 5 comprise their native oxide. Samples 1, 2, 3, and 4 comprise functionalized particles and have contact angles greater than 90°, indicating that these surfaces are hydrophobic. The bare ABS substrate, polished Si wafer, and Sample 5 have contact angles less than 90°, indicating that these surfaces are hydrophilic. The alteration to the surface energy can be seen when comparing the contact angles of the polished Si wafer, Sample 1, Sample 2, Sample 3, and Sample 5, which all have the same Si chemical composition. The micro-scale texture formed by the nonfunctionalized Si particle surface, Sample 5, shows an increase in contact angle compared to the Si wafer. Samples 1, 2, and 3 show a greater increase in contact angle due to their functionalized surface structure. The combination of low surface energy, hydrophobicity, and antimicrobial properties of some functionalized particles may result in antifouling activity. Optionally, chemical functionalization may increase the hydrophobic or antifouling properties of the coating.

Example 31: A surface is prepared via the method described in Examples 16, 17, 18, 19, 23, or 24. Subsequently, a conductive material is applied to the exposed functionalized particles, via traditional techniques, to form a conductive surface that has a surface area that is at least twice the footprint. The micro- and nano-scale structures will increase the capacitance per footprint area. The micro- and nano-scale geometry may increase electric discharge from the surface. FIG. 5D shows an example cross sectional SEM image of Pt coated hoodoo structures.

Example 32: The band structure of a powder particle is altered by preparing a functionalized powder particle via the method described in Example 1, 2, 3, 4, 5, 6, 7, 8, 9, 10, 11, 12, 13, 14, or 15. The structural functionalization may result in anisotropic expansion and contraction of the crystal lattice, which may result in alterations to the band structure of the particle. The anisotropic lattice alteration may be localized to the portion of the particle that is structurally functionalized (i.e. radially dependent) or may alter the entire particle (i.e. radially independent). This method may alter the band structure without altering the chemical composition of the particle. For example, FIGS. 25A-25B show X-ray diffraction data from nonfunctionalized Si particles and functionalized powder particles prepared via the method described in Example 7, with 90 minutes of etching. Shifts in peak position are seen for the Si(111) and Si(311) peaks for the functionalized powder, which indicates a 0.194% lattice expansion along the <111> direction and a 0.143% contraction along <311> directions, respectively. Whereas the positions for the Si(220), Si(400), and Si(331) peaks remain unchanged. This X-ray data suggests that the crystalline unit cell is anisotropic deformed for the entire particle (45 μm average diameter) due to the structural functionalization (1.5 μm thick) at the surface. Lattice alteration that are radially dependent would have resulted in multi-component Bragg peaks (due to X-ray scattering contributions from the particle core and functionalized region), but this is not present in the X-ray data. Without altering the chemical composition, the crystal lattice for the entire particle was altered by structurally functionalizing a relatively small portion of the particle.

Example 33: A fade resistant opaque pigment is prepared via the method described in Example 1, 2, 3, 4, 5, 6, 7, 8, 9, 10, 11, 12, 13, 14, or 15. Some pigments that they rely on chromophore for their color fade due to high energy radiation (e.g. ultraviolet light) exposure, which damages the molecules that are responsible for the color. The optical properties of the functionalized particles are dependent on both the bulk material properties and its particle surface structure. For example, Samples A, C, E, and F in FIG. 37 have the same bulk composition and crystal structure but have different surface morphologies. The different surface structures have a significant impact on the light reflectance and the appearance of the surface. The matte black appearance of Sample E is due to the functionalized structure of the particles that absorb light structurally. The structurally functionalized particles used as pigments may be more fade resistant because they are not solely reliant on the molecular structure for their color.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A method of lysing a cell, the method comprising:
(a) providing a vessel containing one or more surface etched powder particle(s) within a chamber of the vessel, wherein each of the surface etched powder particle(s) independently comprises a crystalline, polycrystalline, semi-crystalline, or amorphous semiconductor or insulator powder particle, wherein each of the surface etched powder particle(s) has a diameter between 1 and 1,000 microns, and wherein a surface of a powder particle is etched such that each of the surface etched powder particle(s) independently comprises a structure selected from the group consisting of pores, pits, craters, nanowires, cones, pinnacles, hoodoos, coral, cords, walls, fins, ridges, crags, pyramids, and inverted pyramids; and
(b) flowing a composition comprising the cell through the chamber of the vessel, wherein the one or more surface etched powder particle(s) contacts the cell, thereby lysing the cell.

2. The method of claim 1, wherein the structure is a submillistructure.

3. The method of claim 1, wherein each of the surface etched powder particle(s) provided in (a) independently comprises a crystalline or polycrystalline powder particle.

4. The method of claim 1, wherein the structure of each of the surface etched powder particle(s) is independently selected from the group consisting of pores, pits, craters, hoodoos, and coral.

5. The method of claim 1, wherein each of the surface etched powder particle(s) is independently an elemental or compound crystalline or polycrystalline semiconductor powder particle selected from a group consisting of IVA elements, groups IV-VI compounds, groups II-IVB compounds, groups I-VII compounds, groups II-VI compounds, groups III-V compounds, groups IV-IV compounds, transition metal oxides, and compounds comprising three or more elements.

6. The method of claim 1, wherein at least a portion of the surface etched powder particle(s) exhibits an antimicrobial property.

7. The method of claim 1, wherein at least a portion of the surface etched powder particle(s) is configured in a surface of an article.

8. The method of claim 7, wherein the article comprises rubber, plastic, metal, glass, or ceramic.

9. The method of claim 1, wherein the composition comprises a population of cells comprising the cell.

10. The method of claim 9, wherein the method lyses at least 30% of the population of cells.

11. The method of claim 9, wherein the method lyses at least 50% of the population of cells.

12. The method of claim 1, wherein the structure is a first type of structure, and wherein each of the surface etched powder particle(s) independently further comprises a second type of structure.

13. The method of claim 12, wherein the second type of structure of each of the surface etched powder particle(s) is independently selected from the group consisting of pores, pits, craters, nanowires, cones, pinnacles, hoodoos, coral, cords, walls, fins, ridges, crags, pyramids, and inverted pyramids.

14. The method of claim 12, wherein the second type of structure of each of the surface etched powder particle(s) is independently selected from the group consisting of pores, pits, craters, hoodoos, and coral.

15. The method of claim 12, wherein the second type of structure is a submillistructure.

16. The method of claim 1, wherein each of the surface etched powder particle(s) is not embedded within or adhered to a material or a surface of an article.

17. The method of claim 16, wherein each of the surface etched powder particle(s) is in loose powder form.

18. The method of claim 1, wherein the vessel comprises a chamber, and wherein each of the surface etched powder particle(s) is provided within the chamber.

19. The method of claim 18, wherein each of the surface etched powder particle(s) is in loose powder form.

* * * * *